United States Patent
Nonaka et al.

(10) Patent No.: US 8,278,075 B2
(45) Date of Patent: Oct. 2, 2012

(54) L-CYSTEINE-PRODUCING BACTERIUM AND A METHOD FOR PRODUCING L-CYSTEINE

(75) Inventors: Gen Nonaka, Kawasaki (JP); Hiroshi Takagi, Ikoma (JP); Iwao Ohtsu, Ikoma (JP)

(73) Assignees: Ajinomoto Co., Inc., Tokyo (JP); National University Corporation Nara Institute of Science and Technology, Nara (JP)

( * ) Notice: Subject to any disclaimer, the term of this patent is extended or adjusted under 35 U.S.C. 154(b) by 0 days.

(21) Appl. No.: 12/858,590

(22) Filed: Aug. 18, 2010

(65) Prior Publication Data

US 2011/0033902 A1 Feb. 10, 2011

Related U.S. Application Data

(63) Continuation of application No. PCT/JP2009/053021, filed on Feb. 20, 2009.

(30) Foreign Application Priority Data

Feb. 21, 2008 (JP) ................................. 2008-040167

(51) Int. Cl.
- C12P 13/12 (2006.01)
- C12P 13/06 (2006.01)
- C12N 1/20 (2006.01)
- C12N 15/00 (2006.01)
- C07H 21/04 (2006.01)

(52) U.S. Cl. ..................... 435/113; 435/116; 435/252.3; 435/320.1; 536/23.2

(58) Field of Classification Search .................. None
See application file for complete search history.

(56) References Cited

U.S. PATENT DOCUMENTS

| | | | |
|---|---|---|---|
| 5,972,663 | A | 10/1999 | Winterhalter et al. |
| 6,218,168 | B1 | 4/2001 | Leinfelder et al. |
| 7,312,058 | B2 | 12/2007 | Kashiwagi et al. |
| 2003/0077766 | A1 | 4/2003 | Takagi et al. |
| 2005/0112731 | A1 | 5/2005 | Kashiwagi et al. |
| 2005/0221453 | A1 | 10/2005 | Takagi et al. |
| 2008/0076163 | A1 | 3/2008 | Takagi et al. |
| 2009/0226983 | A1 | 9/2009 | Nonaka et al. |
| 2009/0226984 | A1 | 9/2009 | Nonaka et al. |
| 2010/0093045 | A1 | 4/2010 | Takagi et al. |
| 2010/0209977 | A1 | 8/2010 | Takumi et al. |

FOREIGN PATENT DOCUMENTS

| | | |
|---|---|---|
| JP | 11-155571 | 6/1999 |
| JP | 11-221080 | 8/1999 |
| JP | 2992010 | 10/1999 |
| JP | 2002-233384 | 8/2002 |
| JP | 2003-169668 | 6/2003 |
| JP | 2005-245311 | 9/2005 |
| JP | 2005-287333 | 10/2005 |
| WO | WO01/27307 | 4/2001 |
| WO | WO2008/096837 | 8/2008 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
BioCyc Home Page, Summary of *Escherichia coli*, Strain K-12, version 11.6, *E. coli* K-12 Gene: tolC, pp. 1-9.
Daβler, T., et al., "Identification of a major facilitator protein from *Escherichia coli* involved in efflux of metabolites of the cysteine pathway," Mol. Microbiol. 2000;36(5):1101-1112.
Li, Z., et al., "Functional analysis of the *Escherichia coli* outer membrane protein porin TolC and its application to L-cysteine production," Seikagaku, BMB2008, with its full English translation.
Wiriyathanawudhiwong, N., et al., "The outer membrane TolC is involved in cysteine tolerance and overproduction in *Escherichia coli*," Appl. Microbiol. Biotechnol. 2009;81:903-913.
International Search Report for PCT Patent App. No. PCT/JP2009/053021 (Apr. 28, 2009).
U.S. Appl. No. 12/711,299, filed Feb. 24, 2010, Nonaka et al.
U.S. Appl. No. 12/722,094, filed Mar. 11, 2010, Nonaka et al.
Supplementary European Search Report for EP Patent App. No. 09713597.4 (Jun. 15, 2012).

* cited by examiner

*Primary Examiner* — Christian Fronda
(74) *Attorney, Agent, or Firm* — Shelly Guest Cermak; Cermak Nakajima LLP

(57) ABSTRACT

L-Cysteine, L-cystine, a derivative or precursor thereof, or a mixture thereof is produced by culturing a bacterium belonging to the family Enterobacteriaceae, which has L-cysteine-producing ability and has been modified so that the activity of a protein encoded by a tolC gene, for example, a protein defined in the following (a) or (b), is increased in a medium, and by collecting L-cysteine, L-cystine, a derivative or precursor thereof, or a mixture thereof from the medium:
(a) a protein comprising the amino acid sequence of SEQ ID NO: 2,
(b) a protein comprising the amino acid sequence of SEQ ID NO: 2, but wherein one or several amino acid residues are substituted, deleted, inserted or added, increase of which activity in the bacterium improves the ability of the bacterium to produce L-cysteine.

16 Claims, 2 Drawing Sheets

SEQUENCE LISTING

<160> NUMBER OF SEQ ID NOS: 30

<210> SEQ ID NO 1
<211> LENGTH: 1482
<212> TYPE: DNA
<213> ORGANISM: Escherichia coli
<220> FEATURE:
<221> NAME/KEY: CDS
<222> LOCATION: (1)..(1482)

<400> SEQUENCE: 1

| | | | | | | | | | | | | | | | | |
|---|---|---|---|---|---|---|---|---|---|---|---|---|---|---|---|---|
| atg | aag | aaa | ttg | ctc | ccc | att | ctt | atc | ggc | ctg | agc | ctt | tct | ggg | ttc | 48 |
| Met | Lys | Lys | Leu | Leu | Pro | Ile | Leu | Ile | Gly | Leu | Ser | Leu | Ser | Gly | Phe | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| agt | tcg | ttg | agc | cag | gcc | gag | aac | ctg | atg | caa | gtt | tat | cag | caa | gca | 96 |
| Ser | Ser | Leu | Ser | Gln | Ala | Glu | Asn | Leu | Met | Gln | Val | Tyr | Gln | Gln | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| cgc | ctt | agt | aac | ccg | gaa | ttg | cgt | aag | tct | gcc | gcc | gat | cgt | gat | gct | 144 |
| Arg | Leu | Ser | Asn | Pro | Glu | Leu | Arg | Lys | Ser | Ala | Ala | Asp | Arg | Asp | Ala | |
| | | 35 | | | | | 40 | | | | | 45 | | | | |

| | | | | | | | | | | | | | | | | |
|---|---|---|---|---|---|---|---|---|---|---|---|---|---|---|---|---|
| gcc | ttt | gaa | aaa | att | aat | gaa | gcg | cgc | agt | cca | tta | ctg | cca | cag | cta | 192 |
| Ala | Phe | Glu | Lys | Ile | Asn | Glu | Ala | Arg | Ser | Pro | Leu | Leu | Pro | Gln | Leu | |
| 50 | | | | | 55 | | | | | 60 | | | | | | |

| | | | | | | | | | | | | | | | | |
|---|---|---|---|---|---|---|---|---|---|---|---|---|---|---|---|---|
| ggt | tta | ggt | gca | gat | tac | acc | tat | agc | aac | ggc | tac | cgc | gac | gcg | aac | 240 |
| Gly | Leu | Gly | Ala | Asp | Tyr | Thr | Tyr | Ser | Asn | Gly | Tyr | Arg | Asp | Ala | Asn | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ggc | atc | aac | tct | aac | gcg | acc | agt | gcg | tcc | ttg | cag | tta | act | caa | tcc | 288 |
| Gly | Ile | Asn | Ser | Asn | Ala | Thr | Ser | Ala | Ser | Leu | Gln | Leu | Thr | Gln | Ser | |
| | | | | 85 | | | | | 90 | | | | | 95 | | |

| | | | | | | | | | | | | | | | | |
|---|---|---|---|---|---|---|---|---|---|---|---|---|---|---|---|---|
| att | ttt | gat | atg | tcg | aaa | tgg | cgt | gcg | tta | acg | ctg | cag | gaa | aaa | gca | 336 |
| Ile | Phe | Asp | Met | Ser | Lys | Trp | Arg | Ala | Leu | Thr | Leu | Gln | Glu | Lys | Ala | |
| | | | 100 | | | | | 105 | | | | | 110 | | | |

| | | | | | | | | | | | | | | | | |
|---|---|---|---|---|---|---|---|---|---|---|---|---|---|---|---|---|
| gca | ggg | att | cag | gac | gtc | acg | tat | cag | acc | gat | cag | caa | acc | ttg | atc | 384 |
| Ala | Gly | Ile | Gln | Asp | Val | Thr | Tyr | Gln | Thr | Asp | Gln | Gln | Thr | Leu | Ile | |
| | | 115 | | | | | 120 | | | | | 125 | | | | |

| | | | | | | | | | | | | | | | | |
|---|---|---|---|---|---|---|---|---|---|---|---|---|---|---|---|---|
| ctc | aac | acc | gcg | acc | gct | tat | ttc | aac | gtg | ttg | aat | gct | att | gac | gtt | 432 |
| Leu | Asn | Thr | Ala | Thr | Ala | Tyr | Phe | Asn | Val | Leu | Asn | Ala | Ile | Asp | Val | |
| | 130 | | | | | 135 | | | | | 140 | | | | | |

| | | | | | | | | | | | | | | | | |
|---|---|---|---|---|---|---|---|---|---|---|---|---|---|---|---|---|
| ctt | tcc | tat | aca | cag | gca | caa | aaa | gaa | gcg | atc | tac | cgt | caa | tta | gat | 480 |
| Leu | Ser | Tyr | Thr | Gln | Ala | Gln | Lys | Glu | Ala | Ile | Tyr | Arg | Gln | Leu | Asp | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| caa | acc | acc | caa | cgt | ttt | aac | gtg | ggc | ctg | gta | gcg | atc | acc | gac | gtg | 528 |
| Gln | Thr | Thr | Gln | Arg | Phe | Asn | Val | Gly | Leu | Val | Ala | Ile | Thr | Asp | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| cag | aac | gcc | cgc | gca | cag | tac | gat | acc | gtg | ctg | gcg | aac | gaa | gtg | acc | 576 |
| Gln | Asn | Ala | Arg | Ala | Gln | Tyr | Asp | Thr | Val | Leu | Ala | Asn | Glu | Val | Thr | |
| | | | 180 | | | | | 185 | | | | | 190 | | | |

| | | | | | | | | | | | | | | | | |
|---|---|---|---|---|---|---|---|---|---|---|---|---|---|---|---|---|
| gca | cgt | aat | aac | ctt | gat | aac | gcg | gta | gag | cag | ctg | cgc | cag | atc | acc | 624 |
| Ala | Arg | Asn | Asn | Leu | Asp | Asn | Ala | Val | Glu | Gln | Leu | Arg | Gln | Ile | Thr | |
| | | 195 | | | | | 200 | | | | | 205 | | | | |

| | | | | | | | | | | | | | | | | |
|---|---|---|---|---|---|---|---|---|---|---|---|---|---|---|---|---|
| ggt | aac | tac | tat | ccg | gaa | ctg | gct | gcg | ctg | aat | gtc | gaa | aac | ttt | aaa | 672 |
| Gly | Asn | Tyr | Tyr | Pro | Glu | Leu | Ala | Ala | Leu | Asn | Val | Glu | Asn | Phe | Lys | |
| | 210 | | | | | 215 | | | | | 220 | | | | | |

| | | | | | | | | | | | | | | | | |
|---|---|---|---|---|---|---|---|---|---|---|---|---|---|---|---|---|
| acc | gac | aaa | cca | cag | ccg | gtt | aac | gcg | ctg | ctg | aaa | gaa | gcc | gaa | aaa | 720 |
| Thr | Asp | Lys | Pro | Gln | Pro | Val | Asn | Ala | Leu | Leu | Lys | Glu | Ala | Glu | Lys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cgc | aac | ctg | tcg | ctg | tta | cag | gca | cgc | ttg | agc | cag | gac | ctg | gcg | cgc | 768 |
| Arg | Asn | Leu | Ser | Leu | Leu | Gln | Ala | Arg | Leu | Ser | Gln | Asp | Leu | Ala | Arg | |
| | | | | 245 | | | | | 250 | | | | | 255 | | |

| | | | | | | | | | | | | | | | | |
|---|---|---|---|---|---|---|---|---|---|---|---|---|---|---|---|---|
| gag | caa | att | cgc | cag | gcg | cag | gat | ggt | cac | tta | ccg | act | ctg | gat | tta | 816 |

-continued

```
Glu Gln Ile Arg Gln Ala Gln Asp Gly His Leu Pro Thr Leu Asp Leu
            260                 265                 270 acg gct tct acc ggg att tct gac acc tct tat agc ggt tcg aaa acc    864
Thr Ala Ser Thr Gly Ile Ser Asp Thr Ser Tyr Ser Gly Ser Lys Thr
        275                 280                 285 cgt ggt gcc gct ggt acc cag tat gac gat agc aat atg ggc cag aac    912
Arg Gly Ala Ala Gly Thr Gln Tyr Asp Asp Ser Asn Met Gly Gln Asn
    290                 295                 300 aaa gtt ggc ctg agc ttc tcg ctg ccg att tat cag ggc gga atg gtt    960
Lys Val Gly Leu Ser Phe Ser Leu Pro Ile Tyr Gln Gly Gly Met Val
305                 310                 315                 320 aac tcg cag gtg aaa cag gca cag tac aac ttt gtc ggt gcc agc gag   1008
Asn Ser Gln Val Lys Gln Ala Gln Tyr Asn Phe Val Gly Ala Ser Glu
                325                 330                 335 caa ctg gaa agt gcc cat cgt agc gtc gtg cag acc gtg cgt tcc tcc   1056
Gln Leu Glu Ser Ala His Arg Ser Val Val Gln Thr Val Arg Ser Ser
            340                 345                 350 ttc aac aac att aat gca tct atc agt agc att aac gcc tac aaa caa   1104
Phe Asn Asn Ile Asn Ala Ser Ile Ser Ser Ile Asn Ala Tyr Lys Gln
        355                 360                 365 gcc gta gtt tcc gct caa agc tca tta gac gcg atg gaa gcg ggc tac   1152
Ala Val Val Ser Ala Gln Ser Ser Leu Asp Ala Met Glu Ala Gly Tyr
    370                 375                 380 tcg gtc ggt acg cgt acc att gtt gat gtg ttg gat gcg acc acc acg   1200
Ser Val Gly Thr Arg Thr Ile Val Asp Val Leu Asp Ala Thr Thr Thr
385                 390                 395                 400 ttg tac aac gcc aag caa gag ctg gcg aat gcg cgt tat aac tac ctg   1248
Leu Tyr Asn Ala Lys Gln Glu Leu Ala Asn Ala Arg Tyr Asn Tyr Leu
                405                 410                 415 att aat cag ctg aat att aag tca gct ctg ggt acg ttg aac gag cag   1296
Ile Asn Gln Leu Asn Ile Lys Ser Ala Leu Gly Thr Leu Asn Glu Gln
            420                 425                 430 gat ctg ctg gca ctg aac aat gcg ctg agc aaa ccg gtt tcc act aat   1344
Asp Leu Leu Ala Leu Asn Asn Ala Leu Ser Lys Pro Val Ser Thr Asn
        435                 440                 445 ccg gaa aac gtt gca ccg caa acg ccg gaa cag aat gct att gct gat   1392
Pro Glu Asn Val Ala Pro Gln Thr Pro Glu Gln Asn Ala Ile Ala Asp
    450                 455                 460 ggt tat gcg cct gat agc ccg gca cca gtc gtt cag caa aca tcc gca   1440
Gly Tyr Ala Pro Asp Ser Pro Ala Pro Val Val Gln Gln Thr Ser Ala
465                 470                 475                 480 cgc act acc acc agt aac ggt cat aac cct ttc cgt aac tga           1482
Arg Thr Thr Thr Ser Asn Gly His Asn Pro Phe Arg Asn
                485                 490
```

<210> SEQ ID NO 2
<211> LENGTH: 493
<212> TYPE: PRT
<213> ORGANISM: Escherichia coli

<400> SEQUENCE: 2

```
Met Lys Lys Leu Leu Pro Ile Leu Ile Gly Leu Ser Leu Ser Gly Phe
1               5                   10                  15

Ser Ser Leu Ser Gln Ala Glu Asn Leu Met Gln Val Tyr Gln Gln Ala
            20                  25                  30

Arg Leu Ser Asn Pro Glu Leu Arg Lys Ser Ala Ala Asp Arg Asp Ala
        35                  40                  45

Ala Phe Glu Lys Ile Asn Glu Ala Arg Ser Pro Leu Leu Pro Gln Leu
    50                  55                  60

Gly Leu Gly Ala Asp Tyr Thr Tyr Ser Asn Gly Tyr Arg Asp Ala Asn
```

```
                65                  70                  75                  80
Gly Ile Asn Ser Asn Ala Thr Ser Ala Ser Leu Gln Leu Thr Gln Ser
                    85                  90                  95
Ile Phe Asp Met Ser Lys Trp Arg Ala Leu Thr Leu Gln Glu Lys Ala
                100                 105                 110
Ala Gly Ile Gln Asp Val Thr Tyr Gln Thr Asp Gln Thr Leu Ile
                115                 120                 125
Leu Asn Thr Ala Thr Ala Tyr Phe Asn Val Leu Asn Ala Ile Asp Val
    130                 135                 140
Leu Ser Tyr Thr Gln Ala Gln Lys Glu Ala Ile Tyr Arg Gln Leu Asp
145                 150                 155                 160
Gln Thr Thr Gln Arg Phe Asn Val Gly Leu Val Ala Ile Thr Asp Val
                    165                 170                 175
Gln Asn Ala Arg Ala Gln Tyr Asp Thr Val Leu Ala Asn Glu Val Thr
                180                 185                 190
Ala Arg Asn Asn Leu Asp Asn Ala Val Glu Gln Leu Arg Gln Ile Thr
                195                 200                 205
Gly Asn Tyr Tyr Pro Glu Leu Ala Ala Leu Asn Val Glu Asn Phe Lys
    210                 215                 220
Thr Asp Lys Pro Gln Pro Val Asn Ala Leu Leu Lys Glu Ala Glu Lys
225                 230                 235                 240
Arg Asn Leu Ser Leu Leu Gln Ala Arg Leu Ser Gln Asp Leu Ala Arg
                    245                 250                 255
Glu Gln Ile Arg Gln Ala Gln Asp Gly His Leu Pro Thr Leu Asp Leu
                260                 265                 270
Thr Ala Ser Thr Gly Ile Ser Asp Thr Ser Tyr Ser Gly Ser Lys Thr
                275                 280                 285
Arg Gly Ala Ala Gly Thr Gln Tyr Asp Asp Ser Asn Met Gly Gln Asn
    290                 295                 300
Lys Val Gly Leu Ser Phe Ser Leu Pro Ile Tyr Gln Gly Gly Met Val
305                 310                 315                 320
Asn Ser Gln Val Lys Gln Ala Gln Tyr Asn Phe Val Gly Ala Ser Glu
                    325                 330                 335
Gln Leu Glu Ser Ala His Arg Ser Val Val Gln Thr Val Arg Ser Ser
                340                 345                 350
Phe Asn Asn Ile Asn Ala Ser Ile Ser Ile Asn Ala Tyr Lys Gln
                355                 360                 365
Ala Val Val Ser Ala Gln Ser Ser Leu Asp Ala Met Glu Ala Gly Tyr
    370                 375                 380
Ser Val Gly Thr Arg Thr Ile Val Asp Val Leu Asp Ala Thr Thr
385                 390                 395                 400
Leu Tyr Asn Ala Lys Gln Glu Leu Ala Asn Ala Arg Tyr Asn Tyr Leu
                    405                 410                 415
Ile Asn Gln Leu Asn Ile Lys Ser Ala Leu Gly Thr Leu Asn Glu Gln
                420                 425                 430
Asp Leu Leu Ala Leu Asn Asn Ala Leu Ser Lys Pro Val Ser Thr Asn
                435                 440                 445
Pro Glu Asn Val Ala Pro Gln Thr Pro Glu Gln Asn Ala Ile Ala Asp
    450                 455                 460
Gly Tyr Ala Pro Asp Ser Pro Ala Pro Val Val Gln Gln Thr Ser Ala
465                 470                 475                 480
Arg Thr Thr Thr Ser Asn Gly His Asn Pro Phe Arg Asn
                    485                 490
```

```
<210> SEQ ID NO 3
<211> LENGTH: 26
<212> TYPE: DNA
<213> ORGANISM: Artificial Sequence
<220> FEATURE:
<223> OTHER INFORMATION: primer

<400> SEQUENCE: 3
gggaattcat cgcttcggcg ttgaaa                                       26

<210> SEQ ID NO 4
<211> LENGTH: 29
<212> TYPE: DNA
<213> ORGANISM: Artificial Sequence
<220> FEATURE:
<223> OTHER INFORMATION: primer

<400> SEQUENCE: 4
ggctctagaa gcggtattga gagagatta                                    29

<210> SEQ ID NO 5
<211> LENGTH: 17
<212> TYPE: DNA
<213> ORGANISM: Artificial Sequence
<220> FEATURE:
<223> OTHER INFORMATION: primer

<400> SEQUENCE: 5
caggaaacag ctatgac                                                 17

<210> SEQ ID NO 6
<211> LENGTH: 17
<212> TYPE: DNA
<213> ORGANISM: Artificial Sequence
<220> FEATURE:
<223> OTHER INFORMATION: primer

<400> SEQUENCE: 6
ctgcaatctg tgacgct                                                 17

<210> SEQ ID NO 7
<211> LENGTH: 17
<212> TYPE: DNA
<213> ORGANISM: Artificial Sequence
<220> FEATURE:
<223> OTHER INFORMATION: primer

<400> SEQUENCE: 7
aatggatata gaccagc                                                 17

<210> SEQ ID NO 8
<211> LENGTH: 17
<212> TYPE: DNA
<213> ORGANISM: Artificial Sequence
<220> FEATURE:
<223> OTHER INFORMATION: primer

<400> SEQUENCE: 8
gctggtctat atccatt                                                 17

<210> SEQ ID NO 9
<211> LENGTH: 35
<212> TYPE: DNA
<213> ORGANISM: Artificial Sequence
<220> FEATURE:
<223> OTHER INFORMATION: primer
```

<400> SEQUENCE: 9
cgcggatcca atggtcataa atggcagcgt agcgc                              35

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
cgcggatccg cagggcgttg cggaacaaac                                    30

<210> SEQ ID NO 11
<211> LENGTH: 1488
<212> TYPE: DNA
<213> ORGANISM: Shigella boydii
<220> FEATURE:
<221> NAME/KEY: CDS
<222> LOCATION: (1)..(1488)

<400> SEQUENCE: 11

| | | | | | | | | | | | | | | | | |
|---|---|---|---|---|---|---|---|---|---|---|---|---|---|---|---|---|
| atg | caa | atg | aag | aaa | ttg | ctc | ccc | att | ctt | atc | ggc | ctg | agc | ctt | tct | 48 |
| Met | Gln | Met | Lys | Lys | Leu | Leu | Pro | Ile | Leu | Ile | Gly | Leu | Ser | Leu | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggg | ttc | agt | tcg | ttg | agc | cag | gcc | gag | aac | ctg | atg | caa | gtt | tat | cag | 96 |
| Gly | Phe | Ser | Ser | Leu | Ser | Gln | Ala | Glu | Asn | Leu | Met | Gln | Val | Tyr | Gln | |
| | | | 20 | | | | | 25 | | | | | 30 | | | |

| | | | | | | | | | | | | | | | | |
|---|---|---|---|---|---|---|---|---|---|---|---|---|---|---|---|---|
| caa | gca | cgc | ctt | agt | aac | ccg | gaa | ttg | cgt | aag | tct | gcc | gcc | gat | cgt | 144 |
| Gln | Ala | Arg | Leu | Ser | Asn | Pro | Glu | Leu | Arg | Lys | Ser | Ala | Ala | Asp | Arg | |
| | | 35 | | | | | 40 | | | | | 45 | | | | |

| | | | | | | | | | | | | | | | | |
|---|---|---|---|---|---|---|---|---|---|---|---|---|---|---|---|---|
| gat | gct | gcc | ttt | gaa | aaa | att | aat | gaa | gcg | cgc | agt | cca | tta | ctg | cca | 192 |
| Asp | Ala | Ala | Phe | Glu | Lys | Ile | Asn | Glu | Ala | Arg | Ser | Pro | Leu | Leu | Pro | |
| 50 | | | | | 55 | | | | | 60 | | | | | | |

| | | | | | | | | | | | | | | | | |
|---|---|---|---|---|---|---|---|---|---|---|---|---|---|---|---|---|
| cag | cta | ggt | tta | ggt | gca | gat | tac | acc | tat | agc | aac | ggc | tac | cgc | gac | 240 |
| Gln | Leu | Gly | Leu | Gly | Ala | Asp | Tyr | Thr | Tyr | Ser | Asn | Gly | Tyr | Arg | Asp | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gcg | aac | ggc | atc | aac | tcg | aac | gcg | acc | agt | gcg | tcc | ctg | cag | tta | act | 288 |
| Ala | Asn | Gly | Ile | Asn | Ser | Asn | Ala | Thr | Ser | Ala | Ser | Leu | Gln | Leu | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| caa | tcc | att | ttt | gat | atg | tcg | aaa | tgg | cgt | gcg | tta | acg | ctg | cag | gaa | 336 |
| Gln | Ser | Ile | Phe | Asp | Met | Ser | Lys | Trp | Arg | Ala | Leu | Thr | Leu | Gln | Glu | |
| | | | 100 | | | | | 105 | | | | | 110 | | | |

| | | | | | | | | | | | | | | | | |
|---|---|---|---|---|---|---|---|---|---|---|---|---|---|---|---|---|
| aaa | gca | gca | ggg | att | cag | gac | atc | aca | tat | cag | acc | gat | cag | caa | acc | 384 |
| Lys | Ala | Ala | Gly | Ile | Gln | Asp | Ile | Thr | Tyr | Gln | Thr | Asp | Gln | Gln | Thr | |
| | | 115 | | | | | 120 | | | | | 125 | | | | |

| | | | | | | | | | | | | | | | | |
|---|---|---|---|---|---|---|---|---|---|---|---|---|---|---|---|---|
| ttg | atc | ctc | aac | acc | gcg | acc | gct | tat | ttc | aac | gtg | ttg | aat | gct | att | 432 |
| Leu | Ile | Leu | Asn | Thr | Ala | Thr | Ala | Tyr | Phe | Asn | Val | Leu | Asn | Ala | Ile | |
| | 130 | | | | | 135 | | | | | 140 | | | | | |

| | | | | | | | | | | | | | | | | |
|---|---|---|---|---|---|---|---|---|---|---|---|---|---|---|---|---|
| gac | gtt | ctt | tcc | tat | aca | cag | gca | caa | aaa | gaa | gcg | atc | tac | cgt | caa | 480 |
| Asp | Val | Leu | Ser | Tyr | Thr | Gln | Ala | Gln | Lys | Glu | Ala | Ile | Tyr | Arg | Gln | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tta | gat | caa | acc | acc | caa | cgt | ttt | aac | gtg | ggc | ctg | gta | gcg | atc | acc | 528 |
| Leu | Asp | Gln | Thr | Thr | Gln | Arg | Phe | Asn | Val | Gly | Leu | Val | Ala | Ile | Thr | |
| | | | | 165 | | | | | 170 | | | | | 175 | | |

| | | | | | | | | | | | | | | | | |
|---|---|---|---|---|---|---|---|---|---|---|---|---|---|---|---|---|
| gac | gtg | cag | aac | gcc | cgc | gcg | cag | tac | gat | acc | gtg | ctg | gcg | aac | gaa | 576 |
| Asp | Val | Gln | Asn | Ala | Arg | Ala | Gln | Tyr | Asp | Thr | Val | Leu | Ala | Asn | Glu | |
| | | | 180 | | | | | 185 | | | | | 190 | | | |

| | | | | | | | | | | | | | | | | |
|---|---|---|---|---|---|---|---|---|---|---|---|---|---|---|---|---|
| gtg | acc | gca | cgt | aat | aac | ctt | gat | aac | gcg | gta | gag | cag | ctg | cgc | cag | 624 |
| Val | Thr | Ala | Arg | Asn | Asn | Leu | Asp | Asn | Ala | Val | Glu | Gln | Leu | Arg | Gln | |
| | | 195 | | | | | 200 | | | | | 205 | | | | |

| | | | | | | | | | | | | | | | | |
|---|---|---|---|---|---|---|---|---|---|---|---|---|---|---|---|---|
| atc | acc | ggt | aac | tac | tat | ccg | gaa | ctg | gcg | gcg | ctg | aat | gtc | gaa | aac | 672 |

```
Ile Thr Gly Asn Tyr Tyr Pro Glu Leu Ala Ala Leu Asn Val Glu Asn
    210                 215                 220 ttt aaa acc gac aaa cca cag ccg gtt aac gcg ctg ctg aaa gaa gcc        720
Phe Lys Thr Asp Lys Pro Gln Pro Val Asn Ala Leu Leu Lys Glu Ala
225                 230                 235                 240 gaa aaa cgc aac ctg tcg ctg tta cag gca cgc ttg agc cag gac ctg        768
Glu Lys Arg Asn Leu Ser Leu Leu Gln Ala Arg Leu Ser Gln Asp Leu
                245                 250                 255 gcg cgc gag caa att cgc cag gcg cag gat ggt cac tta ccg acg ctg        816
Ala Arg Glu Gln Ile Arg Gln Ala Gln Asp Gly His Leu Pro Thr Leu
            260                 265                 270 gat tta acg gct tct acc ggg att tct gac acc tct tat agc ggt tcg        864
Asp Leu Thr Ala Ser Thr Gly Ile Ser Asp Thr Ser Tyr Ser Gly Ser
        275                 280                 285 aaa act cgt ggt gcc gct ggt acc cag tat gac gac agc aat atg ggc        912
Lys Thr Arg Gly Ala Ala Gly Thr Gln Tyr Asp Asp Ser Asn Met Gly
    290                 295                 300 cag aac aaa gtg ggc ctg agc ttc tcg ctg ccg att tat cag ggc gga        960
Gln Asn Lys Val Gly Leu Ser Phe Ser Leu Pro Ile Tyr Gln Gly Gly
305                 310                 315                 320 atg gtt aac tcg cag gtg aaa cag gcc cag tac aac ttt gtt ggt gcc       1008
Met Val Asn Ser Gln Val Lys Gln Ala Gln Tyr Asn Phe Val Gly Ala
                325                 330                 335 agc gag caa ctg gaa agc gcg cat cgt agc atc gtg caa acc gta cgt       1056
Ser Glu Gln Leu Glu Ser Ala His Arg Ser Ile Val Gln Thr Val Arg
            340                 345                 350 tcc tcc ttc aac aac att aat gca tct atc agt agc att aac gcc tac       1104
Ser Ser Phe Asn Asn Ile Asn Ala Ser Ile Ser Ser Ile Asn Ala Tyr
        355                 360                 365 aaa caa gcc gta gtt tcc gct caa agc tca tta gac gcg atg gaa gcg       1152
Lys Gln Ala Val Val Ser Ala Gln Ser Ser Leu Asp Ala Met Glu Ala
    370                 375                 380 ggc tac tcg gtc ggt acg cgt acc att gtt gat gtg ttg gat gca acc       1200
Gly Tyr Ser Val Gly Thr Arg Thr Ile Val Asp Val Leu Asp Ala Thr
385                 390                 395                 400 acc acg ctg tac aac gct aag caa gag ctg gca aat gcg cgt tat aac       1248
Thr Thr Leu Tyr Asn Ala Lys Gln Glu Leu Ala Asn Ala Arg Tyr Asn
                405                 410                 415 tac ctg att aat cag ctg aat att aag tca gcc ctg ggt acg ttg aac       1296
Tyr Leu Ile Asn Gln Leu Asn Ile Lys Ser Ala Leu Gly Thr Leu Asn
            420                 425                 430 gag cag gat ctg ctg gca ctg aac aat gcg ctg agc aaa ccg gtt tcc       1344
Glu Gln Asp Leu Leu Ala Leu Asn Asn Ala Leu Ser Lys Pro Val Ser
        435                 440                 445 act aat ccg gaa aac gtt gcc ccg caa acg ccg gaa cag aat gct att       1392
Thr Asn Pro Glu Asn Val Ala Pro Gln Thr Pro Glu Gln Asn Ala Ile
    450                 455                 460 gct gat ggt tat gcg cct gat agc ccg gca ccc gtc gtt cag caa aca       1440
Ala Asp Gly Tyr Ala Pro Asp Ser Pro Ala Pro Val Val Gln Gln Thr
465                 470                 475                 480 tcc gca cgc act acc acc agt aac ggt cat aac cct ttc cgt aac tga       1488
Ser Ala Arg Thr Thr Thr Ser Asn Gly His Asn Pro Phe Arg Asn
                485                 490                 495

<210> SEQ ID NO 12
<211> LENGTH: 495
<212> TYPE: PRT
<213> ORGANISM: Shigella boydii

<400> SEQUENCE: 12

Met Gln Met Lys Lys Leu Leu Pro Ile Leu Ile Gly Leu Ser Leu Ser
```

```
1               5                  10                 15
Gly Phe Ser Ser Leu Ser Gln Ala Glu Asn Leu Met Gln Val Tyr Gln
                 20                 25                 30

Gln Ala Arg Leu Ser Asn Pro Glu Leu Arg Lys Ser Ala Ala Asp Arg
                 35                 40                 45

Asp Ala Ala Phe Glu Lys Ile Asn Glu Ala Arg Ser Pro Leu Leu Pro
 50                 55                 60

Gln Leu Gly Leu Gly Ala Asp Tyr Thr Tyr Ser Asn Gly Tyr Arg Asp
 65                 70                 75                 80

Ala Asn Gly Ile Asn Ser Asn Ala Thr Ser Ala Ser Leu Gln Leu Thr
                 85                 90                 95

Gln Ser Ile Phe Asp Met Ser Lys Trp Arg Ala Leu Thr Leu Gln Glu
                100                105                110

Lys Ala Ala Gly Ile Gln Asp Ile Thr Tyr Gln Thr Asp Gln Gln Thr
                115                120                125

Leu Ile Leu Asn Thr Ala Thr Ala Tyr Phe Asn Val Leu Asn Ala Ile
                130                135                140

Asp Val Leu Ser Tyr Thr Gln Ala Gln Lys Glu Ala Ile Tyr Arg Gln
145                150                155                160

Leu Asp Gln Thr Thr Gln Arg Phe Asn Val Gly Leu Val Ala Ile Thr
                165                170                175

Asp Val Gln Asn Ala Arg Ala Gln Tyr Asp Thr Val Leu Ala Asn Glu
                180                185                190

Val Thr Ala Arg Asn Asn Leu Asp Asn Ala Val Glu Gln Leu Arg Gln
                195                200                205

Ile Thr Gly Asn Tyr Tyr Pro Glu Leu Ala Ala Leu Asn Val Glu Asn
                210                215                220

Phe Lys Thr Asp Lys Pro Gln Pro Val Asn Ala Leu Leu Lys Glu Ala
225                230                235                240

Glu Lys Arg Asn Leu Ser Leu Leu Gln Ala Arg Leu Ser Gln Asp Leu
                245                250                255

Ala Arg Glu Gln Ile Arg Gln Ala Gln Asp Gly His Leu Pro Thr Leu
                260                265                270

Asp Leu Thr Ala Ser Thr Gly Ile Ser Asp Thr Ser Tyr Ser Gly Ser
                275                280                285

Lys Thr Arg Gly Ala Ala Gly Thr Gln Tyr Asp Asp Ser Asn Met Gly
                290                295                300

Gln Asn Lys Val Gly Leu Ser Phe Ser Leu Pro Ile Tyr Gln Gly Gly
305                310                315                320

Met Val Asn Ser Gln Val Lys Gln Ala Gln Tyr Asn Phe Val Gly Ala
                325                330                335

Ser Glu Gln Leu Glu Ser Ala His Arg Ser Ile Val Gln Thr Val Arg
                340                345                350

Ser Ser Phe Asn Asn Ile Asn Ala Ser Ile Ser Ser Ile Asn Ala Tyr
                355                360                365

Lys Gln Ala Val Val Ser Ala Gln Ser Ser Leu Asp Ala Met Glu Ala
                370                375                380

Gly Tyr Ser Val Gly Thr Arg Thr Ile Val Asp Val Leu Asp Ala Thr
385                390                395                400

Thr Thr Leu Tyr Asn Ala Lys Gln Glu Leu Ala Asn Ala Arg Tyr Asn
                405                410                415

Tyr Leu Ile Asn Gln Leu Asn Ile Lys Ser Ala Leu Gly Thr Leu Asn
                420                425                430
```

```
Glu Gln Asp Leu Leu Ala Leu Asn Asn Ala Leu Ser Lys Pro Val Ser
            435                 440                 445

Thr Asn Pro Glu Asn Val Ala Pro Gln Thr Pro Gln Asn Ala Ile
    450                 455                 460

Ala Asp Gly Tyr Ala Pro Asp Ser Pro Ala Pro Val Val Gln Gln Thr
465                 470                 475                 480

Ser Ala Arg Thr Thr Thr Ser Asn Gly His Asn Pro Phe Arg Asn
                485                 490                 495

<210> SEQ ID NO 13
<211> LENGTH: 1482
<212> TYPE: DNA
<213> ORGANISM: Shigella flexneri
<220> FEATURE:
<221> NAME/KEY: CDS
<222> LOCATION: (1)..(1482)

<400> SEQUENCE: 13 atg aag aaa ttg ctc ccc att ctt atc ggc ctg agc ctt tct ggg ttc      48
Met Lys Lys Leu Leu Pro Ile Leu Ile Gly Leu Ser Leu Ser Gly Phe
1               5                   10                  15 agt tcg ttg agc cag gcc gag aac ctg atg caa gtt tat cag caa gca      96
Ser Ser Leu Ser Gln Ala Glu Asn Leu Met Gln Val Tyr Gln Gln Ala
                20                  25                  30 cgc ctt agt aac ccg gaa ttg cgt aag tct gcc gcc gat cgt gat gct     144
Arg Leu Ser Asn Pro Glu Leu Arg Lys Ser Ala Ala Asp Arg Asp Ala
            35                  40                  45 gcc ttt gaa aaa att aat gaa gcg cgc agt cca tta ctg cca cag cta     192
Ala Phe Glu Lys Ile Asn Glu Ala Arg Ser Pro Leu Leu Pro Gln Leu
        50                  55                  60 ggt tta ggt gca gat tac acc tat agc aac ggc tac cgc gac gcg aac     240
Gly Leu Gly Ala Asp Tyr Thr Tyr Ser Asn Gly Tyr Arg Asp Ala Asn
65                  70                  75                  80 ggc atc aac tcg aac gcg acc agt gcg tcc ctg cag tta act caa tcc     288
Gly Ile Asn Ser Asn Ala Thr Ser Ala Ser Leu Gln Leu Thr Gln Ser
                85                  90                  95 att ttt gat atg tcg aaa tgg cgt gcg tta acg ctg cag gaa aaa gca     336
Ile Phe Asp Met Ser Lys Trp Arg Ala Leu Thr Leu Gln Glu Lys Ala
                100                 105                 110 gca ggg att cag gac gtc aca tat cag acc gat cag caa acc ttg atc     384
Ala Gly Ile Gln Asp Val Thr Tyr Gln Thr Asp Gln Gln Thr Leu Ile
            115                 120                 125 ctc aac acc gcg acc gct tat ttc aac gtg ttg aat gct att gac gtt     432
Leu Asn Thr Ala Thr Ala Tyr Phe Asn Val Leu Asn Ala Ile Asp Val
        130                 135                 140 ctt tcc tat aca cag gca caa aaa gaa gcg atc tac cgt caa tta gat     480
Leu Ser Tyr Thr Gln Ala Gln Lys Glu Ala Ile Tyr Arg Gln Leu Asp
145                 150                 155                 160 caa acc acc caa cgt ttt aac gtg ggc ctg gta gcg atc acc gac gtg     528
Gln Thr Thr Gln Arg Phe Asn Val Gly Leu Val Ala Ile Thr Asp Val
                165                 170                 175 cag aac gcc cgc gcg cag tac gat acc gtg ctg gcg aac gaa gtg acc     576
Gln Asn Ala Arg Ala Gln Tyr Asp Thr Val Leu Ala Asn Glu Val Thr
                180                 185                 190 gca cgt aat aac ctt gat aac gcg gta gag cag ctg cgc cag atc acc     624
Ala Arg Asn Asn Leu Asp Asn Ala Val Glu Gln Leu Arg Gln Ile Thr
            195                 200                 205 ggt aac tac tat ccg gaa ctg gcg gcg ctg aat gtc gaa aac ttt aaa     672
Gly Asn Tyr Tyr Pro Glu Leu Ala Ala Leu Asn Val Glu Asn Phe Lys
        210                 215                 220 acc gac aaa cca cag ccg gtt aac gcg ctg ctg aaa gaa gcc gaa aaa     720
```

```
Thr Asp Lys Pro Gln Pro Val Asn Ala Leu Leu Lys Glu Ala Glu Lys
225                 230                 235                 240 cgc aac ctg tcg ctg tta cag gca cgc ttg agc cag gac ctg gag cgc    768
Arg Asn Leu Ser Leu Leu Gln Ala Arg Leu Ser Gln Asp Leu Glu Arg
                245                 250                 255 gag caa att cgc cag gcg cag gat ggt cac tta ccg act ctg gat tta    816
Glu Gln Ile Arg Gln Ala Gln Asp Gly His Leu Pro Thr Leu Asp Leu
            260                 265                 270 acg gct tct acc ggg att tct gac acc tct tat agc ggt tcg aaa acc    864
Thr Ala Ser Thr Gly Ile Ser Asp Thr Ser Tyr Ser Gly Ser Lys Thr
        275                 280                 285 cgt ggt gcc gct ggt acc cag tat gac gat agc aat atg ggc cag aac    912
Arg Gly Ala Ala Gly Thr Gln Tyr Asp Asp Ser Asn Met Gly Gln Asn
    290                 295                 300 aaa gtt ggc ctg agc ttc tcg ctg ccg att tat cag ggc gga atg gtt    960
Lys Val Gly Leu Ser Phe Ser Leu Pro Ile Tyr Gln Gly Gly Met Val
305                 310                 315                 320 aac tcg cag gtg aaa cag gca cag tac aac ttt gtt ggt gcc agt gag    1008
Asn Ser Gln Val Lys Gln Ala Gln Tyr Asn Phe Val Gly Ala Ser Glu
                325                 330                 335 caa ctg gaa agc gca cat cgt agc gtc gtg caa acc gta cgt tcc tcc    1056
Gln Leu Glu Ser Ala His Arg Ser Val Val Gln Thr Val Arg Ser Ser
            340                 345                 350 ttc aac aac att aat gct tct atc agt agt att aac gcc tac aaa caa    1104
Phe Asn Asn Ile Asn Ala Ser Ile Ser Ser Ile Asn Ala Tyr Lys Gln
        355                 360                 365 gcc gta gtt tcc gcg caa agc tca tta gac gcg atg gaa gcg ggc tac    1152
Ala Val Val Ser Ala Gln Ser Ser Leu Asp Ala Met Glu Ala Gly Tyr
    370                 375                 380 tcg gtc ggt acg cgt acc att gtt gat gtg ttg gat gcg acc acc acg    1200
Ser Val Gly Thr Arg Thr Ile Val Asp Val Leu Asp Ala Thr Thr Thr
385                 390                 395                 400 ctg tac aac gcc aag caa gag ctg gcg aat gcg cgt tat aac tac ctg    1248
Leu Tyr Asn Ala Lys Gln Glu Leu Ala Asn Ala Arg Tyr Asn Tyr Leu
                405                 410                 415 att aat cag ctg aat att aag tca gcc ctg ggt acg ttg aac gag cag    1296
Ile Asn Gln Leu Asn Ile Lys Ser Ala Leu Gly Thr Leu Asn Glu Gln
            420                 425                 430 gat ttg ctg gca ctg aac aat gcg ctg agc aaa ccg gtt tcc act aat    1344
Asp Leu Leu Ala Leu Asn Asn Ala Leu Ser Lys Pro Val Ser Thr Asn
        435                 440                 445 ccg gaa aac gtt gcc ccg caa acg ccg gaa cag aat gct att gct gat    1392
Pro Glu Asn Val Ala Pro Gln Thr Pro Glu Gln Asn Ala Ile Ala Asp
    450                 455                 460 ggt tat gcg cct gat agc ccg gca ccc gtc gtt cag caa aca tcc gca    1440
Gly Tyr Ala Pro Asp Ser Pro Ala Pro Val Val Gln Gln Thr Ser Ala
465                 470                 475                 480 cgc act acc acc agt aac ggt cat aac cct ttc cgt aac tga             1482
Arg Thr Thr Thr Ser Asn Gly His Asn Pro Phe Arg Asn
                485                 490

<210> SEQ ID NO 14
<211> LENGTH: 493
<212> TYPE: PRT
<213> ORGANISM: Shigella flexneri

<400> SEQUENCE: 14

Met Lys Lys Leu Leu Pro Ile Leu Ile Gly Leu Ser Leu Ser Gly Phe
1               5                   10                  15

Ser Ser Leu Ser Gln Ala Glu Asn Leu Met Gln Val Tyr Gln Gln Ala
            20                  25                  30
```

```
Arg Leu Ser Asn Pro Glu Leu Arg Lys Ser Ala Ala Asp Arg Asp Ala
         35                  40                  45

Ala Phe Glu Lys Ile Asn Glu Ala Arg Ser Pro Leu Leu Pro Gln Leu
 50                  55                  60

Gly Leu Gly Ala Asp Tyr Thr Tyr Ser Asn Gly Tyr Arg Asp Ala Asn
 65                  70                  75                  80

Gly Ile Asn Ser Asn Ala Thr Ser Ala Ser Leu Gln Leu Thr Gln Ser
             85                  90                  95

Ile Phe Asp Met Ser Lys Trp Arg Ala Leu Thr Leu Gln Glu Lys Ala
            100                 105                 110

Ala Gly Ile Gln Asp Val Thr Tyr Gln Thr Asp Gln Gln Thr Leu Ile
            115                 120                 125

Leu Asn Thr Ala Thr Ala Tyr Phe Asn Val Leu Asn Ala Ile Asp Val
130                 135                 140

Leu Ser Tyr Thr Gln Ala Gln Lys Glu Ala Ile Tyr Arg Gln Leu Asp
145                 150                 155                 160

Gln Thr Thr Gln Arg Phe Asn Val Gly Leu Val Ala Ile Thr Asp Val
                165                 170                 175

Gln Asn Ala Arg Ala Gln Tyr Asp Thr Val Leu Ala Asn Glu Val Thr
            180                 185                 190

Ala Arg Asn Asn Leu Asp Asn Ala Val Glu Gln Leu Arg Gln Ile Thr
            195                 200                 205

Gly Asn Tyr Tyr Pro Glu Leu Ala Ala Leu Asn Val Glu Asn Phe Lys
            210                 215                 220

Thr Asp Lys Pro Gln Pro Val Asn Ala Leu Leu Lys Glu Ala Glu Lys
225                 230                 235                 240

Arg Asn Leu Ser Leu Leu Gln Ala Arg Leu Ser Gln Asp Leu Glu Arg
                245                 250                 255

Glu Gln Ile Arg Gln Ala Gln Asp Gly His Leu Pro Thr Leu Asp Leu
            260                 265                 270

Thr Ala Ser Thr Gly Ile Ser Asp Thr Ser Tyr Ser Gly Ser Lys Thr
            275                 280                 285

Arg Gly Ala Ala Gly Thr Gln Tyr Asp Asp Ser Asn Met Gly Gln Asn
            290                 295                 300

Lys Val Gly Leu Ser Phe Ser Leu Pro Ile Tyr Gln Gly Gly Met Val
305                 310                 315                 320

Asn Ser Gln Val Lys Gln Ala Gln Tyr Asn Phe Val Gly Ala Ser Glu
                325                 330                 335

Gln Leu Glu Ser Ala His Arg Ser Val Val Gln Thr Val Arg Ser Ser
            340                 345                 350

Phe Asn Asn Ile Asn Ala Ser Ile Ser Ser Ile Asn Ala Tyr Lys Gln
            355                 360                 365

Ala Val Val Ser Ala Gln Ser Ser Leu Asp Ala Met Glu Ala Gly Tyr
            370                 375                 380

Ser Val Gly Thr Arg Thr Ile Val Asp Val Leu Asp Ala Thr Thr Thr
385                 390                 395                 400

Leu Tyr Asn Ala Lys Gln Glu Leu Ala Asn Ala Arg Tyr Asn Tyr Leu
                405                 410                 415

Ile Asn Gln Leu Asn Ile Lys Ser Ala Leu Gly Thr Leu Asn Glu Gln
            420                 425                 430

Asp Leu Leu Ala Leu Asn Asn Ala Leu Ser Lys Pro Val Ser Thr Asn
            435                 440                 445

Pro Glu Asn Val Ala Pro Gln Thr Pro Glu Gln Asn Ala Ile Ala Asp
```

```
                    450                 455                 460
Gly Tyr Ala Pro Asp Ser Pro Ala Pro Val Val Gln Gln Thr Ser Ala
465                 470                 475                 480

Arg Thr Thr Thr Ser Asn Gly His Asn Pro Phe Arg Asn
                485                 490
```

<210> SEQ ID NO 15
<211> LENGTH: 1476
<212> TYPE: DNA
<213> ORGANISM: Salmonella enterica
<220> FEATURE:
<221> NAME/KEY: CDS
<222> LOCATION: (1)..(1476)

<400> SEQUENCE: 15

```
atg caa atg aag aaa ttg ctc ccc atc ctt atc ggc ctg agc ctg tcg       48
Met Gln Met Lys Lys Leu Leu Pro Ile Leu Ile Gly Leu Ser Leu Ser
1               5                   10                  15 ggg ttc agc aca cta agc cag gca gag aac ctg atg caa gtt tat cag       96
Gly Phe Ser Thr Leu Ser Gln Ala Glu Asn Leu Met Gln Val Tyr Gln
                20                  25                  30 caa gca cgc ctg agc aac ccg gaa ttg cgt aaa tcc gct gcc gat cgc      144
Gln Ala Arg Leu Ser Asn Pro Glu Leu Arg Lys Ser Ala Ala Asp Arg
            35                  40                  45 gat gct gca ttc gaa aaa att aac gaa gca cgt agt cct tta ctg ccg      192
Asp Ala Ala Phe Glu Lys Ile Asn Glu Ala Arg Ser Pro Leu Leu Pro
    50                  55                  60 caa ctg ggt tta ggt gcc gac tac acc tac agc aac ggt tat cgc gat      240
Gln Leu Gly Leu Gly Ala Asp Tyr Thr Tyr Ser Asn Gly Tyr Arg Asp
65                  70                  75                  80 gcg aac ggt atc aac tcc aat gaa acc agc gct tct ctg caa tta acg      288
Ala Asn Gly Ile Asn Ser Asn Glu Thr Ser Ala Ser Leu Gln Leu Thr
                85                  90                  95 cag acg cta ttt gat atg tcg aaa tgg cgt ggg ctc acc ctg caa gaa      336
Gln Thr Leu Phe Asp Met Ser Lys Trp Arg Gly Leu Thr Leu Gln Glu
                100                 105                 110 aaa gca gca ggc att cag gat gtc acc tat cag acc gat cag cag acg      384
Lys Ala Ala Gly Ile Gln Asp Val Thr Tyr Gln Thr Asp Gln Gln Thr
            115                 120                 125 ctg atc ctc aat acc gcg aac gcg tat ttt aag gta ttg aac gct att      432
Leu Ile Leu Asn Thr Ala Asn Ala Tyr Phe Lys Val Leu Asn Ala Ile
    130                 135                 140 gat gtg ctt tcc tat acc cag gcg caa aaa gag gct atc tac cgt cag      480
Asp Val Leu Ser Tyr Thr Gln Ala Gln Lys Glu Ala Ile Tyr Arg Gln
145                 150                 155                 160 tta gat caa acg acg caa cgt ttt aac gtg ggt ctg gtc gcc att acc      528
Leu Asp Gln Thr Thr Gln Arg Phe Asn Val Gly Leu Val Ala Ile Thr
                165                 170                 175 gac gtg caa aac gcc cgt gcg caa tat gat acc gta ctg gcg aat gaa      576
Asp Val Gln Asn Ala Arg Ala Gln Tyr Asp Thr Val Leu Ala Asn Glu
                180                 185                 190 gtg acc gcc cgc aac aac ctg gat aac gcg gta gaa gag ctg cgc cag      624
Val Thr Ala Arg Asn Asn Leu Asp Asn Ala Val Glu Glu Leu Arg Gln
            195                 200                 205 gta acc ggc aat tat tac ccg gag ctg gcg tcg ctt aac gtc gag cat      672
Val Thr Gly Asn Tyr Tyr Pro Glu Leu Ala Ser Leu Asn Val Glu His
    210                 215                 220 ttt aaa acc gac aaa ccc aaa gct gtt aat gcg ctg ctg aag gaa gcg      720
Phe Lys Thr Asp Lys Pro Lys Ala Val Asn Ala Leu Leu Lys Glu Ala
225                 230                 235                 240 gaa aac cgt aac ctg tcg ctg ttg cag gcg cgt tta agt cag gat ctg      768
```

-continued

```
Glu Asn Arg Asn Leu Ser Leu Leu Gln Ala Arg Leu Ser Gln Asp Leu
                245                 250                 255 gcg cgc gag caa atc cgt cag gcg cag gat ggt cat ctg ccg acg ctg      816
Ala Arg Glu Gln Ile Arg Gln Ala Gln Asp Gly His Leu Pro Thr Leu
        260                 265                 270 aat tta acg gcc tca acc ggc att tct gat acc tct tat agc ggt tct      864
Asn Leu Thr Ala Ser Thr Gly Ile Ser Asp Thr Ser Tyr Ser Gly Ser
275                 280                 285 aaa acc aac tcc gcc cag tac gac gat agc aac atg ggg cag aat aaa      912
Lys Thr Asn Ser Ala Gln Tyr Asp Asp Ser Asn Met Gly Gln Asn Lys
    290                 295                 300 atc ggc ctg aac ttc tcc ctg ccg ctg tat caa ggc ggg atg gtt aac      960
Ile Gly Leu Asn Phe Ser Leu Pro Leu Tyr Gln Gly Gly Met Val Asn
305                 310                 315                 320 tcg cag gta aaa cag gcg cag tat aac ttc gtc ggc gca agc gaa cag     1008
Ser Gln Val Lys Gln Ala Gln Tyr Asn Phe Val Gly Ala Ser Glu Gln
                325                 330                 335 ctg gaa agc gcg cac cgt agc gtg gtg cag acc gta cgt tct tcc ttt     1056
Leu Glu Ser Ala His Arg Ser Val Val Gln Thr Val Arg Ser Ser Phe
            340                 345                 350 aac aat att aac gcc tcc atc agc agc atc aac gcg tat aaa cag gca     1104
Asn Asn Ile Asn Ala Ser Ile Ser Ser Ile Asn Ala Tyr Lys Gln Ala
        355                 360                 365 gtc gtt tcc gcg caa agt tct ttg gat gca atg gaa gcc ggt tac tcg     1152
Val Val Ser Ala Gln Ser Ser Leu Asp Ala Met Glu Ala Gly Tyr Ser
370                 375                 380 gtc ggt aca cgt acc att gtt gac gta ctg gat gcc acc act ctg         1200
Val Gly Thr Arg Thr Ile Val Asp Val Leu Asp Ala Thr Thr Leu
385                 390                 395                 400 tat gat gcc aag cag caa ctg gcc aac gcg cgt tat acc tat ttg att     1248
Tyr Asp Ala Lys Gln Gln Leu Ala Asn Ala Arg Tyr Thr Tyr Leu Ile
                405                 410                 415 aat cag tta aat atc aaa tat gcg ctc ggt acg ctg aac gag cag gat     1296
Asn Gln Leu Asn Ile Lys Tyr Ala Leu Gly Thr Leu Asn Glu Gln Asp
            420                 425                 430 ctg ctc gcg ctt aac agt acg ttg ggt aaa cct atc ccg acg tcg ccg     1344
Leu Leu Ala Leu Asn Ser Thr Leu Gly Lys Pro Ile Pro Thr Ser Pro
        435                 440                 445 gaa agc gta gcg ccg gaa acg cca gag cag gat gct gcc gca gac ggt     1392
Glu Ser Val Ala Pro Glu Thr Pro Glu Gln Asp Ala Ala Ala Asp Gly
450                 455                 460 tat aat gcc cat agc gcc gcg ccg gca gta cag ccg acc gcc gct cgc     1440
Tyr Asn Ala His Ser Ala Ala Pro Ala Val Gln Pro Thr Ala Ala Arg
465                 470                 475                 480 gcc aac agc aat aac ggc aat cca ttc cgg cat tga                     1476
Ala Asn Ser Asn Asn Gly Asn Pro Phe Arg His
                485                 490

<210> SEQ ID NO 16
<211> LENGTH: 491
<212> TYPE: PRT
<213> ORGANISM: Salmonella enterica

<400> SEQUENCE: 16

Met Gln Met Lys Lys Leu Leu Pro Ile Leu Ile Gly Leu Ser Leu Ser
1               5                   10                  15

Gly Phe Ser Thr Leu Ser Gln Ala Glu Asn Leu Met Gln Val Tyr Gln
                20                  25                  30

Gln Ala Arg Leu Ser Asn Pro Glu Leu Arg Lys Ser Ala Ala Asp Arg
            35                  40                  45
```

```
Asp Ala Ala Phe Glu Lys Ile Asn Glu Ala Arg Ser Pro Leu Leu Pro
 50                  55                  60

Gln Leu Gly Leu Gly Ala Asp Tyr Thr Tyr Ser Asn Gly Tyr Arg Asp
 65                  70                  75                  80

Ala Asn Gly Ile Asn Ser Asn Glu Thr Ser Ala Ser Leu Gln Leu Thr
                 85                  90                  95

Gln Thr Leu Phe Asp Met Ser Lys Trp Arg Gly Leu Thr Leu Gln Glu
            100                 105                 110

Lys Ala Ala Gly Ile Gln Asp Val Thr Tyr Gln Thr Asp Gln Gln Thr
            115                 120                 125

Leu Ile Leu Asn Thr Ala Asn Ala Tyr Phe Lys Val Leu Asn Ala Ile
       130                 135                 140

Asp Val Leu Ser Tyr Thr Gln Ala Gln Lys Glu Ala Ile Tyr Arg Gln
145                 150                 155                 160

Leu Asp Gln Thr Thr Gln Arg Phe Asn Val Gly Leu Val Ala Ile Thr
                165                 170                 175

Asp Val Gln Asn Ala Arg Ala Gln Tyr Asp Thr Val Leu Ala Asn Glu
            180                 185                 190

Val Thr Ala Arg Asn Asn Leu Asp Asn Ala Val Glu Glu Leu Arg Gln
            195                 200                 205

Val Thr Gly Asn Tyr Tyr Pro Glu Leu Ala Ser Leu Asn Val Glu His
       210                 215                 220

Phe Lys Thr Asp Lys Pro Lys Ala Val Asn Ala Leu Leu Lys Glu Ala
225                 230                 235                 240

Glu Asn Arg Asn Leu Ser Leu Leu Gln Ala Arg Leu Ser Gln Asp Leu
                245                 250                 255

Ala Arg Glu Gln Ile Arg Gln Ala Gln Asp Gly His Leu Pro Thr Leu
            260                 265                 270

Asn Leu Thr Ala Ser Thr Gly Ile Ser Asp Thr Ser Tyr Ser Gly Ser
            275                 280                 285

Lys Thr Asn Ser Ala Gln Tyr Asp Asp Ser Asn Met Gly Gln Asn Lys
       290                 295                 300

Ile Gly Leu Asn Phe Ser Leu Pro Leu Tyr Gln Gly Gly Met Val Asn
305                 310                 315                 320

Ser Gln Val Lys Gln Ala Gln Tyr Asn Phe Val Gly Ala Ser Glu Gln
                325                 330                 335

Leu Glu Ser Ala His Arg Ser Val Val Gln Thr Val Arg Ser Ser Phe
            340                 345                 350

Asn Asn Ile Asn Ala Ser Ile Ser Ile Asn Ala Tyr Lys Gln Ala
            355                 360                 365

Val Val Ser Ala Gln Ser Ser Leu Asp Ala Met Glu Ala Gly Tyr Ser
       370                 375                 380

Val Gly Thr Arg Thr Ile Val Asp Val Leu Asp Ala Thr Thr Thr Leu
385                 390                 395                 400

Tyr Asp Ala Lys Gln Gln Leu Ala Asn Ala Arg Tyr Thr Tyr Leu Ile
                405                 410                 415

Asn Gln Leu Asn Ile Lys Tyr Ala Leu Gly Thr Leu Asn Glu Gln Asp
            420                 425                 430

Leu Leu Ala Leu Asn Ser Thr Leu Gly Lys Pro Ile Pro Thr Ser Pro
            435                 440                 445

Glu Ser Val Ala Pro Glu Thr Pro Glu Gln Asp Ala Ala Asp Gly
       450                 455                 460

Tyr Asn Ala His Ser Ala Ala Pro Ala Val Gln Pro Thr Ala Ala Arg
465                 470                 475                 480
```

```
Ala Asn Ser Asn Asn Gly Asn Pro Phe Arg His
                485                 490

<210> SEQ ID NO 17
<211> LENGTH: 1470
<212> TYPE: DNA
<213> ORGANISM: Citrobacter koseri
<220> FEATURE:
<221> NAME/KEY: CDS
<222> LOCATION: (1)..(1470)

<400> SEQUENCE: 17 atg caa atg aag aaa ttg ctc ccc atc ctt atc ggc ctg agc ctg acg        48
Met Gln Met Lys Lys Leu Leu Pro Ile Leu Ile Gly Leu Ser Leu Thr
1               5                   10                  15 ggg ttc agc aca ctg agc cag gca gag aac ctg atg caa gtt tat cag       96
Gly Phe Ser Thr Leu Ser Gln Ala Glu Asn Leu Met Gln Val Tyr Gln
            20                  25                  30 caa gca cgc ctg agc aac ccg gaa ttg cgt aaa tcc gcc gcc gat cgc      144
Gln Ala Arg Leu Ser Asn Pro Glu Leu Arg Lys Ser Ala Ala Asp Arg
        35                  40                  45 gat gct gca ttc gaa aaa att aac gaa gcg cgt agt cct tta ctg ccg      192
Asp Ala Ala Phe Glu Lys Ile Asn Glu Ala Arg Ser Pro Leu Leu Pro
    50                  55                  60 caa ctg ggt tta ggt gcc gat tac acc tac agc aac ggc tat cgt gat      240
Gln Leu Gly Leu Gly Ala Asp Tyr Thr Tyr Ser Asn Gly Tyr Arg Asp
65                  70                  75                  80 gcg aat ggc atc aac tcc aac gcc acc agc gcc tct ctg caa tta acc      288
Ala Asn Gly Ile Asn Ser Asn Ala Thr Ser Ala Ser Leu Gln Leu Thr
                85                  90                  95 cag acc ctt ttt gat atg tca aaa tgg cgc gcg ctg acg ttg cag gaa      336
Gln Thr Leu Phe Asp Met Ser Lys Trp Arg Ala Leu Thr Leu Gln Glu
            100                 105                 110 aaa tcc gca ggt atc cag gac gtc acg ttc cag acc gat cag caa acg      384
Lys Ser Ala Gly Ile Gln Asp Val Thr Phe Gln Thr Asp Gln Gln Thr
        115                 120                 125 ctg atc ctc aat acg gcg agc gcc tac ttt aaa gtc ctg aac gcc att      432
Leu Ile Leu Asn Thr Ala Ser Ala Tyr Phe Lys Val Leu Asn Ala Ile
    130                 135                 140 gac gtt ctc tct tat acg cag gcg cag aaa gaa gcc gtt tat cgt cag      480
Asp Val Leu Ser Tyr Thr Gln Ala Gln Lys Glu Ala Val Tyr Arg Gln
145                 150                 155                 160 tta gat caa acc acc cag cgt ttt aac gtc ggc ctg gtc gct atc act      528
Leu Asp Gln Thr Thr Gln Arg Phe Asn Val Gly Leu Val Ala Ile Thr
                165                 170                 175 gac gtg caa aac gcc cgt gca caa tac gat acc gtg ctg gcg aac gaa      576
Asp Val Gln Asn Ala Arg Ala Gln Tyr Asp Thr Val Leu Ala Asn Glu
            180                 185                 190 gtc acc gcc cgc aac aat ctg gat aac gcc gta gaa gaa ctg cgc cag      624
Val Thr Ala Arg Asn Asn Leu Asp Asn Ala Val Glu Glu Leu Arg Gln
        195                 200                 205 gtc acc ggt aac tac tac ccg gaa ctg gct tcg ctg aat gtc aca aac      672
Val Thr Gly Asn Tyr Tyr Pro Glu Leu Ala Ser Leu Asn Val Thr Asn
    210                 215                 220 ttt aaa acc gac aag ccg cag gcc gtt aac gcg ctg ctg aaa gag gcc      720
Phe Lys Thr Asp Lys Pro Gln Ala Val Asn Ala Leu Leu Lys Glu Ala
225                 230                 235                 240 gaa aac cgt aac ctg acg ctg ttg cag gcg cgt ctg agc cag gat ctg      768
Glu Asn Arg Asn Leu Thr Leu Leu Gln Ala Arg Leu Ser Gln Asp Leu
                245                 250                 255 gcg cgc gag caa atc cgc cag gcg cag gac ggc cat ctg cca acg ctg      816
```

```
                Ala Arg Glu Gln Ile Arg Gln Ala Gln Asp Gly His Leu Pro Thr Leu
                            260                 265                 270 gat tta acc gcc tct acc ggc gtg tct gac acc tct tat agc ggc tct       864
Asp Leu Thr Ala Ser Thr Gly Val Ser Asp Thr Ser Tyr Ser Gly Ser
            275                 280                 285 aaa acc cat aac agc acg cag tat gac gac agc aat atg ggc cag aac       912
Lys Thr His Asn Ser Thr Gln Tyr Asp Asp Ser Asn Met Gly Gln Asn
        290                 295                 300 aaa atc ggc ctg agc ttc tcg ctg ccg ctg tat cag ggt ggg atg gtc       960
Lys Ile Gly Leu Ser Phe Ser Leu Pro Leu Tyr Gln Gly Gly Met Val
305                 310                 315                 320 aac tct cag gtg aaa cag gcg cag tac aac ttt gtt ggc gcg agc gaa      1008
Asn Ser Gln Val Lys Gln Ala Gln Tyr Asn Phe Val Gly Ala Ser Glu
                325                 330                 335 cag ctg gaa agc gcg cac cgc agc gtc gtg cag act gtg cgc tct tcc      1056
Gln Leu Glu Ser Ala His Arg Ser Val Val Gln Thr Val Arg Ser Ser
            340                 345                 350 ttc aac aac att aat gct tct atc agc agc atc aac gct tac aaa cag      1104
Phe Asn Asn Ile Asn Ala Ser Ile Ser Ser Ile Asn Ala Tyr Lys Gln
        355                 360                 365 gcc gtt gtt tcc gcg caa agc tct ttg gat gca aac gaa gcc ggt tat      1152
Ala Val Val Ser Ala Gln Ser Ser Leu Asp Ala Asn Glu Ala Gly Tyr
370                 375                 380 tcc gtg ggt acg cgt acc att gtt gac gtg ctg gat gcc acc acc gcg      1200
Ser Val Gly Thr Arg Thr Ile Val Asp Val Leu Asp Ala Thr Thr Ala
385                 390                 395                 400 ctg tat gaa gcg aag caa caa ctg gcg aat gcg cgt tat aac tat ctg      1248
Leu Tyr Glu Ala Lys Gln Gln Leu Ala Asn Ala Arg Tyr Asn Tyr Leu
                405                 410                 415 att aac cag ctg aac atc aag aat gct ctc ggt acg ttg aac gag cag      1296
Ile Asn Gln Leu Asn Ile Lys Asn Ala Leu Gly Thr Leu Asn Glu Gln
            420                 425                 430 gat ctg gtg gcg ctg aac aat gcg ctg ggt aaa ccg atc tcg aca tcc      1344
Asp Leu Val Ala Leu Asn Asn Ala Leu Gly Lys Pro Ile Ser Thr Ser
        435                 440                 445 ccg gac aac gtc gcg ccg gaa acc ccg cag cag gat gca gcg gcg gat      1392
Pro Asp Asn Val Ala Pro Glu Thr Pro Gln Gln Asp Ala Ala Ala Asp
450                 455                 460 ggc tat aat gcc agt acg gtt cag cct gct tca gca cgt tcc acc agc      1440
Gly Tyr Asn Ala Ser Thr Val Gln Pro Ala Ser Ala Arg Ser Thr Ser
465                 470                 475                 480 agc aac ggt aac aac ccg ttc cgt aac tga                              1470
Ser Asn Gly Asn Asn Pro Phe Arg Asn
                485

<210> SEQ ID NO 18
<211> LENGTH: 489
<212> TYPE: PRT
<213> ORGANISM: Citrobacter koseri

<400> SEQUENCE: 18

Met Gln Met Lys Lys Leu Leu Pro Ile Leu Ile Gly Leu Ser Leu Thr
1               5                   10                  15

Gly Phe Ser Thr Leu Ser Gln Ala Glu Asn Leu Met Gln Val Tyr Gln
                20                  25                  30

Gln Ala Arg Leu Ser Asn Pro Glu Leu Arg Lys Ser Ala Ala Asp Arg
            35                  40                  45

Asp Ala Ala Phe Glu Lys Ile Asn Glu Ala Arg Ser Pro Leu Leu Pro
        50                  55                  60

Gln Leu Gly Leu Gly Ala Asp Tyr Thr Tyr Ser Asn Gly Tyr Arg Asp
```

-continued

```
                65                  70                  75                  80
Ala Asn Gly Ile Asn Ser Asn Ala Thr Ser Ala Ser Leu Gln Leu Thr
                        85                  90                  95
Gln Thr Leu Phe Asp Met Ser Lys Trp Arg Ala Leu Thr Leu Gln Glu
                100                 105                 110
Lys Ser Ala Gly Ile Gln Asp Val Thr Phe Gln Thr Asp Gln Gln Thr
                115                 120                 125
Leu Ile Leu Asn Thr Ala Ser Ala Tyr Phe Lys Val Leu Asn Ala Ile
            130                 135                 140
Asp Val Leu Ser Tyr Thr Gln Ala Gln Lys Glu Ala Val Tyr Arg Gln
145                 150                 155                 160
Leu Asp Gln Thr Thr Gln Arg Phe Asn Val Gly Leu Val Ala Ile Thr
                165                 170                 175
Asp Val Gln Asn Ala Arg Ala Gln Tyr Asp Thr Val Leu Ala Asn Glu
                180                 185                 190
Val Thr Ala Arg Asn Asn Leu Asp Asn Ala Val Glu Glu Leu Arg Gln
                195                 200                 205
Val Thr Gly Asn Tyr Tyr Pro Glu Leu Ala Ser Leu Asn Val Thr Asn
    210                 215                 220
Phe Lys Thr Asp Lys Pro Gln Ala Val Asn Ala Leu Leu Lys Glu Ala
225                 230                 235                 240
Glu Asn Arg Asn Leu Thr Leu Leu Gln Ala Arg Leu Ser Gln Asp Leu
                245                 250                 255
Ala Arg Glu Gln Ile Arg Gln Ala Gln Asp Gly His Leu Pro Thr Leu
                260                 265                 270
Asp Leu Thr Ala Ser Thr Gly Val Ser Asp Thr Ser Tyr Ser Gly Ser
            275                 280                 285
Lys Thr His Asn Ser Thr Gln Tyr Asp Asp Ser Asn Met Gly Gln Asn
            290                 295                 300
Lys Ile Gly Leu Ser Phe Ser Leu Pro Leu Tyr Gln Gly Gly Met Val
305                 310                 315                 320
Asn Ser Gln Val Lys Gln Ala Gln Tyr Asn Phe Val Gly Ala Ser Glu
                325                 330                 335
Gln Leu Glu Ser Ala His Arg Ser Val Val Gln Thr Val Arg Ser Ser
                340                 345                 350
Phe Asn Asn Ile Asn Ala Ser Ile Ser Ser Ile Asn Ala Tyr Lys Gln
            355                 360                 365
Ala Val Val Ser Ala Gln Ser Ser Leu Asp Ala Asn Glu Ala Gly Tyr
            370                 375                 380
Ser Val Gly Thr Arg Thr Ile Val Asp Val Leu Asp Ala Thr Thr Ala
385                 390                 395                 400
Leu Tyr Glu Ala Lys Gln Gln Leu Ala Asn Ala Arg Tyr Asn Tyr Leu
                405                 410                 415
Ile Asn Gln Leu Asn Ile Lys Asn Ala Leu Gly Thr Leu Asn Glu Gln
                420                 425                 430
Asp Leu Val Ala Leu Asn Asn Ala Leu Gly Lys Pro Ile Ser Thr Ser
                435                 440                 445
Pro Asp Asn Val Ala Pro Glu Thr Pro Gln Gln Asp Ala Ala Ala Asp
    450                 455                 460
Gly Tyr Asn Ala Ser Thr Val Gln Pro Ala Ser Ala Arg Ser Thr Ser
465                 470                 475                 480
Ser Asn Gly Asn Asn Pro Phe Arg Asn
                485
```

<210> SEQ ID NO 19
<211> LENGTH: 1479
<212> TYPE: DNA
<213> ORGANISM: Klebsiella pneumoniae
<220> FEATURE:
<221> NAME/KEY: CDS
<222> LOCATION: (1)..(1479)

<400> SEQUENCE: 19

| | | | | | | | | | | | | | | | | |
|---|---|---|---|---|---|---|---|---|---|---|---|---|---|---|---|---|
| atg | caa | atg | aag | aaa | ttg | ctc | ccc | att | ctt | atc | ggc | ctg | agc | ctg | acc | 48 |
| Met | Gln | Met | Lys | Lys | Leu | Leu | Pro | Ile | Leu | Ile | Gly | Leu | Ser | Leu | Thr | |
| 1 | | | | 5 | | | | | 10 | | | | | 15 | | |
| ggg | ttc | agc | gcc | atg | agc | cag | gcg | gaa | aac | ctg | ctt | cag | gtt | tac | cag | 96 |
| Gly | Phe | Ser | Ala | Met | Ser | Gln | Ala | Glu | Asn | Leu | Leu | Gln | Val | Tyr | Gln | |
| | | | 20 | | | | | 25 | | | | | 30 | | | |
| cag | gca | cgc | atc | agc | aac | ccc | gat | ctg | cgt | aaa | tcg | gca | gcc | gat | cgt | 144 |
| Gln | Ala | Arg | Ile | Ser | Asn | Pro | Asp | Leu | Arg | Lys | Ser | Ala | Ala | Asp | Arg | |
| | | 35 | | | | | 40 | | | | | 45 | | | | |
| gac | gcc | gcg | ttc | gaa | aag | atc | aac | gaa | gcg | cgc | agt | cca | tta | ctg | cct | 192 |
| Asp | Ala | Ala | Phe | Glu | Lys | Ile | Asn | Glu | Ala | Arg | Ser | Pro | Leu | Leu | Pro | |
| | 50 | | | | | 55 | | | | | 60 | | | | | |
| cag | ctt | ggg | ctg | gga | gcg | gat | tat | acc | tat | aac | aat | ggc | tat | cgc | gac | 240 |
| Gln | Leu | Gly | Leu | Gly | Ala | Asp | Tyr | Thr | Tyr | Asn | Asn | Gly | Tyr | Arg | Asp | |
| 65 | | | | | 70 | | | | | 75 | | | | | 80 | |
| agc | aac | ggc | atc | aat | tca | aac | gtc | acc | agc | ggc | tcg | ctg | cag | tta | acg | 288 |
| Ser | Asn | Gly | Ile | Asn | Ser | Asn | Val | Thr | Ser | Gly | Ser | Leu | Gln | Leu | Thr | |
| | | | | 85 | | | | | 90 | | | | | 95 | | |
| cag | gtt | ctg | ttt | gat | atg | tcg | aaa | tgg | cgc | gcc | ctg | acg | ctg | cag | gaa | 336 |
| Gln | Val | Leu | Phe | Asp | Met | Ser | Lys | Trp | Arg | Ala | Leu | Thr | Leu | Gln | Glu | |
| | | | 100 | | | | | 105 | | | | | 110 | | | |
| aaa | acg | gca | ggg | att | cag | gat | gtc | acg | tat | cag | acc | gat | cag | caa | aca | 384 |
| Lys | Thr | Ala | Gly | Ile | Gln | Asp | Val | Thr | Tyr | Gln | Thr | Asp | Gln | Gln | Thr | |
| | | 115 | | | | | 120 | | | | | 125 | | | | |
| ctg | att | ctg | aat | acc | gcg | acg | gcc | tat | ttt | aaa | gtg | ctg | gcc | gcc | atc | 432 |
| Leu | Ile | Leu | Asn | Thr | Ala | Thr | Ala | Tyr | Phe | Lys | Val | Leu | Ala | Ala | Ile | |
| | 130 | | | | | 135 | | | | | 140 | | | | | |
| gac | acg | ctt | tcc | tat | acc | gaa | gcg | cag | aaa | cag | gct | att | tac | cgc | cag | 480 |
| Asp | Thr | Leu | Ser | Tyr | Thr | Glu | Ala | Gln | Lys | Gln | Ala | Ile | Tyr | Arg | Gln | |
| 145 | | | | | 150 | | | | | 155 | | | | | 160 | |
| ttg | gat | caa | acc | acg | cag | cgc | ttt | aac | gta | ggc | ctg | gtg | gcg | atc | acc | 528 |
| Leu | Asp | Gln | Thr | Thr | Gln | Arg | Phe | Asn | Val | Gly | Leu | Val | Ala | Ile | Thr | |
| | | | | 165 | | | | | 170 | | | | | 175 | | |
| gac | gtg | cag | aac | gcc | cgt | tca | caa | tac | gat | gcc | gtg | ctg | gcg | aac | gaa | 576 |
| Asp | Val | Gln | Asn | Ala | Arg | Ser | Gln | Tyr | Asp | Ala | Val | Leu | Ala | Asn | Glu | |
| | | | 180 | | | | | 185 | | | | | 190 | | | |
| gtc | acc | gcg | cgt | aac | gat | ctc | gac | aac | gcc | gtc | gaa | gaa | ctg | cgt | cag | 624 |
| Val | Thr | Ala | Arg | Asn | Asp | Leu | Asp | Asn | Ala | Val | Glu | Glu | Leu | Arg | Gln | |
| | | 195 | | | | | 200 | | | | | 205 | | | | |
| gtc | acc | ggt | aat | tac | tat | ccg | gag | ctg | gcc | tcc | ctg | aac | gtg | aat | ggc | 672 |
| Val | Thr | Gly | Asn | Tyr | Tyr | Pro | Glu | Leu | Ala | Ser | Leu | Asn | Val | Asn | Gly | |
| | 210 | | | | | 215 | | | | | 220 | | | | | |
| ttc | aaa | acc | aac | aag | ccg | cag | gcg | gtc | aac | gcc | ctg | ctg | aag | gaa | gcg | 720 |
| Phe | Lys | Thr | Asn | Lys | Pro | Gln | Ala | Val | Asn | Ala | Leu | Leu | Lys | Glu | Ala | |
| 225 | | | | | 230 | | | | | 235 | | | | | 240 | |
| gag | aac | cgc | aac | ctg | tcg | ctg | ctg | cag | gcg | cgt | ctg | aac | cag | gac | ctg | 768 |
| Glu | Asn | Arg | Asn | Leu | Ser | Leu | Leu | Gln | Ala | Arg | Leu | Asn | Gln | Asp | Leu | |
| | | | | 245 | | | | | 250 | | | | | 255 | | |
| gct | cgc | gag | cag | att | cgc | cag | gcg | cag | gac | ggc | cat | ttg | ccg | acg | ctc | 816 |
| Ala | Arg | Glu | Gln | Ile | Arg | Gln | Ala | Gln | Asp | Gly | His | Leu | Pro | Thr | Leu | |
| | | | 260 | | | | | 265 | | | | | 270 | | | |
| agc | cta | tcc | gcg | tcg | agt | ggg | ata | tcg | aat | act | agc | tac | agt | ggt | tca | 864 |

```
Ser Leu Ser Ala Ser Ser Gly Ile Ser Asn Thr Ser Tyr Ser Gly Ser
        275                 280                 285 aaa acc cat aat aat cct cag caa tac cag gat aac gat gcc ggg cag      912
Lys Thr His Asn Asn Pro Gln Gln Tyr Gln Asp Asn Asp Ala Gly Gln
    290                 295                 300 aac caa atc ggc ctg aac ttc tct ctg cca ctg tat cag ggc ggc gcg      960
Asn Gln Ile Gly Leu Asn Phe Ser Leu Pro Leu Tyr Gln Gly Gly Ala
305                 310                 315                 320 gtg acc tcg cag gtc aaa cag gcg caa tac aac ttc gtc ggc gcc agc     1008
Val Thr Ser Gln Val Lys Gln Ala Gln Tyr Asn Phe Val Gly Ala Ser
                325                 330                 335 gag cag ctg gaa agc gcc cac cgc agc gtc gtg cag act gtg cgt tca     1056
Glu Gln Leu Glu Ser Ala His Arg Ser Val Val Gln Thr Val Arg Ser
            340                 345                 350 tcg ttt aac aac gtg aac gcc tcc atc agc agc atc aac gcc tac aaa     1104
Ser Phe Asn Asn Val Asn Ala Ser Ile Ser Ser Ile Asn Ala Tyr Lys
        355                 360                 365 cag gcg gtg gtc tct gcg caa agc tcc ctg gat gcc atg gaa gct ggc     1152
Gln Ala Val Val Ser Ala Gln Ser Ser Leu Asp Ala Met Glu Ala Gly
    370                 375                 380 tac tcg gtg ggt acg cgt act atc gtt gac gtc ctc gac gcc acc act     1200
Tyr Ser Val Gly Thr Arg Thr Ile Val Asp Val Leu Asp Ala Thr Thr
385                 390                 395                 400 acg ctg tat aac gct aag cag cag ctc tcg aat gcg cgc tac aac tac     1248
Thr Leu Tyr Asn Ala Lys Gln Gln Leu Ser Asn Ala Arg Tyr Asn Tyr
                405                 410                 415 ctg atc aac gag ctg aac att aag tcg gcg tta ggt acc ctg aac gag     1296
Leu Ile Asn Glu Leu Asn Ile Lys Ser Ala Leu Gly Thr Leu Asn Glu
            420                 425                 430 cag gat ctg gtc gcc ctg aac aac acg ctg ggt aaa ccc atc tcc acc     1344
Gln Asp Leu Val Ala Leu Asn Asn Thr Leu Gly Lys Pro Ile Ser Thr
        435                 440                 445 tcc gca gat agc gtc gcg ccg gaa aat ccg caa cag gat gcc acc gct     1392
Ser Ala Asp Ser Val Ala Pro Glu Asn Pro Gln Gln Asp Ala Thr Ala
    450                 455                 460 gat ggc tac ggc aac act acc gcg gcg gtg aag ccg gcg tcc gca cgg     1440
Asp Gly Tyr Gly Asn Thr Thr Ala Ala Val Lys Pro Ala Ser Ala Arg
465                 470                 475                 480 acc acc cag agc agc ggc agc aat ccg ttc cgt cag taa                 1479
Thr Thr Gln Ser Ser Gly Ser Asn Pro Phe Arg Gln
                485                 490

<210> SEQ ID NO 20
<211> LENGTH: 492
<212> TYPE: PRT
<213> ORGANISM: Klebsiella pneumoniae

<400> SEQUENCE: 20

Met Gln Met Lys Lys Leu Leu Pro Ile Leu Ile Gly Leu Ser Leu Thr
1               5                   10                  15

Gly Phe Ser Ala Met Ser Gln Ala Glu Asn Leu Leu Gln Val Tyr Gln
                20                  25                  30

Gln Ala Arg Ile Ser Asn Pro Asp Leu Arg Lys Ser Ala Ala Asp Arg
            35                  40                  45

Asp Ala Ala Phe Glu Lys Ile Asn Glu Ala Arg Ser Pro Leu Leu Pro
        50                  55                  60

Gln Leu Gly Leu Gly Ala Asp Tyr Thr Tyr Asn Asn Gly Tyr Arg Asp
65                  70                  75                  80

Ser Asn Gly Ile Asn Ser Asn Val Thr Ser Gly Ser Leu Gln Leu Thr
                85                  90                  95
```

```
Gln Val Leu Phe Asp Met Ser Lys Trp Arg Ala Leu Thr Leu Gln Glu
                100                 105                 110

Lys Thr Ala Gly Ile Gln Asp Val Thr Tyr Gln Thr Asp Gln Gln Thr
            115                 120                 125

Leu Ile Leu Asn Thr Ala Thr Ala Tyr Phe Lys Val Leu Ala Ala Ile
        130                 135                 140

Asp Thr Leu Ser Tyr Thr Glu Ala Gln Lys Gln Ala Ile Tyr Arg Gln
145                 150                 155                 160

Leu Asp Gln Thr Thr Gln Arg Phe Asn Val Gly Leu Val Ala Ile Thr
                165                 170                 175

Asp Val Gln Asn Ala Arg Ser Gln Tyr Asp Ala Val Leu Ala Asn Glu
            180                 185                 190

Val Thr Ala Arg Asn Asp Leu Asp Asn Ala Val Glu Glu Leu Arg Gln
        195                 200                 205

Val Thr Gly Asn Tyr Tyr Pro Glu Leu Ala Ser Leu Asn Val Asn Gly
210                 215                 220

Phe Lys Thr Asn Lys Pro Gln Ala Val Asn Ala Leu Leu Lys Glu Ala
225                 230                 235                 240

Glu Asn Arg Asn Leu Ser Leu Leu Gln Ala Arg Leu Asn Gln Asp Leu
                245                 250                 255

Ala Arg Glu Gln Ile Arg Gln Ala Gln Asp Gly His Leu Pro Thr Leu
            260                 265                 270

Ser Leu Ser Ala Ser Ser Gly Ile Ser Asn Thr Ser Tyr Ser Gly Ser
        275                 280                 285

Lys Thr His Asn Asn Pro Gln Gln Tyr Gln Asp Asn Asp Ala Gly Gln
290                 295                 300

Asn Gln Ile Gly Leu Asn Phe Ser Leu Pro Leu Tyr Gln Gly Gly Ala
305                 310                 315                 320

Val Thr Ser Gln Val Lys Gln Ala Gln Tyr Asn Phe Val Gly Ala Ser
                325                 330                 335

Glu Gln Leu Glu Ser Ala His Arg Ser Val Val Gln Thr Val Arg Ser
            340                 345                 350

Ser Phe Asn Asn Val Asn Ala Ser Ile Ser Ser Ile Asn Ala Tyr Lys
        355                 360                 365

Gln Ala Val Val Ser Ala Gln Ser Ser Leu Asp Ala Met Glu Ala Gly
370                 375                 380

Tyr Ser Val Gly Thr Arg Thr Ile Val Asp Val Leu Asp Ala Thr Thr
385                 390                 395                 400

Thr Leu Tyr Asn Ala Lys Gln Gln Leu Ser Asn Ala Arg Tyr Asn Tyr
                405                 410                 415

Leu Ile Asn Glu Leu Asn Ile Lys Ser Ala Leu Gly Thr Leu Asn Glu
            420                 425                 430

Gln Asp Leu Val Ala Leu Asn Asn Thr Leu Gly Lys Pro Ile Ser Thr
        435                 440                 445

Ser Ala Asp Ser Val Ala Pro Glu Asn Pro Gln Gln Asp Ala Thr Ala
450                 455                 460

Asp Gly Tyr Gly Asn Thr Thr Ala Ala Val Lys Pro Ala Ser Ala Arg
465                 470                 475                 480

Thr Thr Gln Ser Ser Gly Ser Asn Pro Phe Arg Gln
                485                 490

<210> SEQ ID NO 21
<211> LENGTH: 1494
<212> TYPE: DNA
```

-continued

```
<213> ORGANISM: Enterobacter sakazakii
<220> FEATURE:
<221> NAME/KEY: CDS
<222> LOCATION: (1)..(1494)

<400> SEQUENCE: 21 atg caa atg aag aaa ctg ctc ccc atc ctt atc ggc ctg agc ctg acg        48
Met Gln Met Lys Lys Leu Leu Pro Ile Leu Ile Gly Leu Ser Leu Thr
1               5                   10                  15 ggc ttc agc gcc atg agc cag gca gaa aac ctg ttg cag gtt tac cag        96
Gly Phe Ser Ala Met Ser Gln Ala Glu Asn Leu Leu Gln Val Tyr Gln
                20                  25                  30 cag gca cgt tta agt aac ccg gac ctg cgc agc tcc gct gct gac cgc       144
Gln Ala Arg Leu Ser Asn Pro Asp Leu Arg Ser Ser Ala Ala Asp Arg
            35                  40                  45 gac gcc gca ttc gaa aaa att aac gaa gcc cgc agt cct tta ctt ccg       192
Asp Ala Ala Phe Glu Lys Ile Asn Glu Ala Arg Ser Pro Leu Leu Pro
        50                  55                  60 cag ctc ggc ctg ggt gca gat tac acc tat aac agc ggt ttt cgc gat       240
Gln Leu Gly Leu Gly Ala Asp Tyr Thr Tyr Asn Ser Gly Phe Arg Asp
65                  70                  75                  80 aac gac ggc gta gac agc act gcc aag agc gcg tcg ctg caa tta acg       288
Asn Asp Gly Val Asp Ser Thr Ala Lys Ser Ala Ser Leu Gln Leu Thr
                85                  90                  95 cag acc att ttc gat atg tcc aaa tgg cgc gcc ctg acc ctg cag gaa       336
Gln Thr Ile Phe Asp Met Ser Lys Trp Arg Ala Leu Thr Leu Gln Glu
                100                 105                 110 aaa acc gca ggc att cag gat gtg acc tac cag acc gat cag cag acg       384
Lys Thr Ala Gly Ile Gln Asp Val Thr Tyr Gln Thr Asp Gln Gln Thr
            115                 120                 125 ctg atg ctg aac act gcg aca gct tat ttc cag gtg ctg agc gcg att       432
Leu Met Leu Asn Thr Ala Thr Ala Tyr Phe Gln Val Leu Ser Ala Ile
        130                 135                 140 gac gcg ctc tcc tac acc gaa gcg cag aaa cag gcg atc tac cgc cag       480
Asp Ala Leu Ser Tyr Thr Glu Ala Gln Lys Gln Ala Ile Tyr Arg Gln
145                 150                 155                 160 ctc gat caa acc acc cag cgt ttt aac gtg ggc ctg gta gcg att acc       528
Leu Asp Gln Thr Thr Gln Arg Phe Asn Val Gly Leu Val Ala Ile Thr
                165                 170                 175 gac gtg cag aac gcc cgc gcg cag tac gat aac gtg ctc gcg aac gaa       576
Asp Val Gln Asn Ala Arg Ala Gln Tyr Asp Asn Val Leu Ala Asn Glu
                180                 185                 190 gtg acc gcg cgt aac aac ctc gac aac gcg ctg gaa cag ctg cgc cag       624
Val Thr Ala Arg Asn Asn Leu Asp Asn Ala Leu Glu Gln Leu Arg Gln
            195                 200                 205 gtg acg ggc aac tac tac ccg cag ctc gcg tcg ctg aac gtc gat aat       672
Val Thr Gly Asn Tyr Tyr Pro Gln Leu Ala Ser Leu Asn Val Asp Asn
        210                 215                 220 ttc aaa acc acc aaa ccg gcc gcc gtt aac gcg ctg ctg aaa gag gca       720
Phe Lys Thr Thr Lys Pro Ala Ala Val Asn Ala Leu Leu Lys Glu Ala
225                 230                 235                 240 gaa cag cgt aac ctg acg ctg ctg cag gcg cgt ctg agc cag gat ctg       768
Glu Gln Arg Asn Leu Thr Leu Leu Gln Ala Arg Leu Ser Gln Asp Leu
                245                 250                 255 gcg cgt gag cag atc cgc tac gct gaa acc ggc cat atg ccg acg ctc       816
Ala Arg Glu Gln Ile Arg Tyr Ala Glu Thr Gly His Met Pro Thr Leu
                260                 265                 270 ggc tta acg gcg tcc agc agc gtg tcg gac acc gac tac agc ggc agc       864
Gly Leu Thr Ala Ser Ser Ser Val Ser Asp Thr Asp Tyr Ser Gly Ser
            275                 280                 285 aaa acc agc ggc gcg gcg gca agc cgt tac gct gac agc aaa atc ggc       912
Lys Thr Ser Gly Ala Ala Ala Ser Arg Tyr Ala Asp Ser Lys Ile Gly
```

```
                                                        -continued

Lys Thr Ser Gly Ala Ala Ser Arg Tyr Ala Asp Ser Lys Ile Gly
    290             295             300 cag aac tcc atc ggc ctg agc ttc aac ctg ccg ctc tac agc ggc ggc       960
Gln Asn Ser Ile Gly Leu Ser Phe Asn Leu Pro Leu Tyr Ser Gly Gly
305             310             315             320 tcg gtg aca tca caa gtt aaa caa gcg cag tac agc ttc gtg ggt gcc      1008
Ser Val Thr Ser Gln Val Lys Gln Ala Gln Tyr Ser Phe Val Gly Ala
            325             330             335 agc gaa aaa ctg gaa agc gcg cac cgc aac gtc gtg cag acc gtg cgt      1056
Ser Glu Lys Leu Glu Ser Ala His Arg Asn Val Val Gln Thr Val Arg
        340             345             350 tcg tct tat aac aac gtt aac gcc tcc atc agc agc atc aaa gcc tat      1104
Ser Ser Tyr Asn Asn Val Asn Ala Ser Ile Ser Ser Ile Lys Ala Tyr
            355             360             365 gag cag gcg gtc gtg tcc gcg caa agc tca ctg gat gcg atg gaa gcc      1152
Glu Gln Ala Val Val Ser Ala Gln Ser Ser Leu Asp Ala Met Glu Ala
    370             375             380 ggt tac tcg gtc ggt acg cgt acc atc gtc gat gtg ctc gac gcc acc      1200
Gly Tyr Ser Val Gly Thr Arg Thr Ile Val Asp Val Leu Asp Ala Thr
385             390             395             400 acc acg ctg tac aac gcc aaa cag cag ctc tcc agc gcg cgt tat aac      1248
Thr Thr Leu Tyr Asn Ala Lys Gln Gln Leu Ser Ser Ala Arg Tyr Asn
            405             410             415 tac ctg atc aac cag ctc aat att aaa tct gcg ctg ggt acg ctc aac      1296
Tyr Leu Ile Asn Gln Leu Asn Ile Lys Ser Ala Leu Gly Thr Leu Asn
        420             425             430 gag cag gat ctg gtc gcg ctg aat aac tcg ctg ggc aaa ccg gtc tct      1344
Glu Gln Asp Leu Val Ala Leu Asn Asn Ser Leu Gly Lys Pro Val Ser
    435             440             445 acc gcg cct gaa agc gtc gcc ccg gaa aac ccg gag cag gac gcc gcc      1392
Thr Ala Pro Glu Ser Val Ala Pro Glu Asn Pro Glu Gln Asp Ala Ala
450             455             460 gtg aat aac atg gcg aac ggc ggc aat gcg cct gcc atg cag cct           1440
Val Asn Asn Met Ala Asn Gly Gly Asn Ala Pro Ala Met Gln Pro
465             470             475             480 gcc gcg gcc acc cgt agc agc aac agc aac agc ggc aac ccg ttc cgt      1488
Ala Ala Ala Thr Arg Ser Ser Asn Ser Asn Ser Gly Asn Pro Phe Arg
            485             490             495 cag taa                                                               1494
Gln

<210> SEQ ID NO 22
<211> LENGTH: 497
<212> TYPE: PRT
<213> ORGANISM: Enterobacter sakazakii

<400> SEQUENCE: 22

Met Gln Met Lys Lys Leu Leu Pro Ile Leu Ile Gly Leu Ser Leu Thr
1               5                   10                  15

Gly Phe Ser Ala Met Ser Gln Ala Glu Asn Leu Leu Gln Val Tyr Gln
            20                  25                  30

Gln Ala Arg Leu Ser Asn Pro Asp Leu Arg Ser Ser Ala Ala Asp Arg
        35                  40                  45

Asp Ala Ala Phe Glu Lys Ile Asn Glu Ala Arg Ser Pro Leu Leu Pro
    50                  55                  60

Gln Leu Gly Leu Gly Ala Asp Tyr Thr Tyr Asn Ser Gly Phe Arg Asp
65                  70                  75                  80

Asn Asp Gly Val Asp Ser Thr Ala Lys Ser Ala Ser Leu Gln Leu Thr
                85                  90                  95
```

-continued

```
Gln Thr Ile Phe Asp Met Ser Lys Trp Arg Ala Leu Thr Leu Gln Glu
                100                 105                 110
Lys Thr Ala Gly Ile Gln Asp Val Thr Tyr Gln Thr Asp Gln Gln Thr
            115                 120                 125
Leu Met Leu Asn Thr Ala Thr Ala Tyr Phe Gln Val Leu Ser Ala Ile
130                 135                 140
Asp Ala Leu Ser Tyr Thr Glu Ala Gln Lys Gln Ala Ile Tyr Arg Gln
145                 150                 155                 160
Leu Asp Gln Thr Thr Gln Arg Phe Asn Val Gly Leu Val Ala Ile Thr
                165                 170                 175
Asp Val Gln Asn Ala Arg Ala Gln Tyr Asp Asn Val Leu Ala Asn Glu
            180                 185                 190
Val Thr Ala Arg Asn Asn Leu Asp Asn Ala Leu Glu Gln Leu Arg Gln
        195                 200                 205
Val Thr Gly Asn Tyr Tyr Pro Gln Leu Ala Ser Leu Asn Val Asp Asn
    210                 215                 220
Phe Lys Thr Thr Lys Pro Ala Ala Val Asn Ala Leu Leu Lys Glu Ala
225                 230                 235                 240
Glu Gln Arg Asn Leu Thr Leu Leu Gln Ala Arg Leu Ser Gln Asp Leu
                245                 250                 255
Ala Arg Glu Gln Ile Arg Tyr Ala Glu Thr Gly His Met Pro Thr Leu
            260                 265                 270
Gly Leu Thr Ala Ser Ser Ser Val Ser Asp Thr Asp Tyr Ser Gly Ser
        275                 280                 285
Lys Thr Ser Gly Ala Ala Ser Arg Tyr Ala Asp Ser Lys Ile Gly
    290                 295                 300
Gln Asn Ser Ile Gly Leu Ser Phe Asn Leu Pro Leu Tyr Ser Gly Gly
305                 310                 315                 320
Ser Val Thr Ser Gln Val Lys Gln Ala Gln Tyr Ser Phe Val Gly Ala
                325                 330                 335
Ser Glu Lys Leu Glu Ser Ala His Arg Asn Val Val Gln Thr Val Arg
            340                 345                 350
Ser Ser Tyr Asn Val Asn Ala Ser Ile Ser Ser Ile Lys Ala Tyr
        355                 360                 365
Glu Gln Ala Val Val Ser Ala Gln Ser Ser Leu Asp Ala Met Glu Ala
    370                 375                 380
Gly Tyr Ser Val Gly Thr Arg Thr Ile Val Asp Val Leu Asp Ala Thr
385                 390                 395                 400
Thr Thr Leu Tyr Asn Ala Lys Gln Gln Leu Ser Ser Ala Arg Tyr Asn
                405                 410                 415
Tyr Leu Ile Asn Gln Leu Asn Ile Lys Ser Ala Leu Gly Thr Leu Asn
            420                 425                 430
Glu Gln Asp Leu Val Ala Leu Asn Asn Ser Leu Gly Lys Pro Val Ser
        435                 440                 445
Thr Ala Pro Glu Ser Val Ala Pro Glu Asn Pro Gln Asp Ala Ala
    450                 455                 460
Val Asn Asn Met Ala Asn Gly Gly Asn Ala Pro Ala Met Gln Pro
465                 470                 475                 480
Ala Ala Ala Thr Arg Ser Ser Asn Ser Asn Ser Gly Asn Pro Phe Arg
                485                 490                 495
Gln
```

<210> SEQ ID NO 23
<211> LENGTH: 1401

```
<212> TYPE: DNA
<213> ORGANISM: Erwinia carotovora
<220> FEATURE:
<221> NAME/KEY: CDS
<222> LOCATION: (1)..(1401)

<400> SEQUENCE: 23 atg caa atg aag aaa ttg ctc cct ctt ctt att ggt ctg agc ctg ggt      48
Met Gln Met Lys Lys Leu Leu Pro Leu Leu Ile Gly Leu Ser Leu Gly
1               5                   10                  15 ggc ttt agc gcc atg agt cag gcg gaa aac cta tta cag gtt tac cag      96
Gly Phe Ser Ala Met Ser Gln Ala Glu Asn Leu Leu Gln Val Tyr Gln
                20                  25                  30 cag gca aaa agc acc aac cct gat tta cgc agc tct gcg gca acc cgc     144
Gln Ala Lys Ser Thr Asn Pro Asp Leu Arg Ser Ser Ala Ala Thr Arg
            35                  40                  45 gac gcc gcg ttt gaa aaa atc aat gaa tca cgc agc ccg ctg ctg cca     192
Asp Ala Ala Phe Glu Lys Ile Asn Glu Ser Arg Ser Pro Leu Leu Pro
        50                  55                  60 cag ttg ggt tta ggc gct gac tat acc tac aac aga ggc tac cgt gac     240
Gln Leu Gly Leu Gly Ala Asp Tyr Thr Tyr Asn Arg Gly Tyr Arg Asp
65                  70                  75                  80 agc aaa ggc gtc aac agc gac gtc aag ggt gct tca ctg caa ttg acc     288
Ser Lys Gly Val Asn Ser Asp Val Lys Gly Ala Ser Leu Gln Leu Thr
                85                  90                  95 cag acg ctg ttc gac atg tcc aaa tgg cgt gcg ctg aca ttg cag gaa     336
Gln Thr Leu Phe Asp Met Ser Lys Trp Arg Ala Leu Thr Leu Gln Glu
                100                 105                 110 aaa caa gcc ggt att gaa gac gta acc tat cag acc gct caa cag aac     384
Lys Gln Ala Gly Ile Glu Asp Val Thr Tyr Gln Thr Ala Gln Gln Asn
            115                 120                 125 ctg atg ctg aac acg gcg acc gct tat ttc aac gtg ctg cgc gct att     432
Leu Met Leu Asn Thr Ala Thr Ala Tyr Phe Asn Val Leu Arg Ala Ile
        130                 135                 140 gac tca ctg tcc tac atc aac gcg cag aaa cag gca att tat cgc cag     480
Asp Ser Leu Ser Tyr Ile Asn Ala Gln Lys Gln Ala Ile Tyr Arg Gln
145                 150                 155                 160 ttg gat caa acg aca cag cgt ttc aac gta ggt ctg gtt gcc att acc     528
Leu Asp Gln Thr Thr Gln Arg Phe Asn Val Gly Leu Val Ala Ile Thr
                165                 170                 175 gac gtt cag aac gct cgc gca caa tat gac agc gtg cta gcc aat gaa     576
Asp Val Gln Asn Ala Arg Ala Gln Tyr Asp Ser Val Leu Ala Asn Glu
                180                 185                 190 gtg ttg acg cgt aat acg cta gat aat gcg ctg gaa tca ctg cgc cag     624
Val Leu Thr Arg Asn Thr Leu Asp Asn Ala Leu Glu Ser Leu Arg Gln
            195                 200                 205 att acg ggc aat ttc tac ccg caa ttg gct ggt ctg aac atc gag cgt     672
Ile Thr Gly Asn Phe Tyr Pro Gln Leu Ala Gly Leu Asn Ile Glu Arg
        210                 215                 220 ttc tct acc cag aaa cct gaa gcc gtt aac aac ctg ctg aaa gaa gcc     720
Phe Ser Thr Gln Lys Pro Glu Ala Val Asn Asn Leu Leu Lys Glu Ala
225                 230                 235                 240 gaa aac cgc aac ttg aac ctg ttg tcc gca cgt ttg agc cag gat ttg     768
Glu Asn Arg Asn Leu Asn Leu Leu Ser Ala Arg Leu Ser Gln Asp Leu
                245                 250                 255 gca cgt gag cag att cgc tcc gcc gaa aca ggc tat atg ccg acg ctg     816
Ala Arg Glu Gln Ile Arg Ser Ala Glu Thr Gly Tyr Met Pro Thr Leu
                260                 265                 270 gac ctc acc gca tcg acg ggc gtg agc gat acc cgc tac tcg ggt tca     864
Asp Leu Thr Ala Ser Thr Gly Val Ser Asp Thr Arg Tyr Ser Gly Ser
            275                 280                 285
```

```
aga aca cag aac agt aac tcg ttt aac gac acc gac gca ggg caa cac    912
Arg Thr Gln Asn Ser Asn Ser Phe Asn Asp Thr Asp Ala Gly Gln His
    290                 295                 300 aga gta ggc atc aac ttc act ctg ccg ctt tac agc ggt ggc gct acc    960
Arg Val Gly Ile Asn Phe Thr Leu Pro Leu Tyr Ser Gly Gly Ala Thr
305                 310                 315                 320 aat tct cag gtg aag cag gca cag cac agc tat gtt agc tct agt gaa   1008
Asn Ser Gln Val Lys Gln Ala Gln His Ser Tyr Val Ser Ser Ser Glu
                325                 330                 335 ctg ctg gaa agc gca cac cgt tct gtt atc cag acg gta cgt tca tcg   1056
Leu Leu Glu Ser Ala His Arg Ser Val Ile Gln Thr Val Arg Ser Ser
            340                 345                 350 ttt aac aat att tct gcc tcc atc agc agc atc aac gct tac aaa cag   1104
Phe Asn Asn Ile Ser Ala Ser Ile Ser Ser Ile Asn Ala Tyr Lys Gln
        355                 360                 365 gct gaa gtg tct gca caa agc tct ttg gat gca atg gaa gct ggc tat   1152
Ala Glu Val Ser Ala Gln Ser Ser Leu Asp Ala Met Glu Ala Gly Tyr
    370                 375                 380 cag gta gga acg cgc acc atc gtt gac gta ctg gat gcc acc acc acg   1200
Gln Val Gly Thr Arg Thr Ile Val Asp Val Leu Asp Ala Thr Thr Thr
385                 390                 395                 400 ctg tat aac gcc aaa cag cag ctc tcc agc gca cgt tat gat tac ctg   1248
Leu Tyr Asn Ala Lys Gln Gln Leu Ser Ser Ala Arg Tyr Asp Tyr Leu
                405                 410                 415 atc aat cag tta aac atc aag tcc gca cag ggc acg ctg agc gaa acc   1296
Ile Asn Gln Leu Asn Ile Lys Ser Ala Gln Gly Thr Leu Ser Glu Thr
            420                 425                 430 gat ctg caa gcg ctg aat gcg tca ttg ggt cag ccg gtt tcc act aca   1344
Asp Leu Gln Ala Leu Asn Ala Ser Leu Gly Gln Pro Val Ser Thr Thr
        435                 440                 445 ccg acc gta acg gac aat acc gcc ccg cag gca aca acc gcc tcg gcg   1392
Pro Thr Val Thr Asp Asn Thr Ala Pro Gln Ala Thr Thr Ala Ser Ala
    450                 455                 460 cag cgt taa                                                        1401
Gln Arg
465
```

<210> SEQ ID NO 24
<211> LENGTH: 466
<212> TYPE: PRT
<213> ORGANISM: Erwinia carotovora

<400> SEQUENCE: 24

```
Met Gln Met Lys Lys Leu Leu Pro Leu Leu Ile Gly Leu Ser Leu Gly
1               5                   10                  15

Gly Phe

```
Leu Met Leu Asn Thr Ala Thr Ala Tyr Phe Asn Val Leu Arg Ala Ile
    130                 135                 140

Asp Ser Leu Ser Tyr Ile Asn Ala Gln Lys Gln Ala Ile Tyr Arg Gln
145                 150                 155                 160

Leu Asp Gln Thr Thr Gln Arg Phe Asn Val Gly Leu Val Ala Ile Thr
                165                 170                 175

Asp Val Gln Asn Ala Arg Ala Gln Tyr Asp Ser Val Leu Ala Asn Glu
            180                 185                 190

Val Leu Thr Arg Asn Thr Leu Asp Asn Ala Leu Glu Ser Leu Arg Gln
        195                 200                 205

Ile Thr Gly Asn Phe Tyr Pro Gln Leu Ala Gly Leu Asn Ile Glu Arg
    210                 215                 220

Phe Ser Thr Gln Lys Pro Glu Ala Val Asn Asn Leu Leu Lys Glu Ala
225                 230                 235                 240

Glu Asn Arg Asn Leu Asn Leu Leu Ser Ala Arg Leu Ser Gln Asp Leu
                245                 250                 255

Ala Arg Glu Gln Ile Arg Ser Ala Glu Thr Gly Tyr Met Pro Thr Leu
            260                 265                 270

Asp Leu Thr Ala Ser Thr Gly Val Ser Asp Thr Arg Tyr Ser Gly Ser
        275                 280                 285

Arg Thr Gln Asn Ser Asn Ser Phe Asn Asp Thr Asp Ala Gly Gln His
    290                 295                 300

Arg Val Gly Ile Asn Phe Thr Leu Pro Leu Tyr Ser Gly Gly Ala Thr
305                 310                 315                 320

Asn Ser Gln Val Lys Gln Ala Gln His Ser Tyr Val Ser Ser Ser Glu
                325                 330                 335

Leu Leu Glu Ser Ala His Arg Ser Val Ile Gln Thr Val Arg Ser Ser
            340                 345                 350

Phe Asn Asn Ile Ser Ala Ser Ile Ser Ser Ile Asn Ala Tyr Lys Gln
        355                 360                 365

Ala Glu Val Ser Ala Gln Ser Ser Leu Asp Ala Met Glu Ala Gly Tyr
    370                 375                 380

Gln Val Gly Thr Arg Thr Ile Val Asp Val Leu Asp Ala Thr Thr Thr
385                 390                 395                 400

Leu Tyr Asn Ala Lys Gln Gln Leu Ser Ser Ala Arg Tyr Asp Tyr Leu
                405                 410                 415

Ile Asn Gln Leu Asn Ile Lys Ser Ala Gln Gly Thr Leu Ser Glu Thr
            420                 425                 430

Asp Leu Gln Ala Leu Asn Ala Ser Leu Gly Gln Pro Val Ser Thr Thr
        435                 440                 445

Pro Thr Val Thr Asp Asn Thr Ala Pro Gln Ala Thr Thr Ala Ser Ala
    450                 455                 460

Gln Arg
465

<210> SEQ ID NO 25
<211> LENGTH: 1494
<212> TYPE: DNA
<213> ORGANISM: Serratia proteamaculans
<220> FEATURE:
<221> NAME/KEY: CDS
<222> LOCATION: (1)..(1494)

<400> SEQUENCE: 25 atg aag aaa ctg ctc ccc ctt ctt atc gga ctg agc ctg ggc ggc ttc    48
Met Lys Lys Leu Leu Pro Leu Leu Ile Gly Leu Ser Leu Gly Gly Phe
1               5                   10                  15
```

| | | | | | | | | | | | | | | | |
|---|---|---|---|---|---|---|---|---|---|---|---|---|---|---|---|
| agt | gca | atg | agc | cag | gca | gag | aac | ctg | ctg | cag | gtc | tac | aaa | cag | gcc | 96 |
| Ser | Ala | Met | Ser | Gln | Ala | Glu | Asn | Leu | Leu | Gln | Val | Tyr | Lys | Gln | Ala |
| | | 20 | | | | 25 | | | | 30 | | | | | agt gca atg agc cag gca gag aac ctg ctg cag gtc tac aaa cag gcc    96
Ser Ala Met Ser Gln Ala Glu Asn Leu Leu Gln Val Tyr Lys Gln Ala
        20                25             30 agg gaa agt aac ccg gat ctg cgc aaa acc gcc gct gac cgt gac gcc    144
Arg Glu Ser Asn Pro Asp Leu Arg Lys Thr Ala Ala Asp Arg Asp Ala
               35                40             45 gca ttc gaa aaa atc aac gaa gca cgc agc ccg ttg ctg ccg cag ttg    192
Ala Phe Glu Lys Ile Asn Glu Ala Arg Ser Pro Leu Leu Pro Gln Leu
50                    55                60 ggt ttg agc gcc ggt tac act tac acc aat ggc tac cgt gac agc aaa    240
Gly Leu Ser Ala Gly Tyr Thr Tyr Thr Asn Gly Tyr Arg Asp Ser Lys
65              70                75             80 gat gcc aac agc gat gcc acc agt ggc tcc ctg gcg ttg acc cag act    288
Asp Ala Asn Ser Asp Ala Thr Ser Gly Ser Leu Ala Leu Thr Gln Thr
               85                90             95 atc ttc gac atg tcc aaa tgg cgt gcg ctg acg ctg cag gaa aaa acc    336
Ile Phe Asp Met Ser Lys Trp Arg Ala Leu Thr Leu Gln Glu Lys Thr
               100             105           110 gcc ggc att tcc gac gtg act ttc caa acc tcg tca cag cag ctg atc    384
Ala Gly Ile Ser Asp Val Thr Phe Gln Thr Ser Ser Gln Gln Leu Ile
             115             120            125 ctc gat acc gct acc gcc tat ttt aac gtg ctg agc gcc atc gat acg    432
Leu Asp Thr Ala Thr Ala Tyr Phe Asn Val Leu Ser Ala Ile Asp Thr
        130             135            140 ctg tcc tac acc cag gcg aac aag caa gcg gtt tac cgc acc ctg gac    480
Leu Ser Tyr Thr Gln Ala Asn Lys Gln Ala Val Tyr Arg Thr Leu Asp
145            150             155            160 cag acc acc caa cgc ttt aac gtg ggc ctg gtc gcg atc acc gac gtg    528
Gln Thr Thr Gln Arg Phe Asn Val Gly Leu Val Ala Ile Thr Asp Val
                     165             170            175 caa aac gcc cgt tcg tcc tac gat acc gtg ctg gcg gcc gaa gtc acc    576
Gln Asn Ala Arg Ser Ser Tyr Asp Thr Val Leu Ala Ala Glu Val Thr
               180             185            190 gcc cgt aac aac ctg gac aac gcg ctg gaa aaa ctg cgc cag gtc acc    624
Ala Arg Asn Asn Leu Asp Asn Ala Leu Glu Lys Leu Arg Gln Val Thr
            195              200            205 ggc acc ttc tat ccg gaa ctg gcc tcg ttg aat acc gac cgt ttc aac    672
Gly Thr Phe Tyr Pro Glu Leu Ala Ser Leu Asn Thr Asp Arg Phe Asn
        210             215            220 acc aaa cgc ccg gat gca gtc aat aat ctg ctg aaa gaa gcc gaa agc    720
Thr Lys Arg Pro Asp Ala Val Asn Asn Leu Leu Lys Glu Ala Glu Ser
225            230             235            240 cgt aac ctg agc ctg ttg tcc gct cgc ctg agc cag gat ctg gcc cgt    768
Arg Asn Leu Ser Leu Leu Ser Ala Arg Leu Ser Gln Asp Leu Ala Arg
                245             250            255 gag cag atc cgt tcc gca cag acc ggt tat atg cct acc gtt gat ttc    816
Glu Gln Ile Arg Ser Ala Gln Thr Gly Tyr Met Pro Thr Val Asp Phe
               260             265            270 agc gca tcc act gcg gtg agc aat act aat tac agc ggt tct cgc aac    864
Ser Ala Ser Thr Ala Val Ser Asn Thr Asn Tyr Ser Gly Ser Arg Asn
        275             280            285 gtg aac aac gac gct gat att ggt cag aac aaa gtg ggc ctg agc ttt    912
Val Asn Asn Asp Ala Asp Ile Gly Gln Asn Lys Val Gly Leu Ser Phe
           290             295            300 aac ttg ccg ttg tac agc ggc ggc cag acc aac tca cag gtg cag cag    960
Asn Leu Pro Leu Tyr Ser Gly Gly Gln Thr Asn Ser Gln Val Gln Gln
305            310             315            320 gcg cag tac aac ttc gtt ggc gcc agt gag caa ctg gaa agc gcc cac    1008
Ala Gln Tyr Asn Phe Val Gly Ala Ser Glu Gln Leu Glu Ser Ala His
                325             330            335

```
cgc agc gta gtg cag acc gtg cgt tct tcg ttc aat aac gtg aat gcc    1056
Arg Ser Val Val Gln Thr Val Arg Ser Ser Phe Asn Asn Val Asn Ala
        340                 345                 350 tcg atc agc agc atc aac gcc tac caa caa gcg gta gtg tct gcc cag    1104
Ser Ile Ser Ser Ile Asn Ala Tyr Gln Gln Ala Val Val Ser Ala Gln
                355                 360                 365 agt tca ttg gat gcg acc gag gcc ggt tac cag gta ggt acc cgt acc    1152
Ser Ser Leu Asp Ala Thr Glu Ala Gly Tyr Gln Val Gly Thr Arg Thr
    370                 375                 380 atc gtc gac gtg ctg gat gcg acc agt acg ctg tat aac gcc aag caa    1200
Ile Val Asp Val Leu Asp Ala Thr Ser Thr Leu Tyr Asn Ala Lys Gln
385                 390                 395                 400 cag ctc tcc agc gcg cgt tat acc tac ctg atc aac caa ctg aac atc    1248
Gln Leu Ser Ser Ala Arg Tyr Thr Tyr Leu Ile Asn Gln Leu Asn Ile
                405                 410                 415 aag tcg gcg ctc ggt acc ctg aac gag aac gat ctg atg atg ctg aat    1296
Lys Ser Ala Leu Gly Thr Leu Asn Glu Asn Asp Leu Met Met Leu Asn
            420                 425                 430 ggc gca ttg ggt aaa ccg att tct act tcg caa gac gtg gta gcg cca    1344
Gly Ala Leu Gly Lys Pro Ile Ser Thr Ser Gln Asp Val Val Ala Pro
        435                 440                 445 ccg act acc gca cag gac gct tac gct gaa ggc tat aac ggc aac gcc    1392
Pro Thr Thr Ala Gln Asp Ala Tyr Ala Glu Gly Tyr Asn Gly Asn Ala
    450                 455                 460 cct gcg cca caa act gca gca ccg gtt gcc acc cgc gcc tcc gca ccg    1440
Pro Ala Pro Gln Thr Ala Ala Pro Val Ala Thr Arg Ala Ser Ala Pro
465                 470                 475                 480 gcg gcc acc acc agc cag cct gca cgc acc agc ggt aat cca ttc cgt    1488
Ala Ala Thr Thr Ser Gln Pro Ala Arg Thr Ser Gly Asn Pro Phe Arg
                485                 490                 495 aat tga                                                             1494
Asn

<210> SEQ ID NO 26
<211> LENGTH: 497
<212> TYPE: PRT
<213> ORGANISM: Serratia proteamaculans

<400> SEQUENCE: 26

Met Lys Lys Leu Leu Pro Leu Leu Ile Gly Leu Ser Leu Gly Gly Phe
1               5                   10                  15

Ser Ala Met Ser Gln Ala Glu Asn Leu Leu Gln Val Tyr Lys Gln Ala
            20                  25                  30

Arg Glu Ser Asn Pro Asp Leu Arg Lys Thr Ala Ala Asp Arg Asp Ala
        35                  40                  45

Ala Phe Glu Lys Ile Asn Glu Ala Arg Ser Pro Leu Leu Pro Gln Leu
    50                  55                  60

Gly Leu Ser Ala Gly Tyr Thr Tyr Thr Asn Gly Tyr Arg Asp Ser Lys
65                  70                  75                  80

Asp Ala Asn Ser Asp Ala Thr Ser Gly Ser Leu Ala Leu Thr Gln Thr
                85                  90                  95

Ile Phe Asp Met Ser Lys Trp Arg Ala Leu Thr Leu Gln Glu Lys Thr
            100                 105                 110

Ala Gly Ile Ser Asp Val Thr Phe Gln Thr Ser Gln Gln Leu Ile
        115                 120                 125

Leu Asp Thr Ala Thr Ala Tyr Phe Asn Val Leu Ser Ala Ile Asp Thr
    130                 135                 140

Leu Ser Tyr Thr Gln Ala Asn Lys Gln Ala Val Tyr Arg Thr Leu Asp
```

```
            145                 150                 155                 160
Gln Thr Thr Gln Arg Phe Asn Val Gly Leu Val Ala Ile Thr Asp Val
                165                 170                 175

Gln Asn Ala Arg Ser Ser Tyr Asp Thr Val Leu Ala Ala Glu Val Thr
            180                 185                 190

Ala Arg Asn Asn Leu Asp Asn Ala Leu Glu Lys Leu Arg Gln Val Thr
        195                 200                 205

Gly Thr Phe Tyr Pro Glu Leu Ala Ser Leu Asn Thr Asp Arg Phe Asn
    210                 215                 220

Thr Lys Arg Pro Asp Ala Val Asn Asn Leu Leu Lys Glu Ala Glu Ser
225                 230                 235                 240

Arg Asn Leu Ser Leu Leu Ser Ala Arg Leu Ser Gln Asp Leu Ala Arg
                245                 250                 255

Glu Gln Ile Arg Ser Ala Gln Thr Gly Tyr Met Pro Thr Val Asp Phe
            260                 265                 270

Ser Ala Ser Thr Ala Val Ser Asn Thr Asn Tyr Ser Gly Ser Arg Asn
        275                 280                 285

Val Asn Asn Asp Ala Asp Ile Gly Gln Asn Lys Val Gly Leu Ser Phe
    290                 295                 300

Asn Leu Pro Leu Tyr Ser Gly Gly Gln Thr Asn Ser Gln Val Gln Gln
305                 310                 315                 320

Ala Gln Tyr Asn Phe Val Gly Ala Ser Glu Gln Leu Glu Ser Ala His
                325                 330                 335

Arg Ser Val Val Gln Thr Val Arg Ser Ser Phe Asn Asn Val Asn Ala
            340                 345                 350

Ser Ile Ser Ser Ile Asn Ala Tyr Gln Gln Ala Val Val Ser Ala Gln
        355                 360                 365

Ser Ser Leu Asp Ala Thr Glu Ala Gly Tyr Gln Val Gly Thr Arg Thr
    370                 375                 380

Ile Val Asp Val Leu Asp Ala Thr Ser Thr Leu Tyr Asn Ala Lys Gln
385                 390                 395                 400

Gln Leu Ser Ser Ala Arg Tyr Thr Tyr Leu Ile Asn Gln Leu Asn Ile
                405                 410                 415

Lys Ser Ala Leu Gly Thr Leu Asn Glu Asn Asp Leu Met Met Leu Asn
            420                 425                 430

Gly Ala Leu Gly Lys Pro Ile Ser Thr Ser Gln Asp Val Val Ala Pro
        435                 440                 445

Pro Thr Thr Ala Gln Asp Ala Tyr Ala Glu Gly Tyr Asn Gly Asn Ala
    450                 455                 460

Pro Ala Pro Gln Thr Ala Ala Pro Val Ala Thr Arg Ala Ser Ala Pro
465                 470                 475                 480

Ala Ala Thr Thr Ser Gln Pro Ala Arg Thr Ser Gly Asn Pro Phe Arg
                485                 490                 495

Asn

<210> SEQ ID NO 27
<211> LENGTH: 1326
<212> TYPE: DNA
<213> ORGANISM: Aeromonas salmonicida
<220> FEATURE:
<221> NAME/KEY: CDS
<222> LOCATION: (1)..(1326)

<400> SEQUENCE: 27 atg aaa aga aca ctc ttg tca gcc atg gtg ttg ctg ggc gtc agc gcc      48
Met Lys Arg Thr Leu Leu Ser Ala Met Val Leu Leu Gly Val Ser Ala
```

-continued

```
1               5                   10                  15 ggc gcc cac gcc gag aac ctg ctc gat att tac caa caa gcc cag atc      96
Gly Ala His Ala Glu Asn Leu Leu Asp Ile Tyr Gln Gln Ala Gln Ile
                20                  25                  30 aag gac acc caa ctg cag gaa tcc aag gcc aag cgt gac caa gcc ttc     144
Lys Asp Thr Gln Leu Gln Glu Ser Lys Ala Lys Arg Asp Gln Ala Phe
                35                  40                  45 gag aag atc aat gaa tcc cgc gca gcc ctc ttg ccg caa atc aat ctg     192
Glu Lys Ile Asn Glu Ser Arg Ala Ala Leu Leu Pro Gln Ile Asn Leu
 50                  55                  60 gga gcc ggc ctg aac tac ctg caa aac aag ggt gat acc cag acc aac     240
Gly Ala Gly Leu Asn Tyr Leu Gln Asn Lys Gly Asp Thr Gln Thr Asn
 65                  70                  75                  80 agc aac gct act ggc tcc ctc tcg ctg gat caa tct atc tat cgt cgc     288
Ser Asn Ala Thr Gly Ser Leu Ser Leu Asp Gln Ser Ile Tyr Arg Arg
                85                  90                  95 agc aac tgg gtc aac ctg gac ctg acc gag aag agc gcc acc cag tcc     336
Ser Asn Trp Val Asn Leu Asp Leu Thr Glu Lys Ser Ala Thr Gln Ser
                100                 105                 110 gat gtg gcc tac aac ctc gaa ata cag aat ctg atg ctg cgc acc gcc     384
Asp Val Ala Tyr Asn Leu Glu Ile Gln Asn Leu Met Leu Arg Thr Ala
                115                 120                 125 cag gcc tat ttc aac gtg ctc aag gca atg gac acc ctg gaa ttc gtc     432
Gln Ala Tyr Phe Asn Val Leu Lys Ala Met Asp Thr Leu Glu Phe Val
                130                 135                 140 cgc gcc aac aag gcc gcc gta gaa cgt cag ctg gaa cag acc cag cag     480
Arg Ala Asn Lys Ala Ala Val Glu Arg Gln Leu Glu Gln Thr Gln Gln
145                 150                 155                 160 cgc ttc gaa gtg ggc ctg acc gcc atc acg gac gtg cat gag gct gaa     528
Arg Phe Glu Val Gly Leu Thr Ala Ile Thr Asp Val His Glu Ala Glu
                165                 170                 175 gcc gag cgc gat cag gca ctg gcg gac gag atc aat gcc gag aac acg     576
Ala Glu Arg Asp Gln Ala Leu Ala Asp Glu Ile Asn Ala Glu Asn Thr
                180                 185                 190 ctg gac aac agc tac gag agt ctg cgc gag ctg acc ggc atc gac cac     624
Leu Asp Asn Ser Tyr Glu Ser Leu Arg Glu Leu Thr Gly Ile Asp His
                195                 200                 205 cgt cag ctg gac gta ctc aac act gag cgt ttc agc ccg cag aag acg     672
Arg Gln Leu Asp Val Leu Asn Thr Glu Arg Phe Ser Pro Gln Lys Thr
                210                 215                 220 ccg ttc aac tcc gac aaa tgg ctg gag ctg gca ctg gac aag aac ctg     720
Pro Phe Asn Ser Asp Lys Trp Leu Glu Leu Ala Leu Asp Lys Asn Leu
225                 230                 235                 240 caa ctg cac agc gcc cgc atc ggc aag gat atc gcc aag gag cag atc     768
Gln Leu His Ser Ala Arg Ile Gly Lys Asp Ile Ala Lys Glu Gln Ile
                245                 250                 255 gat ctg gcc aag acc ggt cac gag ccg acg ctg gat ctg ggt gcc ggt     816
Asp Leu Ala Lys Thr Gly His Glu Pro Thr Leu Asp Leu Gly Ala Gly
                260                 265                 270 ctc tcc agc acc tat agc gat tac aag gac gag atc cgc aac ccc gag     864
Leu Ser Ser Thr Tyr Ser Asp Tyr Lys Asp Glu Ile Arg Asn Pro Glu
                275                 280                 285 agc aac agc aat cag ggc aac ata ggc ctg aac ttc aag ctg ccg ctc     912
Ser Asn Ser Asn Gln Gly Asn Ile Gly Leu Asn Phe Lys Leu Pro Leu
                290                 295                 300 tac acg ggt ggc gcg acc acc tcc cag gtc aag cag tcc cag ttc aac     960
Tyr Thr Gly Gly Ala Thr Thr Ser Gln Val Lys Gln Ser Gln Phe Asn
305                 310                 315                 320 tat gtg gcg gcc agc gag cag ctg gag cgc agc ttc cgc tct gtg cag    1008
Tyr Val Ala Ala Ser Glu Gln Leu Glu Arg Ser Phe Arg Ser Val Gln
```

```
                        325                     330                     335
agc aca gta cgc tcc tcc tat aac aac gtg aac gcc agc ata ggt tcg      1056
Ser Thr Val Arg Ser Ser Tyr Asn Asn Val Asn Ala Ser Ile Gly Ser
            340                     345                     350 gta cgc gcc tac ggc cag tcc gtc atc tcc gcc gac agc gcc ctc aag      1104
Val Arg Ala Tyr Gly Gln Ser Val Ile Ser Ala Asp Ser Ala Leu Lys
                355                     360                     365 gcc acc gaa gcg ggc tat gaa gtc ggt acc cgc acc ata gtc gac gtg      1152
Ala Thr Glu Ala Gly Tyr Glu Val Gly Thr Arg Thr Ile Val Asp Val
    370                     375                     380 ctg gac tct acc cgc aag ctc tac cag gcc aag cag aaa ctc tcc gaa      1200
Leu Asp Ser Thr Arg Lys Leu Tyr Gln Ala Lys Gln Lys Leu Ser Glu
385                     390                     395                 400 gcc cgt tac aac tac att ctc agc atc ctc tcc ctc aag cag gcc gcc      1248
Ala Arg Tyr Asn Tyr Ile Leu Ser Ile Leu Ser Leu Lys Gln Ala Ala
                405                     410                     415 ggc acg ctg gag cag aaa gat ctg gaa gaa gta aac cag gga ctg ata      1296
Gly Thr Leu Glu Gln Lys Asp Leu Glu Glu Val Asn Gln Gly Leu Ile
            420                     425                     430 cct gcc gct cag gtc aag aac aag tcc tga                              1326
Pro Ala Ala Gln Val Lys Asn Lys Ser
                435                     440

<210> SEQ ID NO 28
<211> LENGTH: 441
<212> TYPE: PRT
<213> ORGANISM: Aeromonas salmonicida

<400> SEQUENCE: 28

Met Lys Arg Thr Leu Leu Ser Ala Met Val Leu Leu Gly Val Ser Ala
1               5                   10                  15

Gly Ala His Ala Glu Asn Leu Leu Asp Ile Tyr Gln Gln Ala Gln Ile
            20                  25                  30

Lys Asp Thr Gln Leu Gln Glu Ser Lys Ala Lys Arg Asp Gln Ala Phe
        35                  40                  45

Glu Lys Ile Asn Glu Ser Arg Ala Ala Leu Leu Pro Gln Ile Asn Leu
    50                  55                  60

Gly Ala Gly Leu Asn Tyr Leu Gln Asn Lys Gly Asp Thr Gln Thr Asn
65                  70                  75                  80

Ser Asn Ala Thr Gly Ser Leu Ser Leu Asp Gln Ser Ile Tyr Arg Arg
                85                  90                  95

Ser Asn Trp Val Asn Leu Asp Leu Thr Glu Lys Ser Ala Thr Gln Ser
            100                 105                 110

Asp Val Ala Tyr Asn Leu Glu Ile Gln Asn Leu Met Leu Arg Thr Ala
        115                 120                 125

Gln Ala Tyr Phe Asn Val Leu Lys Ala Met Asp Thr Leu Glu Phe Val
    130                 135                 140

Arg Ala Asn Lys Ala Ala Val Glu Arg Gln Leu Glu Gln Thr Gln Gln
145                 150                 155                 160

Arg Phe Glu Val Gly Leu Thr Ala Ile Thr Asp Val His Glu Ala Glu
                165                 170                 175

Ala Glu Arg Asp Gln Ala Leu Ala Asp Glu Ile Asn Ala Glu Asn Thr
            180                 185                 190

Leu Asp Asn Ser Tyr Glu Ser Leu Arg Glu Leu Thr Gly Ile Asp His
        195                 200                 205

Arg Gln Leu Asp Val Leu Asn Thr Glu Arg Phe Ser Pro Gln Lys Thr
    210                 215                 220
```

-continued

```
Pro Phe Asn Ser Asp Lys Trp Leu Glu Leu Ala Leu Asp Lys Asn Leu
225                 230                 235                 240

Gln Leu His Ser Ala Arg Ile Gly Lys Asp Ile Ala Lys Glu Gln Ile
            245                 250                 255

Asp Leu Ala Lys Thr Gly His Glu Pro Thr Leu Asp Leu Gly Ala Gly
        260                 265                 270

Leu Ser Ser Thr Tyr Ser Asp Tyr Lys Asp Glu Ile Arg Asn Pro Glu
    275                 280                 285

Ser Asn Ser Asn Gln Gly Asn Ile Gly Leu Asn Phe Lys Leu Pro Leu
290                 295                 300

Tyr Thr Gly Gly Ala Thr Thr Ser Gln Val Lys Gln Ser Gln Phe Asn
305                 310                 315                 320

Tyr Val Ala Ala Ser Glu Gln Leu Glu Arg Ser Phe Arg Ser Val Gln
                325                 330                 335

Ser Thr Val Arg Ser Ser Tyr Asn Asn Val Asn Ala Ser Ile Gly Ser
            340                 345                 350

Val Arg Ala Tyr Gly Gln Ser Val Ile Ser Ala Asp Ser Ala Leu Lys
        355                 360                 365

Ala Thr Glu Ala Gly Tyr Glu Val Gly Thr Arg Thr Ile Val Asp Val
370                 375                 380

Leu Asp Ser Thr Arg Lys Leu Tyr Gln Ala Lys Gln Lys Leu Ser Glu
385                 390                 395                 400

Ala Arg Tyr Asn Tyr Ile Leu Ser Ile Leu Ser Leu Lys Gln Ala Ala
                405                 410                 415

Gly Thr Leu Glu Gln Lys Asp Leu Glu Glu Val Asn Gln Gly Leu Ile
            420                 425                 430

Pro Ala Ala Gln Val Lys Asn Lys Ser
        435                 440
```

<210> SEQ ID NO 29
<211> LENGTH: 1326
<212> TYPE: DNA
<213> ORGANISM: Vibrio vulnificus
<220> FEATURE:
<221> NAME/KEY: CDS
<222> LOCATION: (1)..(1326)

<400> SEQUENCE: 29

```
atg aaa aaa ctg ctt cca cta ctt att ggt gca gcg cta ggt agc ctg      48
Met Lys Lys Leu Leu Pro Leu Leu Ile Gly Ala Ala Leu Gly Ser Leu
1               5                   10                  15 agt tct tca gtg tgg gct gat tcc ttg gca gaa atc tat gat ctg gca      96
Ser Ser Ser Val Trp Ala Asp Ser Leu Ala Glu Ile Tyr Asp Leu Ala
            20                  25                  30 aag caa aac gat cca cag tta ttg agc gta caa gct aaa cgt gac gcc     144
Lys Gln Asn Asp Pro Gln Leu Leu Ser Val Gln Ala Lys Arg Asp Ala
        35                  40                  45 gca ttt gaa gcg gtc act tct agc cgt agt acc tta tta ccg caa att     192
Ala Phe Glu Ala Val Thr Ser Ser Arg Ser Thr Leu Leu Pro Gln Ile
50                  55                  60 aat tta acc gca ggt tat aac cta aaa cgc ggt gat acg gat ctt gat     240
Asn Leu Thr Ala Gly Tyr Asn Leu Lys Arg Gly Asp Thr Asp Leu Asp
65                  70                  75                  80 gct ggg gcg acg atc gat aat gac caa aat gca tta act gct ggg att     288
Ala Gly Ala Thr Ile Asp Asn Asp Gln Asn Ala Leu Thr Ala Gly Ile
                85                  90                  95 aat ttc tct cag gaa ctg tat cag cgt tcc tct tgg atc acg cta gac     336
Asn Phe Ser Gln Glu Leu Tyr Gln Arg Ser Ser Trp Ile Thr Leu Asp
            100                 105                 110
```

```
aac gca gag aaa agc gct cgt caa gca gat gca gca tac gca gcg acg      384
Asn Ala Glu Lys Ser Ala Arg Gln Ala Asp Ala Ala Tyr Ala Ala Thr
            115                 120                 125 caa cag ggt ttg atc tta aga acc gcg caa gcg tac ttt gag gtg cta      432
Gln Gln Gly Leu Ile Leu Arg Thr Ala Gln Ala Tyr Phe Glu Val Leu
        130                 135                 140 aaa gcg caa gac aac tta gaa ttt gtc cgt gca gaa aaa gcg gcg gtt      480
Lys Ala Gln Asp Asn Leu Glu Phe Val Arg Ala Glu Lys Ala Ala Val
145                 150                 155                 160 gct cgt cag cta gag caa acc aaa caa cgt ttt gaa gtg ggc ctc tcg      528
Ala Arg Gln Leu Glu Gln Thr Lys Gln Arg Phe Glu Val Gly Leu Ser
                165                 170                 175 gcc att aca gac gtg cat gac gcc caa gcg caa tac gat ggc gta tta      576
Ala Ile Thr Asp Val His Asp Ala Gln Ala Gln Tyr Asp Gly Val Leu
            180                 185                 190 gct gac gaa gtt ctg gcc gaa aac agc cta acc aac agt tat gaa gcg      624
Ala Asp Glu Val Leu Ala Glu Asn Ser Leu Thr Asn Ser Tyr Glu Ala
        195                 200                 205 ttg cgt gaa atc aca ggt caa gag cat aaa aac ctg aac gtg tta gat      672
Leu Arg Glu Ile Thr Gly Gln Glu His Lys Asn Leu Asn Val Leu Asp
210                 215                 220 acc aag cgt ttc tca gca agc cgc tca aat gct tca gct gaa acc ttg      720
Thr Lys Arg Phe Ser Ala Ser Arg Ser Asn Ala Ser Ala Glu Thr Leu
225                 230                 235                 240 atc gaa gaa gcg caa gag aaa aac tta agc tta ctg tca gcg cgt atc      768
Ile Glu Glu Ala Gln Glu Lys Asn Leu Ser Leu Leu Ser Ala Arg Ile
                245                 250                 255 aca aaa gac atc gcc aaa gac aat att tct cta gcg agc tct ggc cac      816
Thr Lys Asp Ile Ala Lys Asp Asn Ile Ser Leu Ala Ser Ser Gly His
            260                 265                 270 ctt cca tct ctg act cta gac ggt ggc tac aac tac gca gac gtt agt      864
Leu Pro Ser Leu Thr Leu Asp Gly Gly Tyr Asn Tyr Ala Asp Val Ser
        275                 280                 285 aac agt gca caa agt gat ggt aca acc aat aat ttc aat gtg ggt gta      912
Asn Ser Ala Gln Ser Asp Gly Thr Thr Asn Asn Phe Asn Val Gly Val
290                 295                 300 aat ctc gtt gtt cca ctc tat acc ggt ggt aat aca acg tcg caa acc      960
Asn Leu Val Val Pro Leu Tyr Thr Gly Gly Asn Thr Thr Ser Gln Thr
305                 310                 315                 320 aaa caa gct gag ttt aat tac gtc tct gcg agc caa gat ctt gaa gcc     1008
Lys Gln Ala Glu Phe Asn Tyr Val Ser Ala Ser Gln Asp Leu Glu Ala
                325                 330                 335 act tat cgc ggt gtc gtg aaa gaa gtg cga gcg caa aac aac aac atc     1056
Thr Tyr Arg Gly Val Val Lys Glu Val Arg Ala Gln Asn Asn Asn Ile
            340                 345                 350 aat gcc tca atc ggc gca ctt cgt gcg tat gag caa tct gtt gtt tct     1104
Asn Ala Ser Ile Gly Ala Leu Arg Ala Tyr Glu Gln Ser Val Val Ser
        355                 360                 365 gcg cgt tca gca tta gaa gca acc gaa gca ggt ttt gat gtg ggt act     1152
Ala Arg Ser Ala Leu Glu Ala Thr Glu Ala Gly Phe Asp Val Gly Thr
370                 375                 380 cgt act att gtg gat gtc ctt gat gcc act cgt cgc ctt tac gat gcc     1200
Arg Thr Ile Val Asp Val Leu Asp Ala Thr Arg Arg Leu Tyr Asp Ala
385                 390                 395                 400 aac aaa aac cta tcg aat gca cgc tac aac tac atc ttg agt gta ctg     1248
Asn Lys Asn Leu Ser Asn Ala Arg Tyr Asn Tyr Ile Leu Ser Val Leu
                405                 410                 415 caa ctt cgt cag gcg gtg ggt aca ctg agc gag caa gat gta ctg gat     1296
Gln Leu Arg Gln Ala Val Gly Thr Leu Ser Glu Gln Asp Val Leu Asp
            420                 425                 430
```

```
gtt gat gct ggt ttg att gcg aaa aag taa                              1326
Val Asp Ala Gly Leu Ile Ala Lys Lys
        435                 440

<210> SEQ ID NO 30
<211> LENGTH: 441
<212> TYPE: PRT
<213> ORGANISM: Vibrio vulnificus

<400> SEQUENCE: 30

Met Lys Lys Leu Leu Pro Leu Ile Gly Ala Ala Leu Gly Ser Leu
1               5                   10                  15

Ser Ser Ser Val Trp Ala Asp Ser Leu Ala Glu Ile Tyr Asp Leu Ala
            20                  25                  30

Lys Gln Asn Asp Pro Gln Leu Leu Ser Val Gln Ala Lys Arg Asp Ala
        35                  40                  45

Ala Phe Glu Ala Val Thr Ser Ser Arg Ser Thr Leu Leu Pro Gln Ile
    50                  55                  60

Asn Leu Thr Ala Gly Tyr Asn Leu Lys Arg Gly Asp Thr Asp Leu Asp
65                  70                  75                  80

Ala Gly Ala Thr Ile Asp Asn Asp Gln Asn Ala Leu Thr Ala Gly Ile
                85                  90                  95

Asn Phe Ser Gln Glu Leu Tyr Gln Arg Ser Ser Trp Ile Thr Leu Asp
            100                 105                 110

Asn Ala Glu Lys Ser Ala Arg Gln Ala Asp Ala Tyr Ala Ala Thr
        115                 120                 125

Gln Gln Gly Leu Ile Leu Arg Thr Ala Gln Ala Tyr Phe Glu Val Leu
    130                 135                 140

Lys Ala Gln Asp Asn Leu Glu Phe Val Arg Ala Glu Lys Ala Ala Val
145                 150                 155                 160

Ala Arg Gln Leu Glu Gln Thr Lys Gln Arg Phe Glu Val Gly Leu Ser
                165                 170                 175

Ala Ile Thr Asp Val His Asp Ala Gln Ala Gln Tyr Asp Gly Val Leu
            180                 185                 190

Ala Asp Glu Val Leu Ala Glu Asn Ser Leu Thr Asn Ser Tyr Glu Ala
        195                 200                 205

Leu Arg Glu Ile Thr Gly Gln Glu His Lys Asn Leu Asn Val Leu Asp
    210                 215                 220

Thr Lys Arg Phe Ser Ala Ser Arg Ser Asn Ala Ser Ala Glu Thr Leu
225                 230                 235                 240

Ile Glu Glu Ala Gln Glu Lys Asn Leu Ser Leu Ser Ala Arg Ile
                245                 250                 255

Thr Lys Asp Ile Ala Lys Asp Asn Ile Ser Leu Ala Ser Ser Gly His
            260                 265                 270

Leu Pro Ser Leu Thr Leu Asp Gly Gly Tyr Asn Tyr Ala Asp Val Ser
        275                 280                 285

Asn Ser Ala Gln Ser Asp Gly Thr Thr Asn Asn Phe Asn Val Gly Val
    290                 295                 300

Asn Leu Val Val Pro Leu Tyr Thr Gly Gly Asn Thr Thr Ser Gln Thr
305                 310                 315                 320

Lys Gln Ala Glu Phe Asn Tyr Val Ser Ala Ser Gln Asp Leu Glu Ala
                325                 330                 335

Thr Tyr Arg Gly Val Val Lys Glu Val Arg Ala Gln Asn Asn Asn Ile
            340                 345                 350

Asn Ala Ser Ile Gly Ala Leu Arg Ala Tyr Glu Gln Ser Val Val Ser
```

-continued

```
                355                 360                 365
Ala Arg Ser Ala Leu Glu Ala Thr Glu Ala Gly Phe Asp Val Gly Thr
            370                 375                 380

Arg Thr Ile Val Asp Val Leu Asp Ala Thr Arg Arg Leu Tyr Asp Ala
385                 390                 395                 400

Asn Lys Asn Leu Ser Asn Ala Arg Tyr Asn Tyr Ile Leu Ser Val Leu
            405                 410                 415

Gln Leu Arg Gln Ala Val Gly Thr Leu Ser Glu Gln Asp Val Leu Asp
            420                 425                 430

Val Asp Ala Gly Leu Ile Ala Lys Lys
            435                 440
```

L-CYSTEINE-PRODUCING BACTERIUM AND A METHOD FOR PRODUCING L-CYSTEINE

This application is a continuation under 35 U.S.C. §120 of PCT Patent Application No. PCT/JP2009/053021, filed Feb. 20, 2009, which claims priority under 35 U.S.C. §119 to Japanese Patent Application No. 2008-040167, filed on Feb. 21, 2008, which are incorporated in their entireties by reference. The Sequence Listing in electronic format filed herewith is also hereby incorporated by reference in its entirety (File Name: 2010-08-18T_US-441_Seq_List; File Size: 120 KB; Date Created: Aug. 18, 2010).

BACKGROUND OF THE INVENTION

1. Field of the Invention

The present invention relates to a method for producing L-cysteine and related substances. Specifically, the present invention relates to a bacterium suitable for the production of L-cysteine and related substances and a method for producing L-cysteine and related substances utilizing the bacterium. L-cysteine and L-cysteine-related substances are utilized in the fields of drugs, cosmetics, and foods.

2. Brief Description of the Related Art

L-cysteine can be obtained by extraction from keratin-containing substances such as hair, horns and feathers, or by the conversion of the precursor DL-2-aminothiazoline-4-carboxylic acid using a microbial enzyme. L-cysteine has also been produced on a large scale by using an immobilized enzyme method and a novel enzyme. Furthermore, production of L-cysteine by fermentation utilizing a microorganism has also been attempted.

Microorganisms, which are able to produce L-cysteine, are also known. For example, a coryneform bacterium with increased intracellular serine acetyltransferase activity produces cysteine (Japanese Patent Laid-open (Kokai) No. 2002-233384). The ability to produce L-cysteine can also be increased by incorporating serine acetyltransferase which has been mutated to attenuate feedback inhibition by L-cysteine (Japanese Patent Laid-open No. 11-155571; U.S. Patent Published Application No. 20050112731; U.S. Pat. No. 6,218,168).

Furthermore, the ability to produce L-cysteine in a microorganism can be enhanced by suppressing the L-cysteine decomposition system. Examples of such microorganisms include coryneform bacteria or *Escherichia* bacteria in which the activity of cystathionine-β-lyase (Japanese Patent Laid-open No. 11-155571), tryptophanase (Japanese Patent Laid-open No. 2003-169668), or O-acetylserine sulfhydrylase B (Japanese Patent Laid-open No. 2005-245311) is attenuated or deleted.

Furthermore, the ydeD gene which encodes the YdeD protein participates in excretion of the metabolic products of the cysteine pathway (Dabler et al., Mol. Microbiol., 36, 1101-1112 (2000)). Also, techniques are known for enhancing L-cysteine-producing ability by increasing expression of the mar-locus, emr-locus, acr-locus, cmr-locus, mex-gene, bmr-gene or qacA-gene. These loci and/or genes encode proteins which cause secretion of toxic substances from cells (U.S. Pat. No. 5,972,663). The emrAB, emrKY, yojIH, acrEF, bcr, and cusA genes are further examples (Japanese Patent Laid-open No. 2005-287333).

An *Escherichia coli* has been reported which produces L-cysteine, and which has increased activity of the positive transcriptional control factor of the cysteine regulon encoded by the cysB gene (International Patent Publication WO01/27307).

Although the tolC gene (BioCyc Home Page, Summary of *Escherichia coli*, Strain K-12, version 11.6, *E. coli* K-12 Gene: tolC [searched on Feb. 11, 2008], Internet URL: biocyc.org/ECOLI/NEW-IMAGE?type=GENE&object=EG11009) is known as a gene coding for a porin (outer membrane channel), its relation to L-cysteine production is not known.

SUMMARY OF THE INVENTION

The present invention provides novel techniques for improving the ability to produce bacterial L-cysteine, and thereby providing an L-cysteine-producing bacterium, as well as a method for producing L-cysteine, L-cystine, their derivatives or precursors or a mixture of these by using such a bacterium.

The ability of a bacterium to produce L-cysteine is enhanced by modifying the bacterium so that the activity of the protein encoded by the tolC gene is increased.

It is an aspect of the present invention to provide a bacterium belonging to the family Enterobacteriaceae, which has the ability to produce L-cysteine and has been modified so that the activity of the protein encoded by a tolC gene is increased.

It is a further aspect of the present invention to provide the bacterium as described above, wherein the activity of the protein is increased by increasing expression amount of the tolC gene, increasing translation amount of the tolC gene, or combinations thereof.

It is a further aspect of the present invention to provide the bacterium as described above, wherein expression amount of the tolC gene is increased by increasing copy number of the tolC gene, or by modifying an expression control sequence of the gene.

It is a further aspect of the present invention to provide the bacterium as described above, wherein the protein is selected from the group consisting of:

(a) a protein comprising the amino acid sequence of SEQ ID NO: 2, (b) a protein comprising the amino acid sequence of SEQ ID NO: 2, but wherein one or several amino acid residues substituted, deleted, inserted or added, wherein the increase of the activity in the bacterium improves the ability to produce L-cysteine of the bacterium.

It is a further aspect of the present invention to provide the bacterium as described above, wherein the tolC gene is selected from the group consisting of:

(a) a DNA comprising the nucleotide sequence of SEQ ID NO: 1, (b) a DNA which hybridizes with the nucleotide sequence of SEQ ID NO: 1, or a probe prepared from the nucleotide sequence, under stringent conditions, and codes for a protein, wherein the increase of the activity in the bacterium improves the ability to produce L-cysteine of the bacterium.

It is a further aspect of the present invention to provide the bacterium as described above, which contains a mutant serine acetyltransferase in which feedback inhibition by L-cysteine has been attenuated.

It is a further aspect of the present invention to provide the bacterium as described above, wherein the activity of the protein encoded by the ydeD gene is increased.

It is a further aspect of the present invention to provide the bacterium as described above, wherein an activity of a protein having cysteine desulfhydrase activity decreases.

It is a further aspect of the present invention to provide the bacterium as described above, wherein the activity of the protein encoded by the ydeD gene is increased.

It is a further aspect of the present invention to provide the bacterium as described above, wherein an activity of a protein having cysteine desulfhydrase activity is decreased.

It is a further aspect of the present invention to provide the bacterium as described above, wherein an activity of a protein having cysteine desulfhydrase activity is decreased.

It is a further aspect of the present invention to provide the bacterium as described above, wherein activity of a protein having the cysteine desulfhydrase activity decreases.

It is a further aspect of the present invention to provide the bacterium as described above, wherein the protein having the cysteine desulfhydrase activity is tryptophanase.

It is a further aspect of the present invention to provide the bacterium as described above, which is an *Escherichia* bacterium.

It is a further aspect of the present invention to provide the bacterium as described above, which is *Escherichia coli*.

It is a further aspect of the present invention to provide a method for producing L-cysteine, L-cystine, a derivative or precursor thereof, or a mixture thereof, which comprises culturing the bacterium as described above in a medium and collecting L-cysteine, L-cystine, a derivative or precursor thereof, or a mixture thereof from the medium.

It is a further aspect of the present invention to provide the method as described above, wherein the derivative of L-cysteine is a thiazolidine derivative.

It is a further aspect of the present invention to provide the method as described above, wherein the precursor of L-cysteine is O-acetylserine or N-acetylserine.

DETAILED DESCRIPTION OF EXEMPLARY EMBODIMENTS

<1> Bacterium

Figure 1:
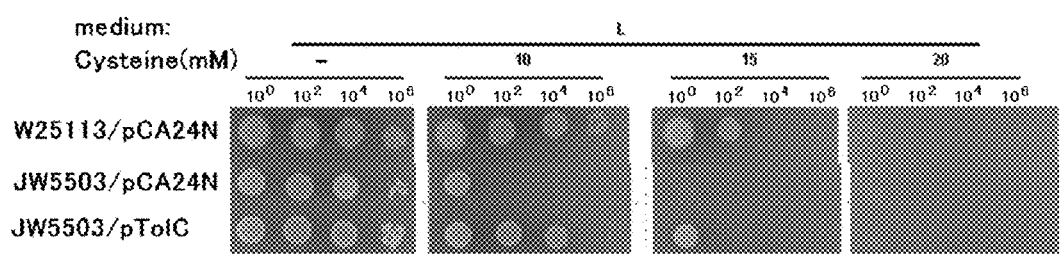
FIG. 1 shows the cysteine sensitivity of a strain which is deficient in a part of or the entire tolC gene and complementation (recovery of growth) with a tolC plasmid (photograph).

The bacterium belongs to the family Enterobacteriaceae, and is able to produce L-cysteine. Furthermore, the bacterium has been modified so that the activity of the protein encoded by the tolC gene is increased. The "ability to produce L-cysteine" or the "L-cysteine-producing ability" can mean an ability of the bacterium to produce L-cysteine and cause accumulation of L-cysteine in a medium or the bacterial cells in such an amount that the L-cysteine can be collected from the medium or cells when the bacterium is cultured in the medium. A bacterium having L-cysteine-producing ability can mean a bacterium which can produce and cause accumulation of L-cysteine as compared with a wild-type, parent, or unmodified strain, and can be a bacterium which can produce and cause accumulation of L-cysteine in a medium in an amount of, for example, 0.05 g/L or more, 0.1 g/L or more, or 0.2 g/L or more.

The L-cysteine produced by the bacterium can change into L-cystine in the medium by the formation of a disulfide bond. Furthermore, as described below, S-sulfocysteine can be generated by the reaction of L-cysteine and thiosulfuric acid in the medium (Szczepkowski T. W., Nature, vol. 182 (1958)). Moreover, the L-cysteine generated in bacterial cells can be condensed with a ketone, aldehyde, or, for example, pyruvic acid, which is present in the cells, to produce a thiazolidine derivative via a hemithioketal intermediate (refer to Japanese Patent No. 2992010). The thiazolidine derivative and hemithioketal can be present as an equilibrated mixture. Therefore, the ability to produce L-cysteine is not limited to the ability to accumulate only L-cysteine in the medium or cells, but also includes the ability to accumulate, L-cystine or its derivative or precursor, or a mixture thereof. Examples of the aforementioned derivative of L-cysteine or L-cystine include, for example, S-sulfocysteine, thiazolidine derivatives, hemithioketal, and so forth. Examples of the precursor of L-cysteine or L-cystine include, for example, O-acetylserine, which is a precursor of L-cysteine. The precursors of L-cysteine or L-cystine also include derivatives of the precursors, for example, N-acetylserine, which is a derivative of O-acetylserine, and so forth.

O-Acetylserine (OAS) is a precursor of L-cysteine biosynthesis. OAS is a metabolite of bacteria and plants, and is produced by acetylation of L-serine by an enzymatic reaction catalyzed by serine acetyltransferase (SAT). OAS is further converted into L-cysteine in cells.

The ability to produce L-cysteine can be inherent to the bacterium, or it can be imparted by modifying a microorganism such as those described below by mutagenesis or recombinant DNA techniques. Unless specially mentioned, the term L-cysteine refers to the reduced-type L-cysteine, L-cystine, a derivative or precursor such as those mentioned above, or a mixture thereof.

The bacterium is not particularly limited so long as the bacterium belongs to the family Enterobacteriaceae and has the ability to produce L-cysteine. Such bacteria include those of the genera *Escherichia, Enterobacter, Pantoea, Klebsiella, Serratia, Erwinia, Salmonella* and *Morganella*. Specifically, those classified into the family Enterobacteriaceae according to the taxonomy used in the NCBI (National Center for Biotechnology Information) database (www.ncbi.nlm.nih.gov/Taxonomy/Browser/wwwtax.cgi?id=91347) can be used. As the parent strain of the family Enterobacteriaceae, a bacterium of the genus *Escherichia, Enterobacter, Pantoea, Erwinia,* or *Klebsiella* can be used.

Although the *Escherichia* bacteria are not particularly limited, specifically, those described in the work of Neidhardt et al. (Backmann B. J., 1996, Derivations and Genotypes of some mutant derivatives of *Escherichia coli* K-12, p. 2460-2488, Table 1, In F. D. Neidhardt (ed.), *Escherichia coli* and *Salmonella* Cellular and Molecular Biology/Second Edition, American Society for Microbiology Press, Washington, D.C.) can be used. Among these, *Escherichia coli* is one example. Examples of *Escherichia coli* include *Escherichia coli* W3110 (ATCC 27325), *Escherichia coli* MG1655 (ATCC 47076), and so forth, and include those derived from the prototype wild-type strain, K12 strain.

These strains are available from, for example, American Type Culture Collection (Address: P.O. Box 1549, Manassas, Va. 20108, United States of America). That is, registration numbers are given to each of the strains, and the strains can be ordered by using these registration numbers (refer to www.atcc.org/). The registration numbers of the strains are listed in the catalogue of the American Type Culture Collection.

Examples of the *Enterobacter* bacteria include *Enterobacter agglomerans, Enterobacter aerogenes* and so forth, and examples of the *Pantoea* bacteria include *Pantoea ananatis*. Some strains of *Enterobacter agglomerans* were recently reclassified into *Pantoea agglomerans*, *Pantoea ananatis*, or *Pantoea stewartii* on the basis of nucleotide sequence analysis of 16S rRNA etc. A bacterium belonging to either *Enterobacter* or *Pantoea* can be used so long as it is classified as the family Enterobacteriaceae.

In particular, *Pantoea* bacteria, *Erwinia* bacteria, and *Enterobacter* bacteria are classified as γ-proteobacteria, and they are taxonomically very close to one another (J. Gen. Appl. Microbiol., 1997, 43, 355-361; International Journal of Systematic Bacteriology, October 1997, pp. 1061-1067). In recent years, some bacteria belonging to the genus *Enterobacter* were reclassified as *Pantoea agglomerans*, *Pantoea dispersa*, or the like, on the basis of DNA-DNA hybridization experiments etc. (International Journal of Systematic Bacteriology, July 1989, 39(3), pp. 337-345). Furthermore, some bacteria belonging to the genus *Erwinia* were reclassified as *Pantoea ananas* or *Pantoea stewartii* (refer to International Journal of Systematic Bacteriology, January 1993, 43(1), pp. 162-173).

Examples of the *Enterobacter* bacteria include, but are not limited to, *Enterobacter agglomerans*, *Enterobacter aerogenes*, and so forth. Specifically, the strains exemplified in European Patent Publication No. 952221 can be used.

A typical strain of the genus *Enterobacter* is the *Enterobacter agglomeranses* ATCC 12287 strain.

Typical strains of the *Pantoea* bacteria include, but are not limited to, *Pantoea ananatis*, *Pantoea stewartii*, *Pantoea agglomerans*, and *Pantoea citrea*.

Specific examples of *Pantoea ananatis* include the *Pantoea ananatis* AJ13355 strain and SC17 strain. The SC17 strain was selected as a low phlegm-producing mutant strain from the AJ13355 strain (FERM BP-6614), which was isolated from soil in Iwata-shi, Shizuoka-ken, Japan for its ability to proliferate in a low pH medium containing L-glutamic acid and a carbon source (U.S. Pat. No. 6,596,517).

The *Pantoea ananatis* AJ13355 strain was deposited at the National Institute of Bioscience and Human-Technology, Agency of Industrial Science and Technology, Ministry of International Trade and Industry (currently, the National Institute of Advanced Industrial Science and Technology, International Patent Organism Depositary, Address: Tsukuba Central 6, 1-1, Higashi 1-Chome, Tsukuba-shi, Ibaraki-ken, 305-8566, Japan) on Feb. 19, 1998 and assigned an accession number of FERM P-16644. It was then converted to an international deposit under the provisions of Budapest Treaty on Jan. 11, 1999 and assigned an accession number of FERM BP-6614. This strain was identified as *Enterobacter agglomerans* when it was isolated and deposited as the *Enterobacter agglomerans* AJ13355 strain. However, it was recently reclassified as *Pantoea ananatis* on the basis of nucleotide sequencing of 16S rRNA and so forth.

Examples of the *Erwinia* bacteria include, but are not limited to, *Erwinia amylovora* and *Erwinia carotovora*, and examples of the *Klebsiella* bacteria include *Klebsiella planticola*.

Impartation or Enhancement of L-Cysteine-Producing Ability

Hereinafter, methods for imparting the ability to produce L-cysteine to bacteria belonging to Enterobacteriaceae, or methods for enhancing the ability to produce L-cysteine of such bacteria, are described.

To impart the ability to produce L-cysteine, methods conventionally employed in the breeding of coryneform bacteria or bacteria of the genus *Escherichia* (see "Amino Acid Fermentation", Gakkai Shuppan Center (Ltd.), 1st Edition, published May 30, 1986, pp. 77-100) can be used. Such methods include acquiring the properties of an auxotrophic mutant, an analogue-resistant strain, or a metabolic regulation mutant, or constructing a recombinant strain so that it overexpresses an L-cysteine biosynthesis enzyme. Here, in the breeding of L-cysteine-producing bacteria, one or more of the above-described properties such as auxotrophy, analogue resistance, and metabolic regulation mutation can be imparted. The expression of L-cysteine biosynthesis enzyme(s) can be enhanced alone or in combinations of two or more. Furthermore, the methods of imparting properties such as an auxotrophy, analogue resistance, or metabolic regulation mutation can be combined with enhancement of the biosynthesis enzymes.

An auxotrophic mutant strain, L-cysteine analogue-resistant strain, or metabolic regulation mutant strain with the ability to produce L-cysteine can be obtained by subjecting a parent, wild-type, or unmodified strain to conventional mutatagenesis, such as exposure to X-rays or UV irradiation, or by treating them with a mutagen such as N-methyl-N'-nitro-N-nitrosoguanidine or ethyl methanesulfonate (EMS), then selecting those which exhibit autotrophy, analogue resistance, or a metabolic regulation mutation and which also have the ability to produce L-cysteine from the obtained mutant strains.

Specific examples of L-cysteine-producing bacteria include, but are not limited to, *E. coli* JM15 transformed with multiple kinds of cysE gene alleles encoding serine acetyltransferase (SAT) resistant to feedback inhibition (U.S. Pat. No. 6,218,168), *E. coli* W3110 in which a gene encoding a protein responsible for excretion of cytotoxic substances is overexpressed (U.S. Pat. No. 5,972,663), an *E. coli* strain having decreased cysteine desulfhydrase activity (Japanese Patent Laid-open No. 11-155571), and *E. coli* W3110 with increased activity of the positive transcriptional control factor of the cysteine regulon encoded by the cysB gene (WO01/27307).

The following proteins are known to have the cysteine desulfhydrase activity of *E. coli*: cystathionine-β-lyase (metC product, Japanese Patent Laid-open No. 11-155571, Chandra et al., Biochemistry, 21 (1982) 3064-3069), tryptophanase (tnaA product, Japanese Patent Laid-open No. 2003-169668, Austin Newton et al., J. Biol. Chem., 240 (1965) 1211-1218)), O-acetylserine sulfhydrylase B (cysM gene product, Japanese Patent Laid-open No. 2005-245311) and the malY gene product (Japanese Patent Laid-open No. 2005-245311). By decreasing the activities of these proteins, L-cysteine-producing ability is improved.

The phrase "decreasing activity of a protein" can mean that activity of the protein is decreased as compared with a non-modified strain such as a wild-type or parent strain, and also can mean the complete disappearance of the activity.

Decreasing the activity of a protein having the cysteine desulfhydrase activity can be attained by, for example, reducing the expression of a gene coding for the protein. Specifically, for example, intracellular activity of the protein can be reduced by deleting a part of or the entire coding region of the target gene on the chromosome. Expression of a target gene can also be decreased by modifying an expression control sequence of the gene such as the promoter and the Shine-Dalgarno (SD) sequences. Furthermore, the expression of the gene can also be reduced by modifying a non-translated region other than the expression control sequence. Additionally, the entire gene as well as the sequences on both sides of the gene on the chromosome can be deleted. Moreover, modification can also be attained by introducing an amino acid substitution (missense mutation), a stop codon (nonsense mutation), or a frame shift mutation which adds or deletes one or two nucleotides into the coding region of the target gene on the chromosome (Journal of Biological Chemistry, 272: 8611-8617 (1997); Proceedings of the National Academy of Sciences, USA, 95 5511-5515 (1998); Journal of Biological Chemistry, 266, 20833-20839 (1991)).

Furthermore, modification can be caused by a conventional mutagenesis based on X-ray or ultraviolet irradiation or the use of a mutagen such as N-methyl-N'-nitro-N-nitrosoguanidine, as long as the activity of the target protein is decreased.

Modification of an expression control sequence is performed, for example, for one or more nucleotides, two or more nucleotides, or three or more nucleotides. When a coding region is deleted, the region to be deleted can be an N-terminus region, an internal region or a C-terminus region, or even the entire coding region, so long as the function of the target protein is decreased or deleted. Deletion of a longer region is more likely to inactivate a gene. Furthermore, reading frames upstream and downstream of the region to be deleted can be dissimilar.

When another sequence is inserted into a coding region of a target gene, the sequence can be inserted into any region of the gene, and insertion of a longer sequence is more likely to inactivate the gene. Reading frames upstream and downstream of the insertion site can be dissimilar. The other sequence is not particularly limited so long as a sequence which decreases or deletes function of the encoded protein is chosen, and examples include a transposon carrying an antibiotic resistance gene, a gene useful for L-cysteine production, and so forth.

A target gene on the chromosome can be modified as described above by, for example, preparing a deletion-type version of the gene in which a partial sequence of the gene is deleted so that the deletion-type gene does not produce a normally-functioning protein. Then, a bacterium can be transformed with a DNA containing the deletion-type gene to cause homologous recombination between the deletion-type gene and the native gene on the chromosome, which results in the substitution of the deletion-type gene for the gene on the genome. The protein encoded by the deletion-type gene has a conformation different from that of the wild-type enzyme protein, if it is even produced, and thus, the function is reduced or deleted. Such gene disruption based on gene substitution utilizing homologous recombination is known, and examples include Red-driven integration (Datsenko, K. A., and Wanner, B. L., Proc. Natl. Acad. Sci. USA, 97:6640-6645 (2000)), methods using a linear DNA such as the method of utilizing Red driven integration in combination with an excision system derived from λ phage (Cho, E. H., Gumport, R. I., Gardner, J. F., J. Bacteriol., 184:5200-5203 (2002)) (refer to WO2005/010175), methods using a plasmid containing a temperature sensitive replication origin or a plasmid capable of conjugative transfer, methods utilizing a suicide vector without a replication origin in a host (U.S. Pat. No. 6,303,383, Japanese Patent Laid-open No. 05-007491), and so forth.

Decrease of the expression of a target gene can be confirmed by comparing the amount of mRNA transcribed from the gene with that in a wild-type strain or non-modified strain. The expression amount can be confirmed by Northern hybridization, RT-PCR (Molecular Cloning (Cold Spring Harbor Laboratory Press, Cold Spring Harbor (USA), 2001)), and the like.

A decrease in the amount of a target protein can be confirmed by Western blotting using antibodies (Molecular Cloning (Cold Spring Harbor Laboratory Press, Cold Spring Harbor (USA), 2001)).

The L-cysteine-producing bacterium can have a SAT which has been mutated to be resistant to feedback inhibition. The following mutations in SAT are known to induce resistance to feedback inhibition and are derived from *Escherichia coli*: when the methionine residue at position 256 is replaced with a glutamate residue (Japanese Patent Laid-open No. 11-155571), when the methionine residue at position 256 is replaced with an isoleucine residue (Denk, D. and Boeck, A., J. General Microbiol., 133, 515-525 (1987)), a mutation in the region from the amino acid residue at position 97 to the amino acid residue at position 273 or a deletion of the C-terminus region from the amino acid residue at position 227 (International Patent Publication WO97/15673, U.S. Pat. No. 6,218, 168), when the amino acid sequence corresponding to positions 89 to 96 of the wild-type SAT contains one or more mutations (U.S. Patent Published Application No. 20050112731(A1)), and so forth. In the cysE5 gene which encodes the mutant SAT described in the examples, the Val residue and the Asp residue at positions 95 and 96 of the wild-type SAT are replaced with an Arg residue and a Pro residue, respectively.

The SAT gene is not limited to the gene of *Escherichia coli*, but can be any gene encoding a protein having the SAT activity. For example, a SAT isozyme of *Arabidopsis thaliana* desensitized to feedback inhibition by L-cysteine is known, and the gene encoding this SAT can also be used (FEMS Microbiol. Lett., 179 (1999) 453-459).

If a gene encoding a mutant SAT is introduced into a bacterium, the ability to produce L-cysteine is imparted to the bacterium. To introduce a mutant SAT gene into a bacterium, various vectors which are typically used for protein expression can be used. Examples of such vectors include pUC19, pUC18, pHSG299, pHSG399, pHSG398, RSF1010, pBR322, pACYC184, pMW219, and so forth.

In order to introduce a recombinant vector containing a SAT gene into a bacterium, methods which are typically used to transform bacteria can be used, such as the method of D. A. Morrison (Methods in Enzymology, 68, 326 (1979)), treating recipient cells with calcium chloride to increase permeability of the cells for DNA (Mandel, M. and Higa, A., J. Mol. Biol., 53, 159 (1970)), and a method based on electroporation.

Furthermore, the SAT activity can also be enhanced by increasing the copy number of the SAT gene. The copy number of the SAT gene can be increased by introducing the SAT gene into a bacterium by using a vector such as those described above, or by introducing multiple copies of the SAT gene onto the chromosomal DNA of a bacterium. Multiple copies of the SAT gene are introduced by homologous recombination which targets a sequence present on the chromosomal DNA in multiple copies. A repetitive DNA or inverted repeat present at the end of a transposable element can be used as a sequence which is present on the chromosomal DNA in multiple copies. Alternatively, as disclosed in Japanese Patent Laid-open No. 2-109985, multiple copies of the SAT gene can be introduced into the chromosomal DNA by incorporating them into a transposon and transferring it.

Moreover, it is known that the ydeD gene coding for the YdeD protein participates in secretion of metabolic products of the cysteine pathway, and the ability to produce L-cysteine can also be improved by enhancing the activity of the YdeD protein (Japanese Patent Laid-open No. 2002-233384). Modification for increasing the activity of the YdeD protein can be attained, for example, by improving expression of the ydeD gene. Improvement of the expression of the ydeD gene can be attained in the same manner as that of the improvement of expression of the tolC gene described later.

The ydeD gene of *Escherichia coli* can be obtained from *Escherichia coli* chromosomal DNA by PCR using, for example, the primers having the nucleotide sequences of SEQ ID NOS: 9 and 10.

Furthermore, by incorporating 3-phosphoglycerate dehydrogenase (PGD) desensitized to the feedback inhibition by serine, the ability to produce L-cysteine can also be improved. The serA5 gene is known as a gene coding for such a mutant PGD (described in U.S. Pat. No. 6,180,373).

Additionally, an L-cysteine-producing Escherichia bacterium which has been modified to enhance expression of the cysPTWAM cluster genes coding for the sulfate/thiosulfate transport system proteins (Japanese Patent Laid-open No. 2005-137369, EP 1528108) can also be used.

Moreover, an Escherichia bacterium which has the ability to produce L-cysteine and has been modified to increase expression of the emrAB, emrKY, yojIH, acrEF, bcr or cusA gene (Japanese Patent Laid-open No. 2005-287333) can also be used.

Particular examples of the bacteria having the ability to produce L-cysteine include a bacterium containing a mutant SAT resistant to feedback inhibition, a bacterium having enhanced activity of the YdeD protein, a bacterium deficient in the cysteine desulfhydrase activity, a bacterium containing a mutant SAT resistant to feedback inhibition and having enhanced activity of the YdeD protein, a bacterium containing a mutant SAT resistant to feedback inhibition and deficient in the cysteine desulfhydrase activity, a bacterium having enhanced activity of the YdeD protein and deficient in the cysteine desulfhydrase activity, and a bacterium containing a mutant SAT resistant to feedback inhibition, deficient in the cysteine desulfhydrase activity, and having enhanced activity of the YdeD protein. The cysteine desulfhydrase activity can be the tryptophanase activity.

The bacterium can be obtained by modifying a bacterium belonging to the family Enterobacteriaceae, which has the ability to produce L-cysteine such as those described above, so that the activity of the protein encoded by tolC gene (henceforth also referred to as "TolC") is increased. Alternatively, after the performance of such a modification where the activity of the TolC protein is increased, the ability to produce L-cysteine can be imparted.

The tolC gene is the same as ECK3026, weeA, b3035, colE1-i, mtcB, mukA, refI and toc genes.

The phrase "the activity of the protein encoded by the tolC gene is increased" can mean that the activity of the TolC protein encoded by the tolC gene is increased as compared with a non-modified strain such as a wild-type or parent strain.

Specifically, the activity of the TolC protein can mean an activity in which an increase in the bacterium improves its ability to produce L-cysteine. Furthermore, the TolC protein increases cysteine resistance as compared with a non-modified strain when expression of the protein is enhanced, as described in the example section. Therefore, according to another definition, the activity of the TolC protein can mean such an activity of increasing cysteine resistance.

Modification for increasing the activity of the TolC protein encoded by the tolC gene is attained, for example, by increasing expression of the tolC gene.

To enhance the expression of the tolC gene, the copy number of the tolC gene can be increased by using a gene recombination technique. For example, a recombinant DNA can be prepared by ligating a gene fragment containing the tolC gene with a vector functioning in a host bacterium, such as a multi-copy type vector, and then introduced into the bacterium to transform it.

Examples of the vector include vectors which are autonomously replicable in host bacterium cells. Examples of the vectors autonomously replicable in Escherichia coli cells include pUC19, pUC18, pHSG299, pHSG399, pHSG398, pACYC184 (pHSG and pACYC series vectors are available from Takara Bio), RSF1010, pBR322, pMW219 (pMW219 is available from NIPPON GENE), pSTV29 (available from Takara Bio), and so forth.

To introduce such a recombinant DNA into a bacterium, any known reported transformation methods can be employed. For instance, the method of treating recipient cells with calcium chloride so as to increase permeability thereof for DNA, has been reported for Escherichia coli K-12 (Mandel, M. and Higa, A., J. Mol. Biol., 53, 159 (1970)), and the method of preparing competent cells from cells which are at the growth phase followed by introducing the DNA thereinto, has been reported for Bacillus subtilis (Duncan, C. H., Wilson, G. A. and Young, F. E., Gene, 1, 153 (1977)). In addition to these is the method of making DNA-recipient cells into protoplasts or spheroplasts, which can easily take up recombinant DNA, followed by introducing the recombinant DNA into the DNA recipient cells, which is known to be applicable to Bacillus subtilis, actinomycetes and yeasts (Chang, S. and Choen, S. N., Mol. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci. USA, 75, 1929 (1978)).

Increase of the copy number of the tolC gene can also be achieved by introducing multiple copies of the tolC gene into a genomic DNA of a bacterium. In order to introduce multiple copies of the tolC gene into a genomic DNA of a bacterium, homologous recombination is carried out by using a sequence whose multiple copies are present in the genomic DNA as targets. Sequences whose multiple copies are present in genomic DNA can be used, such as repetitive DNA, and inverted repeats existing at the end of a transposable element. Another tolC gene can be introduced beside the tolC gene existing on a genome in tandem, or it can be introduced into an unnecessary gene on a genome in a plural number. Such gene transfer can be attained by using a temperature sensitive vector or an integration vector.

Alternatively, as disclosed in Japanese Patent Laid-open No. 2-109985, it is also possible to incorporate the tolC gene into a transposon, and allow it to transfer to introduce multiple copies of the genes into a genomic DNA. Transfer of the gene to the genome can be confirmed by performing Southern hybridization using a part of the tolC gene as a probe.

Furthermore, in addition to the aforementioned increase of the gene copy number, expression of the tolC gene can also be enhanced by replacing an expression control sequence such as a promoter of the tolC gene on a genome DNA or plasmid with a stronger one, by making the −35 and −10 regions of the gene closer to the consensus sequence, by amplifying a regulator that increases expression of the tolC gene, or by deleting or attenuating a regulator that decreases expression of the tolC gene according to the methods described in International Patent Publication WO00/18935. For example, the lac promoter, trp promoter, trc promoter, tac promoter, araBA promoter, lambda phage PR promoter and PL promoter, tet promoter, T7 promoter, Φ10 promoter, and so forth, are known as strong promoters. Furthermore, the promoter of the threonine operon of E. coli can also be used. A promoter or SD region of the tolC gene can also be modified so as to become stronger by introducing a nucleotide substitution or the like. Examples of methods for evaluating strength of a promoter and strong promoters are described in the paper of Goldstein et al. (Prokaryotic promoters in biotechnology, Biotechnol. Annu. Rev., 1, 105-128 (1995)), and so forth. Additionally, it is known that substitution of several nucleotides in a spacer between the ribosome-binding site (RBS) and the translation initiation codon, especially a sequence immediately upstream from the initiation codon, greatly affects mRNA translation efficiency, and therefore, this sequence can be modified. Expression control regions such as the promoter of the tolC gene can also be identified by using a promoter probe vector or gene analysis software such as GENETYX. By such substitution or modification of the promoter as described above, expression of the tolC gene is enhanced. Substitution of an expression control sequence can also be attained, for example, by a method using a temperature sensitive plasmid or Red-driven integration (WO2005/010175).

The nucleotide sequence of the tolC gene of *Escherichia coli* and the amino acid sequence encoded by this gene are shown in SEQ ID NOS: 1 and 2, respectively.

Since the nucleotide sequence of the tolC gene can be different depending on the species or strain of the bacterium, the tolC gene to be modified can be a variant of the nucleotide sequence of SEQ ID NO: 1. Homologues of TolC are known for many bacteria, and can be found by a search of databases. When proteins highly homologous to the TolC protein of the *E. coli* K-12 strain are searched for on the basis of sequence information, the search can be performed, for example, as a BLAST search (www.ncbi.nlm.nih.gov/blast/Blast.cgi). Furthermore, when homologues are searched for with a keyword, if the search engine of Entrez (www.ncbi.nlm.nih.gov/sites/gquery) is used, and a term "tolC" or "outer membrane channel protein" is entered as a keyword, for example, candidate sequences are retrieved from plural databases. By scrutinizing these candidates, objective homologue sequences can be found. Nucleotide sequences of genes and amino acid sequences of TolC homologues of the following bacteria are shown in SEQ ID NOS: 11 to 30, as among the many TolC homologues found by such a method. The accession numbers in the NCBI (National Center for Biotechnology Information) database and identity (%) with respect to the amino acid sequence of SEQ ID NO: 2 are shown in the parentheses.

*Shigella boydii* Sb227 (NCBI accession: YP_409239, 99%) *Shigella flexneri* 2a str. 2457T (NCBI accession: NP_838556, Identity: 99%)

*Salmonella enterica* subsp. *enterica* serovar *Typhi* Ty2 (NCBI accession: NP_806790, 89%)

*Citrobacter koseri* ATCC BAA-895 (NCBI accession: YP_001455919, 89%)

*Klebsiella pneumoniae* subsp. *pneumoniae* MGH 78578 (NCBI accession: YP_001337075, 83%)

*Enterobacter sakazakii* ATCC BAA-894 (NCBI accession: YP_001436507, 80%)

*Erwinia carotovora* subsp. *atroseptica* SCRI1043 (NCBI accession: YP_048456, 76%)

*Serratia proteamaculans* 568 (NCBI accession: YP_001480490, 73%)

*Aeromonas salmonicida* subsp. *salmonicida* A449 (NCBI accession: ABO88689, 51%)

*Vibrio vulnificus* YJ016 (NCBI accession: NP_933376, 45%)

The tolC gene can also be a gene encoding a protein having a sequence corresponding to the amino acid sequence of the aforementioned TolC protein or TolC homologue, but which includes substitutions, deletions, insertions, additions, or the like, of one or several amino acid residues at one or several positions. Although the number of the "one or several" amino acid residues can differ depending on their position in the three-dimensional structure or the types of amino acid residues of the proteins, specifically, for example, it can be 1 to 20, 1 to 10, or 1 to 5. These substitutions, deletions, insertions, or additions of one or several amino acid residues can be conservative mutations so as to preserve the normal function of the protein. Typical examples of the conservative mutations are conservative substitutions. Conservative substitutions include a mutation wherein substitution takes place mutually among Phe, Trp and Tyr, if the substitution site is an aromatic amino acid; among Leu, Ile and Val, if the substitution site is a hydrophobic amino acid; between Gln and Asn, if it is a polar amino acid; among Lys, Arg and His, if it is a basic amino acid; between Asp and Glu, if it is an acidic amino acid; and between Ser and Thr, if it is an amino acid having a hydroxyl group. Specific examples of conservative substitutions include: substitution of Ser or Thr for Ala; substitution of Gln, His or Lys for Arg; substitution of Glu, Gln, Lys, His or Asp for Asn; substitution of Asn, Glu or Gln for Asp; substitution of Ser or Ala for Cys; substitution of Asn, Glu, Lys, His, Asp or Arg for Gln; substitution of Gly, Asn, Gln, Lys or Asp for Glu; substitution of Pro for Gly; substitution of Asn, Lys, Gln, Arg or Tyr for His; substitution of Leu, Met, Val or Phe for Ile; substitution of Ile, Met, Val or Phe for Leu; substitution of Asn, Glu, Gln, His or Arg for Lys; substitution of Ile, Leu, Val or Phe for Met; substitution of Trp, Tyr, Met, Ile or Leu for Phe; substitution of Thr or Ala for Ser; substitution of Ser or Ala for Thr; substitution of Phe or Tyr for Trp; substitution of His, Phe or Trp for Tyr; and substitution of Met, Ile or Leu for Val. The above-mentioned amino acid substitution, deletion, insertion, addition, inversion, etc., can be a result of a naturally occurring mutation or variation due to an individual difference, or a difference of species of a microorganism as an origin of gene (mutant or variant).

Furthermore, the gene having such a conservative mutation as mentioned above can be a gene encoding a protein showing a homology, for example, of 80% or more, 90% or more, 95% or more, 97% or more, 98% or more, or 99% or more, to the entire encoded amino acid sequence, and having a function equivalent to that of a wild-type TolC protein.

The tolC gene can be a DNA which hybridizes with a probe prepared from known gene sequences, for example, the aforementioned nucleotide sequence, or sequences complementary to the sequences under stringent conditions and which encodes a protein which is a functional equivalent to the TolC protein. The term "stringent conditions" refers to conditions where a so-called specific hybrid is formed and a non-specific hybrid is not formed. Examples thereof include conditions where DNAs having high a homology, for example, of 80% or more, 90% or more, 95% or more, 97% or more, 98% or more, or 99% or more, hybridize with each other and DNAs having a homology less than the value do not hybridize with each other; and specifically include conditions corresponding to a salt concentration and temperature of washing which are typical of Southern hybridization, that is, washing once or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C., for example.

The probe can be a partial sequence of a complementary sequence of the gene. Such a probe can be prepared by PCR using oligonucleotides prepared based on the known nucleotide sequences of genes as primers, and a DNA fragment containing these nucleotide sequences as the template. When a DNA fragment of a length of about 300 bp is used as the probe, the conditions of washing after hybridization can be, for example, 50° C., 2×SSC, and 0.1% SDS.

The above descriptions about variants of genes and proteins are similarly applied to enzymes such as serine acetyltransferase and cysteine desulfhydrase, the YdeD protein, and the genes that code for them.

<2> Method for Producing L-Cysteine, L-Cystine, Derivatives or Precursors Thereof or Mixture Thereof These compounds can be produced by culturing the bacterium obtained as described above in a medium, and collecting L-cysteine, L-cystine, derivatives or precursors thereof or a mixture thereof from the medium. Examples of a derivative or precursor of L-cysteine include S-sulfocysteine, a thiazolidine derivative, a hemithioketal corresponding to the thiazolidine derivative mentioned above, O-acetylserine, N-acetylserine, and so forth.

Examples of the medium used for the culture can include ordinary media containing a carbon source, nitrogen source, sulfur source, inorganic ions, and other organic components as required.

As the carbon source, saccharides such as glucose, fructose, sucrose, molasses and starch hydrolysate, and organic acids such as fumaric acid, citric acid and succinic acid can be used.

As the nitrogen source, inorganic ammonium salts such as ammonium sulfate, ammonium chloride and ammonium phosphate, organic nitrogen such as soybean hydrolysate, ammonia gas, aqueous ammonia and so forth can be used.

As the sulfur source, inorganic sulfur compounds, such as sulfates, sulfites, sulfides, hyposulfites and thiosulfates can be examples.

As organic trace amount nutrients, required substances such as vitamin $B_1$, yeast extract and so forth can be added in appropriate amounts. Other than these, potassium phosphate, magnesium sulfate, iron ions, manganese ions and so forth are added in small amounts.

The culture can be performed under aerobic conditions for 30 to 90 hours. The culture temperature can be controlled to be at 25° C. to 37° C., and pH can be controlled to be 5 to 8 during the culture. To adjust the pH, inorganic or organic, acidic or alkaline substances, ammonia gas, and so forth, can be used. Collection of L-cysteine from the culture can be attained by, for example, any combination of usual ion exchange resin methods, precipitation, and other known methods.

L-cysteine obtained as described above can be used to produce L-cysteine derivatives. The cysteine derivatives include methylcysteine, ethylcysteine, carbocysteine, sulfocysteine, acetylcysteine, and so forth.

Furthermore, when a thiazolidine derivative of L-cysteine is accumulated in the medium, L-cysteine can be produced by collecting the thiazolidine derivative from the medium to break the reaction equilibrium between the thiazolidine derivative and L-cysteine so that L-cysteine is excessively produced.

Moreover, when S-sulfocysteine is accumulated in the medium, it can be converted into L-cysteine by reduction with a reducing agent such as dithiothreitol.

As shown in the example section described later, a tolC gene-deficient strain is more sensitive to L-cysteine as compared to a non-modified strain. Furthermore, a tolC gene-deficient strain also shows sensitivity to O-acetylserine (OAS) and N-acetylserine (NAS). On the basis of these results, TolC is considered to be an outer membrane secretion factor for secreting not only L-cysteine, but also NAS and OAS. Therefore, enhancement of the TolC activity is considered to provide high production of not only L-cysteine, but also NAS and OAS.

Methods for producing OAS by fermentation are described in Japanese Patent Laid-open Nos. 11-56381 and 2002-262896. In order to increase OAS production by fermentation, a mutant SAT in which feedback inhibition is reduced can be incorporated into a bacterium, and the activity of an inner membrane secretion pump the YdeD can be increased thereby excreting OAS from inside of the cells to outside of the cells via an inner membrane (Dabler, T. et al., Mol. Microbiol., 36, 1101-1112 (2000)). Therefore, a bacterium having a mutant SAT and showing increased activity of the YdeD protein is also suitable for production of OAS (Japanese Patent Laid-open No. 2002-262896), and such a bacterium especially constitutes an embodiment of the bacterium in accordance with the presently disclosed subject matter. A bacterium showing increased TolC activity, having a mutant SAT and showing increased activity of YdeD protein is more suitable for production of OAS. An example of such a bacterium includes the E. coli MG1655ΔtnaA::Km$^r$/pCEM256I/pYdeD/pLSTolC, shown in the example section. Although a factor of the inner membrane relating to the provision of high concentration and secretion of intracellular OAS was known, any effective factor for making OAS efficiently penetrate the outer membrane and secrete it in a medium has not been known so far. This is also the same for L-cysteine. Development of an effective means for enabling efficient penetration through the outer membrane has been a common objective for L-cysteine and OAS, and it is considered that it can be achieved for both by enhancement of the TolC activity.

Since OAS is a relatively unstable compound, it can be converted into NAS by an irreversible chemical reaction during culture. Therefore, in fermentation performed under neutral or approximately neutral conditions, NAS formed from OAS by the natural reaction can also be accumulated in the medium together with OAS in an intermingled state. When OAS is mainly produced by fermentation, for example, a method of maintaining pH of the medium to be in an acidic region can be used (Japanese Patent Laid-open No. 2002-262896). Furthermore, when NAS is mainly produced, NAS can be produced from OAS by the natural reaction, by maintaining pH of the medium to be in the alkali region.

By culturing the bacterium in accordance with the presently disclosed subject matter in a medium under suitable conditions, and collecting NAS and/or OAS accumulating in the medium, NAS and/or OAS can be produced. As the medium used for the culture, such media as described above, for example, the L-cysteine production medium described in the example section and the production medium described in Japanese Patent Laid-open No. 2002-262896, can be used. A substance that promotes the intracellular reaction for converting OAS to L-cysteine, such as thiosulfuric acid, cannot be added to the medium, in order to produce more OAS. Conditions suitable for the production can be determined by measuring the quantity of NAS and/or OAS accumulated in the medium. NAS and/or OAS can be quantified by HPLC using a hydrophobic column and a UV detector, or the like. As described above, OAS can be converted into NAS during the culture or quantification. Therefore, for evaluation of fermentation result, the fermentation products can be determined as the sum of OAS and NAS by converting all OAS produced by fermentation into NAS, and measuring the amount of NAS by HPLC. In order to convert all OAS into NAS, for example, the medium can be adjusted to an alkali pH by mixing the medium with 200 mM Tris buffer (pH 9.0) (Japanese Patent Laid-open No. 2002-262896).

EXAMPLES

Hereinafter, the present invention will be explained more specifically with reference to the following non-limiting examples. In the following descriptions, cysteine means L-cysteine.

(1) Screening of Clones Showing Cysteine Sensitivity

In order to comprehensively search for genes participating in cysteine resistance, the Keio collection (single gene-knock out library except for essential genes of E. coli BW25113, Baba, T, et al., 2006, Mol. Syst. Biol., 2:2006.0008) was screened for clones showing sensitivity to cysteine.

(1-1) Screening of Keio Collection for Clones Showing Cysteine Sensitivity

The 3,985 clones of the Keio collection were cultured at 37° C. for 15 hours in 0.5 ml of LB liquid medium. This culture medium was stamped on LB agar media containing cysteine at different concentrations (0, 15, 20, 25 mM), and culture was performed overnight at 37° C. Clones that were sensitive to cysteine at a concentration not higher than the growth inhibition concentration of cysteine for wild-type strains (20 mM) were visually selected. Specifically, clones that did not form colonies on the LB plate containing 15 mM cysteine were selected as candidates. A strain which is deficient in a part of or the entire tolC gene was obtained as a clone showing particularly strong and distinctive cysteine sensitivity among the above candidates. TolC is an example of a protein called a porin, which localizes in the outer membrane and forms a channel for substance transportation via the outer membrane. Although the presence of many other porins was known for E. coli, TolC was the only porin selected by this screening, among the several candidates considered showing strong cysteine sensitivity.

Strains deficient in OmpA, OmpC, OmpF, OmpG, OmpN, OmpT, OmpX, LamB or BtuB, which are also known examples of porins, did not show cysteine sensitivity at all. Since cysteine is a highly toxic amino acid, a possibility is estimated that TolC can promote transportation (secretion) of cysteine and cysteine-related substances, and thereby cysteine resistance is acquired. Most of the factors known so far to participate in transportation of cysteine and cysteine-related substances, YdeD (Dassler, T. et al., Mol. Microbiol., 2000; 36:1101-1112), YfiK (Franke, I. et al., J. Bacteriol., 2003; 185:1161-1166), CydDC (Pittman, Marc S. et al., J. Biol. Chem., December 2002; 277:49841-49849), and multidrug efflux pump (Yamada, S., et al., Appl. Envir. Microbiol., July 2006; 72:4735-4742), are factors of the inner membrane, and it was known that a secretion factor was required for penetration of the inner membrane. However, it is not known whether a porin (outer membrane channel), such as TolC, is required for penetration of a low molecule amino acid, such as cysteine, through the outer membrane. Moreover, it was an unexpected result that only TolC was particularly selected as a candidate by the screening among many porins, and a possible explanation was because only TolC was a central factor of the transportation of cysteine.

(1-2) Cysteine Sensitivity Induced by tolC Gene Deficiency

Since a strain which is deficient in a part of or the entire tolC gene was obtained by the screening of the Keio Collection, growth of the gene-deficient strain was observed on the agar medium containing cysteine of different concentrations in order to analyze the sensitivity of that strain to cysteine in more detail. The strain which is deficient in a part of or the entire tolC gene used here was the JW5503 strain (Keio collection), and the parent strain thereof was the BW25113 strain (Andreas Haldimann, A. and Wanner, B. L., J. Bacteriol., 2001 November; 183 (21):6384-6393). The plasmid carrying the tolC gene for a complementation experiment was pTolC (ASKA clone, Kitagawa, M, et al., 2005; DNA Res., 12:291-299), and the vector used as the base thereof was pCA24 (vector for ASKA clone, Kitagawa, M, et al., 2005, DNA Res., 12:291-299).

The bacteria containing each of the plasmids were each inoculated into 5 ml of L medium (10 g/L of Bacto trypton, 5 g/L of Bacto yeast extract, 5 g/L of NaCl), and cultured overnight at 37° C. The culture was serially diluted 10 times for every dilution with 0.9% physiological saline to prepare serially diluted cell suspensions ($10^{-2}$ to $10^{-6}$), and the cell suspensions were spotted (5 μl) onto L agar medium (10 g/L of Bacto trypton, 5 g/L of Bacto yeast extract, 5 g/L of NaCl, 15 g/L of agar) containing various concentrations (10, 15, 20 mM) of cysteine. Culture was performed at 37° C. overnight, and a growth test of the strain which is deficient in a part of or the entire tolC gene in the cysteine medium, and a complementation (recovery of growth) test with the tolC plasmid were performed. The results are shown in FIG. 1. The strain which is deficient in a part of or the entire tolC gene JW5503/pCA24 showed marked cysteine sensitivity as compared with the control strain BW25113/pCA24, and when the tolC gene was introduced as a plasmid (JW5503/pTolC strain), the strain recovered from the sensitivity. Therefore, it was found that TolC was involved in the cysteine resistance.

Figure 2:
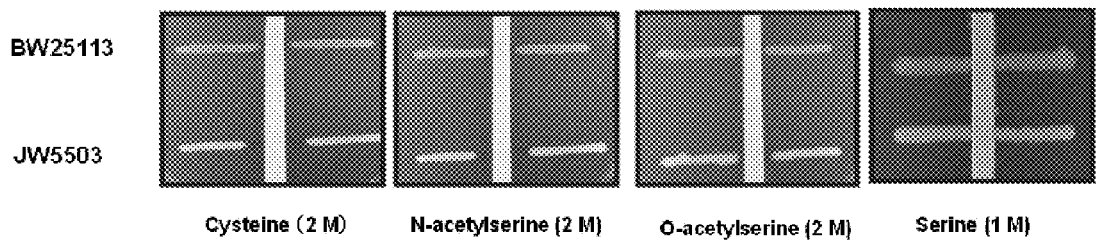
FIG. 2 shows the sensitivity (antibacterial activity) of a strain which is deficient in a part of or the entire tolC gene to O-acetylserine and N-acetylserine (photograph).

(1-3) Sensitivity to N-Acetylserine (NAS) and O-Acetylserine (OAS) Induced by tolC Gene Deficiency Influence of a tolC gene deficiency on N-acetylserine (NAS) and O-acetylserine (OAS) sensitivity was investigated in a strain which is deficient in a part of or the entire tolC gene by the cross streak method. In order to compare growth inhibition by NAS (2 M), OAS (2 M), L-cysteine (2 M) and L-serine (1 M), the tolC-deficient JW5503 strain, and the wild-type BW25113 strain used as a control, were cultured overnight in the L liquid medium, and each culture medium was streaked on the L agar medium with a platinum loop. A strip-shaped filter paper onto which each of the aforementioned reagents was dropped, was placed on each of the strains in a direction perpendicular to the streaking direction, and the strains were cultured overnight at 30° C. After the culture, lengths of the filter paper on which growth of the bacteria was inhibited (antibacterial widths) were measured, and the antibacterial activities of the regents on both the strains were compared. The results are shown in FIG. 2. The antibacterial widths are shown in Table 1.

It was found that the strain which is deficient in a part of or the entire tolC gene showed sensitivity to L-cysteine as described above. Also in this experiment, a larger antibacterial width was seen for the strain which is deficient in a part of or the entire tolC gene as compared to the wild-type strain, and sensitivity of the strain which is deficient in a part of or the entire tolC gene to L-cysteine was observed. The strain which is deficient in a part of or the entire tolC gene similarly showed large antibacterial widths for N-acetylserine (NAS) and O-acetylserine (OAS), and it became clear that it showed sensitivity to these substances.

TABLE 1

|  | Growth inhibition width (mm) | |
| --- | --- | --- |
|  | BW25113 | BW25113ΔtolC |
| L-Cysteine (2 M) | <1 | 5 |
| O-Acetylserine (2 M) | <1 | 4 |
| N-Acetylserine (2 M) | <2 | 10 |
| L-Serine (1 M) | 0 | 0 |

(2) Construction of Cysteine-Producing Bacterium (E. coli MG1655tnaA::Km$^r$pCEM256I/pYdeD)

A strain in which a tryptophanase gene was deleted, a mutant SAT gene was contained, and ydeD gene expression was enhanced was constructed from the E. coli MG1655 strain.

(2-1) Construction of Strain which is Deficient in a Part of or the Entire tnaA Gene of *E. coli* MG1655

A strain which is deficient in a part of or the entire tnaA gene of *E. coli* MG1655 was constructed by transducing tnaA::Km$^r$ of the *E. coli* JW3686 strain (Keio collection) into the MG1655 strain (ATCC No. 47076) using the P1kc phage. Preparation of a phage suspension and transduction were carried out as follows according to the method of Miller et al. (Miller, J. H., Experiments in molecular genetics, Cold Spring Harbor, N.Y: Cold Spring Harbor Laboratory; 1972, Generalized transduction: use of P1 in strain construction; pp. 201-205).

The JW3686 strain was cultured overnight at 37° C. in 3 ml of the L medium. To 3 ml of soft agar (0.5% agar), 100 μl of the culture medium, 100 μl of P1kc phage suspension and 100 μl of CaCl$_2$ (100 mM) were added, and the mixture was overlaid on the L medium containing 2.5 mM CaCl$_2$. After the soft agar solidified, culture was performed overnight at 37° C. On the soft agar on which plaques appeared, 2 ml of the L medium was added, the agar was disrupted, and the grown P1kc phages were collected. Chloroform was added in a volume of 100 μl to this L medium, they were mildly mixed, and the mixture was left standing at room temperature for 15 minutes. The cells and the soft agar were removed by centrifugation (4° C., 2,000×g, 5 minutes), and the supernatant was collected as a phage suspension. The *E. coli* MG1655 strain was cultured overnight at 37° C. in 3 ml of the L medium, and the culture was used as a preculture suspension of the recipient. The preculture suspension was inoculated in an amount of 1% into the L medium containing 5 mM CaCl$_2$, and culture was carried out at 37° C. with shaking until the OD$_{660}$ became 0.5. To this culture medium in a volume of 150 μl, an equivalent volume of the phage suspension diluted so that m.o.i. was 0.1 to 0.01 was added, and the mixture was kept at 37° C. for 30 minutes. After the phage particles were adsorbed, 100 μl of trisodium citrate solution (1 M) was added, and the mixture was kept at 37° C. for 60 minutes. The mixture was applied in a volume of 0.2 ml each to a selection medium, and culture was performed overnight at 37° C. The formed colonies were obtained as transductants. Transduction of the tnaA::Km$^r$ gene at the target position was confirmed by PCR and activity staining.

(2-2) Construction of Plasmid pCEM256I Carrying Feedback Inhibition-Resistant Mutant SAT Gene A plasmid having the same structure as that of pCEM256I described in literatures (Japanese Patent Laid-open No. 11-155571, Nakamori, S, et al., Appl. Environ. Microbiol., 1998, 64, 1607-1611) was used as a plasmid carrying a mutant SAT gene. pCEM256I had a mutant SAT gene obtained by introducing a mutation into the wild-type SAT gene (cysE) of *E. coli*. This mutant SAT gene includes substitution of isoleucine for the methionine at the 256-position, and shows resistance to the feedback inhibition by cysteine because of that mutation (Japanese Patent Laid-open No. 11-155571). Specifically, pCEM256I was obtained as follows.

In order to isolate the cysE gene including the promoter region and the terminator region, PCR was performed by using the chromosome of *E. coli* JM240 as a template, as well as a sense primer (5'-GGGAATTCATCGCTTCGGCGT-TGAAA-3', Primer 1, SEQ ID NO: 3) and an antisense primer (5'-GGCTCTAGAAGCGGTATTGAGAGAGATTA-3', Primer 2, SEQ ID NO: 4), which were prepared on the basis of the sequence of the cysE gene (coding for SAT) determined by Denk et al. (Denk, D. and Bock, A. J., General Microbiol., 133, 515-525 (1987)). PCR was performed by repeating a cycle consisting of reactions at 94° C. for 1 minute, 55° C. for 1 minute and 72° C. for 3 minutes, 25 times using DNA Thermal Cycler 480 (Perkin Elmer Co.) and Ex Taq polymerase. The specifically amplified DNA fragment of about 1.2 kb was ligated to the plasmid vector pBluscriptII SK$^+$ treated with EcoRV by a TA cloning technique to obtain pCE. It was confirmed by sequencing that the region amplified by PCR was the same as that of the wild-type.

Site-specific mutagenesis of the cysE gene was performed as follows. By using 5'-CAGGAAACAGCTATGAC-3' (Primer 3, SEQ ID NO: 5), 5'-CTGCAATCTGTGACGCT-3' (Primer 4, SEQ ID NO: 6), 5'-AATGGATATAGACCAGC-3' (Primer 5, SEQ ID NO: 7), and 5'-GCTGGTCTATATC-CATT-3' (Primer 6, SEQ ID NO: 8), isoleucine was substituted for the methionine residue at the 256th position of SAT. Primer 3 and Primer 4 were designed so that they are complementary to the 140 bp upstream region from the PstI site of the plasmid pCE, and the 50 bp downstream region from the BstEII site of the same, respectively. Primer 4 and Primer 5 were used as primers for site-specific mutagenesis. First, PCR was performed in separate tubes by using pCE as a template and Primer 3 and Primer 5, and Primer 4 and Primer 6, respectively. The obtained PCR products were subjected to agarose gel electrophoresis, and then collected from the gel. PCR was performed again by using the collected DNA fragments of 270 bp and 250 bp as templates, as well as Primer 3 and Primer 4. After the second PCR, the amplified DNA fragment of 500 bp was treated with the restriction enzymes PstI and BstEII, the obtained fragment of 310 bp was ligated with the large fragment of pCE similarly treated with the restriction enzymes to obtain pCEM256I. It was confirmed by sequencing that the intended mutation had been introduced. It was also confirmed that the other region was the same as that of the wild-type.

(2-3) Cloning of the ydeD Gene (Construction of Plasmid pYdeD for Enhancement of ydeD Gene)

*E. coli* ydeD gene coding for the cysteine secretion pump was cloned as follows. First, PCR was performed by using the genomic DNA of the *E. coli* MG1655 strain (ATCC No. 47076) as a template, a sense primer (5'-CGCGGATC-CAATGGTCATAAATGGCAGCGTAGCGC-3', Primer 7, SEQ ID NO: 9) and an antisense primer (5'-CGCGGATCCG-CAGGGCGTTGCGGAACAAAC-3', Primer 8, SEQ ID NO: 10). PCR was performed by using Pyrobest DNA polymerase (Takara) according to the protocol attached to the polymerase to obtain a ydeD gene fragment of about 1.5 kb including a region of about 300 bp upstream from the ydeD gene and a region of about 200 bp downstream from the ydeD gene. The BamHI site was designed in both the primers. The PCR fragment was digested with BamHI, and then inserted into the pSTV29 (Takara) at the BamHI site, and the obtained plasmid, in which the ydeD gene fragment was inserted in the same direction as the lacZ gene on the pSTV29 vector, was designated plasmid pYdeD. The portion amplified by PCR was sequenced to confirm that it did not contain PCR error.

(2-4) Construction of Cysteine-Producing Bacterium, MG1655ΔtnaA::Km$^r$/pCEM256I/pYdeD Strain pCEM256I and pYdeD were introduced into the MG1655ΔtnaA::Km$^r$ strain in a conventional manner to construct a cysteine-producing bacterium MG1655ΔtnaA::Km$^r$/pCEM256I/pYdeD strain, in which the mutant SAT and cysteine secretion pump YdeD were enhanced, and the cysteine decomposition system, TnaA, was deleted.

(3) Construction of Cysteine-Producing Bacterium in which TolC is Enhanced

In order to investigate the effect of enhancement of the tolC gene in a cysteine-producing bacterium, a plasmid for enhancement of the tolC gene was constructed, and introduced into the aforementioned cysteine-producing bacterium.

(3-1) Construction of Plasmid pLSTolC for Enhancement of TolC

First, the plasmid vector pMW219 (3,923 bp, NIPPON GENE) was digested with ClaI, and the 5' end was blunt-ended by using T4 DNA polymerase. Then, the kanamycin resistance gene of about 0.6 kb was excised with EcoT14I, and a large fragment of 3.2 kbp was collected. Then, the plasmid pFW5 (2,726 bp, Podbielski, A., et al., Gene, 1996, 177, 137-147) was digested with HindIII, then the 5' end was blunt-ended, and then the aad9 gene (spectinomycin resistance gene) of 1.2 kb was collected with EcoT14I. The plasmid constructed by ligating both the recovered fragments was designated pLS219 (4,444 bp). The tolC gene including the promoter region and the terminator region (2.6 kbp) was excised from the plasmid pUX (5208 bp, Aono, R., et al., J. Bacteriol., 1998, 180, 938-944) with HindIII and EcoRI. This excised tolC gene fragment was ligated to pLS219 at the HindIII-EcoRI site in the multi-cloning site (pLSTolC, 6,966 bp).

(3-2) Construction of TolC-Enhanced Cysteine-Producing Bacterium, E. coli MG1655ΔtnaA::Km$^r$/pCEM256I/pYdeD/pLSTolC pLSTol was introduced into the cysteine-producing bacterium, MG1655ΔtnaA::Km$^r$/pCEM256I/pYdeD, to construct the MG1655ΔtnaA::Km$^r$/pCEM256I/pYdeD/pLSTolC strain. The transformation was performed by electroporation in a conventional manner.

(4) Production of Cysteine by TolC-Enhanced Cysteine-Producing Bacterium

The TolC-enhanced cysteine-producing bacterium (E. coli MG1655 ΔtnaA::Km$^r$/pCEM256I/pYdeD/pLSTolC) and a control strain in which TolC was not enhanced (E. coli MG1655ΔtnaA::Km$^r$/pCEM256I/pYdeD) were each inoculated into 5 ml of the L medium (chloramphenicol (40 µg/mL), kanamycin (50 µg/mL) and ampicillin (50 µg/mL) were added, and spectinomycin (100 µg/mL) was further added for the strain having pLSTolC), and cultured overnight at 37° C. (preculture). Each cell suspension of the overnight culture was taken in a volume of 250 µl, and added to 25 ml of fresh medium (SM1+10% L medium), and culture was performed at 37° C. with shaking at 140 rpm. The culture medium was taken after 0, 3, 6, 9, 14 and 25 hours of the culture, and the cell number ($OD_{660}$) and the amount of produced cysteine were investigated. The composition of the SM1 medium used for the culture was as follows: 0.1 M $KH_2PO_4$—$K_2HPO_4$ buffer (pH 7.0), 30 g/L of glucose, 10 g/L of $(NH_4)_2SO_4$, 0.1 g/L of NaCl, 7.2 µM $FeSO_4.7H_2O$, 0.6 µM $Na_2MoO_4$, 40.4 µM $H_3BO_3$, 2.9 µM $CoCl_2$, 1 µM $CuSO_4$, 8.1 µM $MnCl_2$, 1 mM $MgSO_4$, and 0.1 mM $CaCl_2$ (Dassler, T., et al., Mol. Microbiol., 2000, 36, 1101-1112). The SM1+10% L medium was obtained by adding L medium components of 1/10 concentrations to the above SM1 medium.

Figure 3:
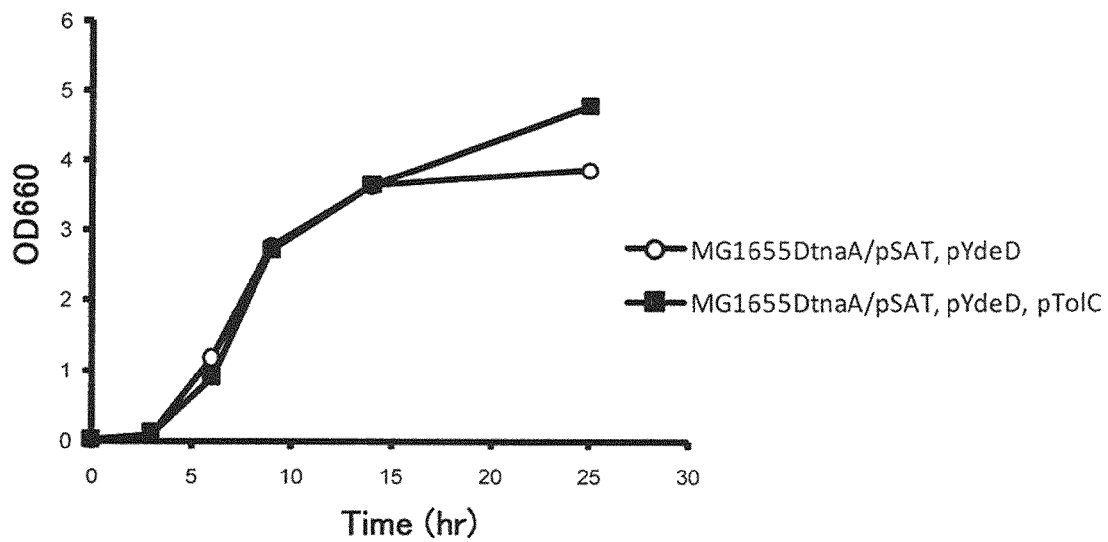
FIG. 3 shows the growth curve of a TolC-enhanced cysteine-producing bacterium.
Figure 4:
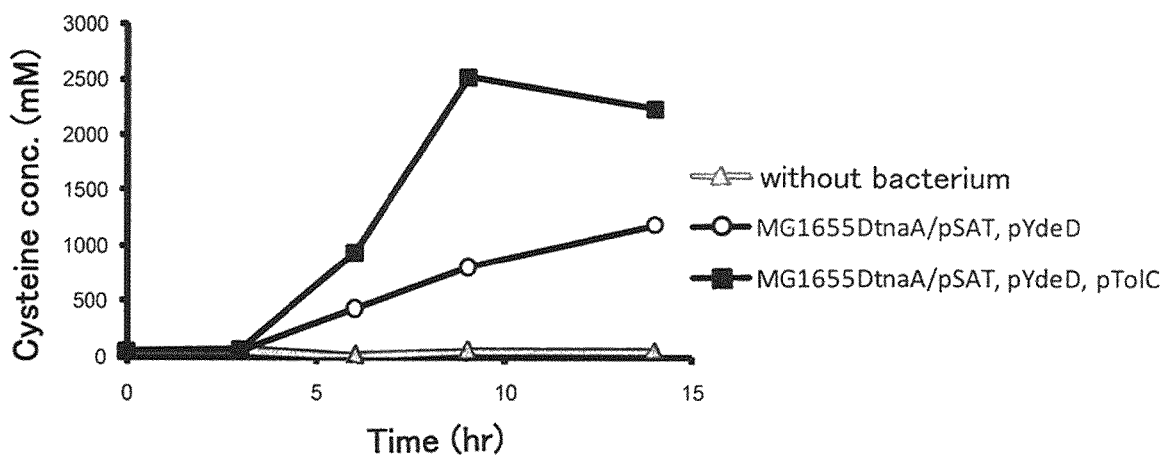
FIG. 4 shows cysteine production by a TolC-enhanced cysteine-producing bacterium.

Cysteine, cystine and cysteine-related compounds were quantified as follows according to the method of Gaitonde (Gaitonde, M. K., Biochem. J., 1967, 104, 627-633). To 100 µl of the culture medium, 200 µl of the Gaitonde reagent (250 mg of ninhydrin, 6 ml of acetic acid, 4 ml of hydrochloric acid) was added. The color developing reaction was performed at 100° C. for 5 minutes, and 400 µl of 100% ethanol was added to the mixture, and the $OD_{560}$ was measured. The growth curves are shown in FIG. 3, and the change in the amount of cysteine accumulated in the medium (amount quantified by the Gaitonde method) is shown in FIG. 4. It was found that the growth of the TolC-enhanced strain was substantially equivalent to that of the control strain, and it showed markedly increased cysteine amount. Thus, it became clear that enhancement of TolC had an effect of increasing cysteine production amount.

EXPLANATION OF SEQUENCE LISTING

SEQ ID NO: 1: Nucleotide sequence of E. coli tolC gene
SEQ ID NO: 2: Amino acid sequence of E. coli TolC
SEQ ID NOS: 3 to 10: PCR primers
SEQ ID NO: 11: Nucleotide sequence of Shigella boydii tolC gene homologue
SEQ ID NO: 12: Amino acid sequence of Shigella boydii TolC homologue
SEQ ID NO: 13: Nucleotide sequence of Shigella flexneri tolC gene homologue
SEQ ID NO: 14: Amino acid sequence of Shigella flexneri TolC homologue
SEQ ID NO: 15: Nucleotide sequence of Salmonella enterica tolC gene homologue
SEQ ID NO: 16: Amino acid sequence of Salmonella enterica TolC homologue
SEQ ID NO: 17: Nucleotide sequence of Citrobacter koseri tolC gene homologue
SEQ ID NO: 18: Amino acid sequence of Citrobacter koseri TolC homologue
SEQ ID NO: 19: Nucleotide sequence of Klebsiella pneumoniae tolC gene homologue
SEQ ID NO: 20: Amino acid sequence of Klebsiella pneumoniae TolC homologue
SEQ ID NO: 21: Nucleotide sequence of Enterobacter sakazakii tolC gene homologue
SEQ ID NO: 22: Amino acid sequence of Enterobacter sakazakii TolC homologue
SEQ ID NO: 23: Nucleotide sequence of Erwinia carotovora tolC gene homologue
SEQ ID NO: 24: Amino acid sequence of Erwinia carotovora TolC homologue
SEQ ID NO: 25: Nucleotide sequence of Serratia proteamaculans tolC gene homologue
SEQ ID NO: 26: Amino acid sequence of Serratia proteamaculans TolC homologue
SEQ ID NO: 27: Nucleotide sequence of Aeromonas salmonicida tolC gene homologue
SEQ ID NO: 28: Amino acid sequence of Aeromonas salmonicida TolC homologue
SEQ ID NO: 29: Nucleotide sequence of Vibrio vulnificus tolC gene homologue
SEQ ID NO: 30: Amino acid sequence of Vibrio vulnificus TolC homologue Industrial Applicability According to the present invention, the ability of bacteria to produce L-cysteine can be improved. Moreover, according to the present invention, L-cysteine, L-cystine, derivatives and precursors thereof, or mixtures thereof can be efficiently produced.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method for producing L-cysteine, L-cystine, a derivative or precursor thereof, or a mixture thereof, which comprises culturing a bacterium belonging to the family Enterobacteriaceae in a medium and collecting L-cysteine, L-cystine, a derivative or precursor thereof, or a mixture thereof from the medium, wherein the bacterium has the ability to produce L-cysteine and has been modified so that an activity of a protein encoded by a tolC gene is increased as compared to a non-modified bacterium, wherein the activity of the protein is increased by increasing expression amount of the tolC gene, increasing translation amount of the tolC gene, or combinations thereof.

2. The method according to claim 1, wherein the derivative of L-cysteine is a thiazolidine derivative.

3. The method according to claim 1, wherein the precursor of L-cysteine is O-acetylserine or N-acetylserine.

4. The method according to claim 1, wherein expression amount of the tolC gene is increased by increasing a copy number of the tolC gene, or by modifying an expression control sequence of the gene.

5. The method according to claim 1, wherein the protein is selected from the group consisting of:
    (a) a protein comprising the amino acid sequence of SEQ ID NO: 2, and
    (b) a protein comprising the amino acid sequence of SEQ ID NO: 2, but wherein one to five amino acid residues are substituted, deleted, inserted or added, wherein the increase of the activity in the bacterium improves the ability of the bacterium to produce L-cysteine.

6. The method according to claim 1, wherein the tolC gene is selected from a group consisting of:
    (a) a DNA comprising the nucleotide sequence of SEQ ID NO: 1,
    (b) a DNA which hybridizes with the nucleotide sequence of SEQ ID NO: 1, or a probe prepared from the nucleotide sequence, under stringent conditions comprising washing at 60° C. at a salt concentration of 0.1×SSC and 0.1% SDS, and codes for a protein, wherein the increase of the activity in the bacterium improves the ability of the bacterium to produce L-cysteine.

7. The method according to claim 1, wherein the bacterium contains a mutant serine acetyltransferase in which feedback inhibition by L-cysteine has been attenuated.

8. The method according to claim 1, wherein the bacterium has increased activity of the protein encoded by a ydeD gene.

9. The method according to claim 1, wherein the bacterium has decreased activity of a protein having cysteine desulfhydrase activity.

10. The method according to claim 7, wherein the bacterium has increased activity of the protein encoded by a ydeD gene.

11. The method according to claim 7, wherein the bacterium has decreased activity of a protein having cysteine desulfhydrase activity.

12. The method according to claim 8, wherein the bacterium has decreased activity of a protein having cysteine desulfhydrase activity.

13. The method according to claim 10, wherein the bacterium has decreased activity of a protein having cysteine desulfhydrase activity.

14. The method according to claim 9, wherein the protein having the cysteine desulfhydrase activity is tryptophanase.

15. The method according to claim 1, wherein the bacterium is an *Escherichia* bacterium.

16. The method according to claim 15, wherein the bacterium is *Escherichia coli*.

* * * * *